(12) United States Patent
McDonald et al.

(10) Patent No.: US 9,796,713 B2
(45) Date of Patent: Oct. 24, 2017

(54) TRICYCLIC COMPOUNDS AS ALPHA-7 NICOTINIC ACETYLCHOLINE RECEPTOR LIGANDS

(71) Applicant: BRISTOL-MYERS SQUIBB COMPANY, Princeton, NJ (US)

(72) Inventors: Ivar M. McDonald, East Haddam, CT (US); Richard E. Olson, Orange, CT (US); Robert A. Mate, Waterbury, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/317,553

(22) PCT Filed: Jun. 5, 2015

(86) PCT No.: PCT/US2015/034542
§ 371 (c)(1),
(2) Date: Dec. 9, 2016

(87) PCT Pub. No.: WO2015/191401
PCT Pub. Date: Dec. 17, 2015

(65) Prior Publication Data
US 2017/0129892 A1    May 11, 2017

Related U.S. Application Data

(60) Provisional application No. 62/011,622, filed on Jun. 13, 2014.

(51) Int. Cl.
*C07D 471/18*     (2006.01)
*C07D 519/00*     (2006.01)

(52) U.S. Cl.
CPC ......... *C07D 471/18* (2013.01); *C07D 519/00* (2013.01)

(58) Field of Classification Search
CPC .......................... C07D 471/18; C07D 519/00
See application file for complete search history.

(56) References Cited

FOREIGN PATENT DOCUMENTS

| WO | WO2007/024814 | * | 3/2007 |
| WO | WO2008/112734 | * | 9/2008 |

\* cited by examiner

*Primary Examiner* — Rita Desai
(74) *Attorney, Agent, or Firm* — James Epperson

(57) ABSTRACT

The disclosure provides compounds of formula I, including their salts, as well as compositions and methods of using the compounds. The compounds are ligands for the nicotinic α7 receptor and may be useful for the treatment of various disorders of the central nervous system, especially affective and neurodegenerative disorders.

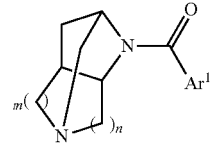

I

9 Claims, No Drawings

TRICYCLIC COMPOUNDS AS ALPHA-7 NICOTINIC ACETYLCHOLINE RECEPTOR LIGANDS

CROSS-REFERENCE TO RELATED APPLICATIONS

This application claims priority to U.S. Provisional Patent Application Ser. No. 62/011,622, filed Jun. 13, 2014, which is incorporated by reference in its entirety.

BACKGROUND OF THE INVENTION

The disclosure generally relates to compounds of formula I, including their salts, as well as compositions and methods of using the compounds. The compounds are ligands, agonists and partial agonists for the nicotinic $\alpha 7$ receptor and may be useful for the treatment of various disorders of the central nervous system, especially affective and neurodegenerative disorders.

Schizophrenia is a serious mental disorder, affecting approximately 1% of the population. Its progressive course results in major impairment of mental and social functioning and often leads to the development of other pathologies. Susceptibility often runs in families, with both genetic and environmental factors thought to be important. The direct and indirect costs of the disease are estimated in the tens of billion dollars annually in the U.S. alone.

Patients with schizophrenia have an elevated risk of suicide (approximately a 10% lifetime risk). They have a 2.5 fold increase in all-cause mortality, resulting in a 20% lowered life expectancy. The onset of illness can result in cascade of unhealthy lifestyle factors and behaviors that elevate the risk of various conditions and consequently the risk of death.

The onset of schizophrenia is most often in late adolescence or early adulthood, and episodes recur throughout life. The disease is characterized by the expression of three distinct symptom domains: positive, negative and cognitive. Psychotic or positive symptoms include delusions, hallucinations, thought disorder and paranoia. Negative symptoms include negative affect, social withdrawal, and anhedonia. Cognitive dysfunction includes deficits in attention, working memory and executive function. The pathophysiology of schizophrenia is not well understood, however, most experts believe it is a multi-factorial disorder in which biological, genetic and environmental factors play a role. Most current therapies target the dopaminergic system and have resulted in the suggestion that an excess of dopaminergic neurotransmission underlies at least some aspects of schizophrenia. This theory received further support from findings that drugs which increase the levels of dopamine cause psychoses similar to the positive symptoms of the disease. Also, post mortem analysis of brains from schizophrenic patients indicate increased numbers of D2 dopamine receptors. Although newer antipsychotic agents, known as atypical antipsychotics, which are active at several additional neurotransmitter receptors, have been introduced in the past decade, these agents still share efficacy against the D2 dopamine receptor. All currently-used agents also have major limitations. Although positive symptoms are generally reduced in a majority of patients, these drugs do little to relieve the negative symptoms and cognitive deficits that are common and often most debilitating. In addition, antipsychotic agents have a number of unwanted and limiting side effects.

Nicotine is among the few agents which have a positive effect on cognitive function. Many schizophrenics smoke; the rate in patients is 2-4 times that of the general population, and up to 90% in schizophrenics who have been institutionalized do smoke. This smoking habit has been characterized as a form of self-medication.

Nicotinic acetylcholine receptors (nAChR's) are pentameric ligand-gated ion channels which are widely expressed through the central and peripheral nervous system. These channels are fast-desensitizing calcium channels which, when open, increase the intracellular concentration of the $Ca^{++}$ ion. Although there are 12 individual receptors, the most abundant nicotinic receptors in the brain are $\alpha 4\beta 2$ and $\alpha 7$. The $\alpha 4\beta 2$ complex has been identified as the "high affinity" nicotine site. The homo-pentameric $\alpha 7$ receptor selectively binds the natural product, $\alpha$-bungarotoxin, which has allowed its relatively facile localization and measurement. The $\alpha 7$ receptor is primarily expressed in the cortex, hippocampus and subcortical limbic regions and commonly occurs pre-synaptically. The localization of $\alpha 7$ nAChRs in areas involved with learning and memory has led to studies using both knockout mice and pharmacological manipulation. It is involved in sensory gating, memory, and neuronal plasticity. Alpha7 agonists have been shown to increase the release of neurotransmitters in rodents, including dopamine, serotonin, glutamate and GABA. Compounds which selectively bind to the $\alpha 7$ receptor, such as $\alpha 7$ agonists and partial agonists, have been shown to improve learning and memory functions in normal and aged animals, reverse scopolamine-induced memory deficits, reverse deficits in cognition induced by NMDA antagonists, reverse pharmacologically-induced gating deficits, e.g. amphetamine induced gating disruption, and to possess some anxiolytic properties. The $\alpha 7$ agonists of the present invention are expected to be useful in the treatment of schizophrenia and cognitive disorders associated with schizophrenia.

Alzheimer's disease is a progressive neurodegenerative disorder, resulting in the general loss of cognitive functions. The incidence increases with age, to the degree that 25-50% of all individuals over 85 are estimated to suffer from some degree of dementia. A diagnosis of Alzheimer's implies that the remaining life expectancy is reduced by half, compared to normal adults.

Clinical signs of Alzheimer's disease are progressive cognitive deterioration, decreased ability to perform the activities of daily living and neuropsychiatric symptoms or behavioral changes. In the advanced stages of the disease, deterioration of musculature and mobility may lead to inability to feed oneself, and eventually to the patient becoming bedridden. Language becomes severely disorganized, and then is lost altogether. Patients are not able to perform even simple tasks independently and require constant supervision. The cost of institutional care makes up nearly 70% of the cost of the disease. Therefore, therapies which increase cognitive function and delay institutionalization are greatly needed.

Alzheimer's disease has been shown in several studies to be accompanied by a reduction in nicotinic receptors in the cortex and hippocampus. Nicotine injections or nicotine skin patches have been reported to significantly improve attention, memory and learning in Alzheimer's disease patients. While there is a progressive loss of nicotinic receptors during the course of Alzheimer's disease, the $\alpha 7$ neurons are relatively spared, compared to the more abundant $\alpha 4$ receptors. Recently, the administration of selective nicotinic $\alpha 7$ agonists has been shown to increase cognitive functioning in Alzheimer's patients when dosed as long as 8 weeks. This clinical data is consistent with pre-clinical data showing $\alpha 7$ agonists and partial agonists improve learning and memory functions in normal and aged animals and reverse scopolamine-induced memory deficits. Thus, the compounds of the present invention may be useful in the treatment and prevention of Alzheimer's disease. The amyloid peptide Aβ42 has been shown to bind to the α7 nicotinic receptor (Wang et al., J. Biol. Chem., 2000, 275:5626-5632; J. Neurochem. 2000, 75:1155-1161). This association may facilitate the aggregation of Aβ42, believed to be important in the toxic effects of Aβ42, and may also cause disregulation of signaling through α7 nicotinic receptors. Deletion of the α7 receptor gene improves cognitive deficits and synaptic pathology in a mouse model of Alzheimer's disease (Dziewczapolski et al., J. Neuroscience, 2009, pp 8805-8815). The compounds of the present invention may disrupt the interaction of Aβ342 and α7 receptors. Treatment with α7 agonists and partial agonists may represent an approach for disease modification in Alzheimer's disease. Alpha7 receptors may also mediate inflammatory processes in neurodegenerative conditions, such as Alzheimer's disease (Conejero-Goldberg et al., Neurosci. and Biobehav. Rev., 2008, 32, pp 693-706). The α7 agonists and partial agonists of the present invention may be useful in reducing inflammation in neurodegenerative diseases and disorders, such as Alzheimer's disease.

The α7 receptor has also been shown to be involved in the reduction of inflammation via the vagus nerve. In addition, the α7 receptor is expressed in synoviocytes from RA and OA patients, and α7 agonists have been shown to inhibit the proinflammatory cascade that occurs in the rheumatoid joint (Waldberger et al., Arthritis and Rheumatism, Vol 58, pp 3439-3449). Thus, the compounds of the present invention may be useful in the treatment of inflammatory conditions, such as rheumatoid arthritis and osteoarthritis.

Nicotinic receptors containing the α7 subunit are present on mucosal mast cells known to be involved in gastrointestinal hypersensitivity (Kageyama-Yahara et al., Biochem and Biophys. Research Commun., 2008, v. 377, pp 321-325). The α7 agonist GTS-21 inhibits the antigen-induced degranulation of mucosal mast cells, suggesting that α7 agonists may be useful in the treatment of hypersensitive bowel conditions, such as ulcerative colitis.

In a recent report (Marrero et al., JPET Fast Forward, Sep. 28, 2009, DOI: 10.1124/jpet.109.154633), an α7 agonist was shown to decrease weight gain and food intake and reduce the elevated plasma levels of triglycerides, glucose, glycated hemoglobin and TNFa in a mouse model of type II diabetes (db/db mice which are deficit in leptin receptors). The α7 agonists and partial agonists of the present invention may be useful in the treatment of diabetes.

The following references provide general reviews of the nicotinic receptor system and α7 receptors and ligands: Picciotto and Zoli, J. Neurobio. (2002) 53:641-655; Brening, et al, Ann. Reports in Med. Chem. (2005) 40:3-16; Dani and Bertrand, Ann. Rev. Pharm. Tox. (2007) 47:699-729; Olincy and Stevens, Biochem. Pharmacol. (2007) 74:1192-1201; Broad, et al, Drugs Future (2007) 32 (2):161-70; de Jonge and Ulloa, Brit. J. Pharmacol. (2007) 151:915-929; Romanelli, et al, ChemMedChem (2007) 2(6):746-767; Lightfoot et al., Progress in Medicinal Chemistry (2008), v 46, pp 131-171; Concotta et al., Current Opinion in Investigational Drugs (2008), v 9, pp 47-56; Leiser et al., Pharmacol. and Therapeutics (2009), doi:10:1016/j.pharmthera.2009.03.009).

The invention provides technical advantages, for example, the compounds are novel and are ligands for the nicotinic α7 receptor and may be useful for the treatment of various disorders of the central nervous system, especially affective and neurodegenerative disorders. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

The invention encompasses compounds formula I, including Ia and Ib, including pharmaceutically acceptable salts, and compositions and methods of treatment using these compounds. The compounds may be useful for the treatment of various disorders of the central nervous system:

One aspect of the invention is a compound of formula I, or a stereoisomer thereof,

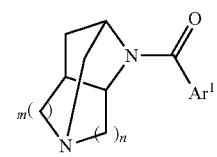

where:
$Ar^1$ is selected from the group consisting of phenyl, pyrrolyl, furanyl, thienyl, pyrazolyl, isoxazolyl, isothiazolyl, imidazolyl, oxazolyl, thiazolyl, triazolyl, oxadiazolyl, thiadiazolyl, pyridinyl, pyridazinyl, pyrimidinyl, pyrazinyl, naphthalenyl, indolyl, indazolyl, benzofuranyl, dihydrobenzofuranyl, benzodioxolanyl, benzothiophenyl, dihydrobenzothiophenyl, benzoisothiazolyl, benzothiazolyl, thienopyrazinyl, pyrrolopyridinyl, pyrrolotriazinyl, benzoisoxazolyl, quinolinyl, isoquinolinyl, quinoxalinyl, and naphthyridinyl, and is substituted with 0-3 substituents selected from the group consisting of cyano, halo, alkyl, haloalkyl, cycloalkyl, alkoxy, haloalkoxy, alkylthio, and $Ar^2$;
$Ar^2$ is phenyl substituted with 0-3 substituents selected from cyano, halo, alkyl, haloalkyl, alkoxy, and haloalkoxy; and
m is 2 and n is 1; or
m is 1 and n is 2; or
m is 0 and n is 3;
or a pharmaceutically acceptable salt thereof.

Another aspect of the invention is a compound of formula I where:
$Ar^1$ is phenyl, pyrazolyl, indolyl, indazolyl, pyrazolopyridinyl, benzofuranyl, thiophenyl, benzoisoxazolyl, benzoisothiazolyl, or isoquinolinyl, and is substituted with 0-3 substituents selected from the group consisting of cyano, halo, alkyl, haloalkyl, cycloalkyl, alkoxy, haloalkoxy, alkylthio, and $Ar^2$; and
$Ar^2$ is phenyl substituted with 0-3 substituents selected from cyano, halo, alkyl, haloalkyl, alkoxy, and haloalkoxy;
or a pharmaceutically acceptable salt thereof.

Another aspect of the invention is a compound of formula I where $Ar^1$ is phenyl, pyrazolyl, indolyl, indazolyl, pyrazolopyridinyl, benzofuranyl, thiophenyl, benzoisoxazolyl, benzoisothiazolyl, or isoquinolinyl, and is substituted with 0-1 substituents selected from halo, alkyl, cycloalkyl, alkoxy, and $Ar^2$; and $Ar^2$ is phenyl; or a pharmaceutically acceptable salt thereof.

Another aspect of the invention is a compound of formula I where m is 2 and n is 1.

Another aspect of the invention is a compound of formula I where m is 1 and n is 2.

Another aspect of the invention is a compound of formula I where m is 0 and n is 3.

Another aspect of the invention is a compound of formula I where $Ar^1$ is indazolyl substituted with 0-3 substituents selected from the group consisting of cyano, halo, alkyl, haloalkyl, cycloalkyl, alkoxy, and haloalkoxy; or a pharmaceutically acceptable salt thereof.

For a compound of formula I, the scope of any instance of a variable substituent, including $Ar^1$, $Ar^2$, m and n, can be used independently with the scope of any other instance of a variable substituent. As such, the invention includes combinations of the different aspects.

Unless specified otherwise, these terms have the following meanings. "Halo" includes fluoro, chloro, bromo, and iodo. "Alkyl" means a straight or branched alkyl group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. "Cycloalkyl" means a monocyclic ring system composed of 3 to 7 carbons. "Haloalkyl" and "haloalkoxy" include all halogenated isomers from monohalo to perhalo. Terms with a hydrocarbon moiety (e.g. alkoxy) include straight and branched isomers for the hydrocarbon portion. "Aryl" means a monocyclic or bicyclic aromatic hydrocarbon groups having 6 to 12 carbon atoms, or a bicyclic fused ring system wherein one or both of the rings is a phenyl group. Bicyclic fused ring systems consist of a phenyl group fused to a four- to six-membered aromatic (for example, naphthyl) or non-aromatic (for example, indanyl, indenyl, tetrahydronaphthyl) carbocyclic ring. "Heteroaryl" means a 5 to 7 membered monocyclic or 8 to 11 membered bicyclic aromatic ring system with 1-5 heteroatoms independently selected from nitrogen, oxygen, and sulfur. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereromers. Methods of making and separating stereoisomers are known in the art.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Synthetic Methods

The compounds may be made by methods known in the art including those described below and including variations within the skill of the art. Some reagents and intermediates are known in the art. Other reagents and intermediates can be made by methods known in the art using commercial materials. The variables (e.g. numbered "R" substituents) used to describe the synthesis of the compounds are intended only to illustrate how to make the compounds and are not to be confused with variables used in the claims or in other sections of the specification. The following methods are for illustrative purposes and are not intended to limit the scope of the invention.

Some of the compounds may be prepared using the reactions and techniques described in this section. The reactions are performed in solvents appropriate to the reagents and materials employed and are suitable for the transformations being effected. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC" for t-butoxycarbonyl, "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "$Et_2O$" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for $CF_3(CF_2)_3SO_2$—; and "TMOF" for trimethylorthoformate.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" "for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "¹H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

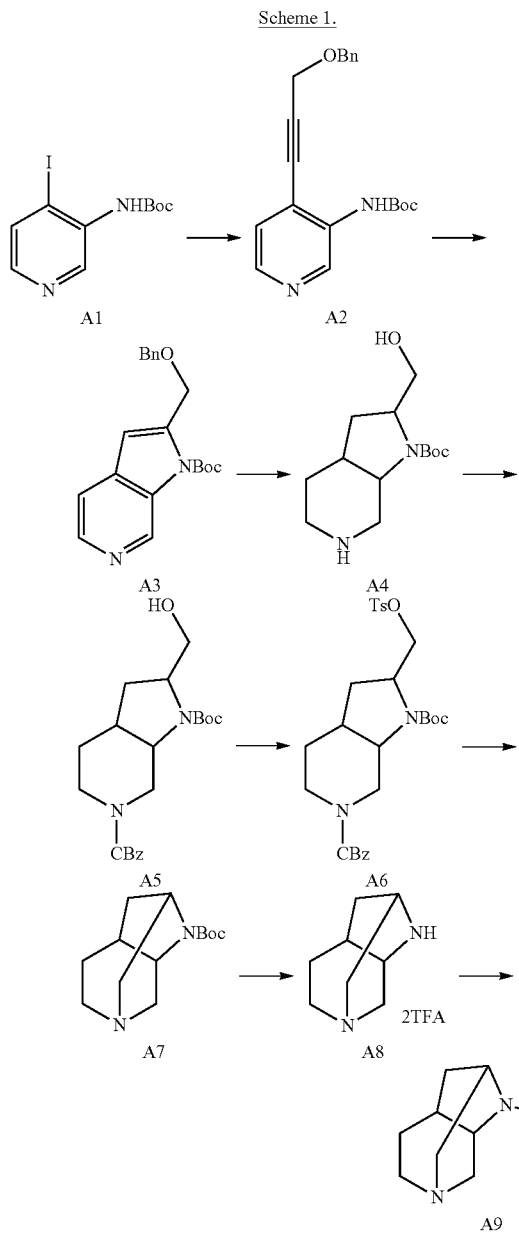

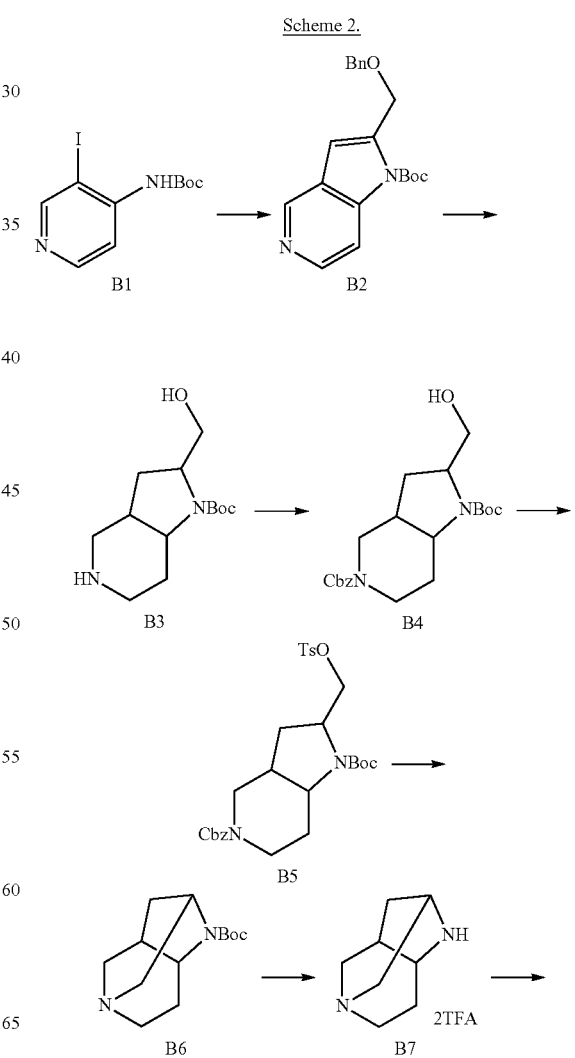

Compounds of Formula I can be prepared as illustrated in Reaction Scheme 1. The iodopyridine of Formula A1 is known and may be prepared by methods known to those skilled in the art. The iodopyridine of Formula A1 may be converted to the azaindole of Formula A3 by reaction with benzyl propargyl ether in the presence of palladium and copper catalysts followed by cyclization with a base such as DBU and reprotection of the indole with a protecting group such as a Boc group. Alternatively, iodopyridine A1 may be converted to azaindole A3 directly by proper choice of reaction conditions upon treatment with benzyl propargyl ether in the presence of palladium and copper catalysts. Azaindole A3 can be converted to piperidine A4 by hydrogenation over palladium and/or platinum catalysts. The compound of Formula A4 can be converted to the compound of Formula A5 by treatment with benzylchloroformate. Conversion of the alcohol found in compound A5 into a good leaving group, for example a tosylate, can be achieved under a range of conditions known to those skilled in the art, for example, by treatment with tosyl chloride in pyridine. Tosylate A6 can be cyclized to tricycle A7 by hydrogenolysis over a catalyst, for example palladium on carbon, followed by treatment with base, for example potassium carbonate, and warming.

Cleavage of the Boc group found in tricycle A7, affording amine A8, can be performed by methods known to those skilled in the art, for example, treatment with trifluoroacetic acid or hydrogen chloride. Conversion of A8 to compounds of Formula 1 can be performed by a variety of methods known to those skilled in the art, for example by treatment with the appropriate carboxylic acid, an amide coupling reagent such as HATU or EDC and an amine base such as triethylamine or diisopropylethylamine.

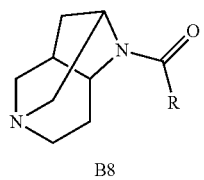

B8

Compounds of Formula I can be prepared as illustrated in Reaction Scheme 1. The iodopyridine of Formula D1 is known and may be prepared by methods known to those skilled in the art. The iodopyridine of Formula B1 may be converted to the azaindole of Formula B2 by reaction with benzyl propargyl ether in the presence of palladium and copper catalysts. Azaindole B2 can be converted to piperidine B3 by hydrogenation over palladium or platinum catalysts.

The compound of Formula B3 can be converted to the compound of Formula B4 by treatment with benzylchloroformate. Conversion of the alcohol found in compound D4 into a good leaving group, for example a tosylate, can be achieved under a range of conditions known to those skilled in the art, for example, by treatment with tosyl chloride in pyridine. Tosylate B5 can be cyclized to tricycle D6 by hydrogenolysis over a catalyst, for example palladium on carbon, followed by treatment with base, for example potassium carbonate, and warming.

Cleavage of the Boc group found in tricycle B6, affording amine B7, can be performed by methods known to those skilled in the art, for example, treatment with trifluoroacetic acid or hydrogen chloride. Conversion of B7 to compounds of Formula 1 can be performed by a variety of methods known to those skilled in the art, for example by treatment with the appropriate carboxylic acid, an amide coupling reagent such as HATU or EDC and an amine base such as triethylamine or diisopropylethylamine.

Homochiral compounds of Formulae Ia or Ib can be prepared by supercritical fluid chromatography on a chiral column, either at the stage of the final compound, or at an intermediate stage, such as compound B4 or B5.

Scheme 3.

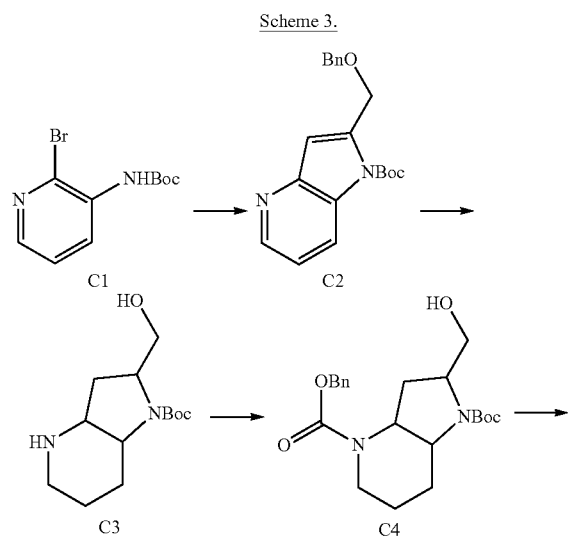

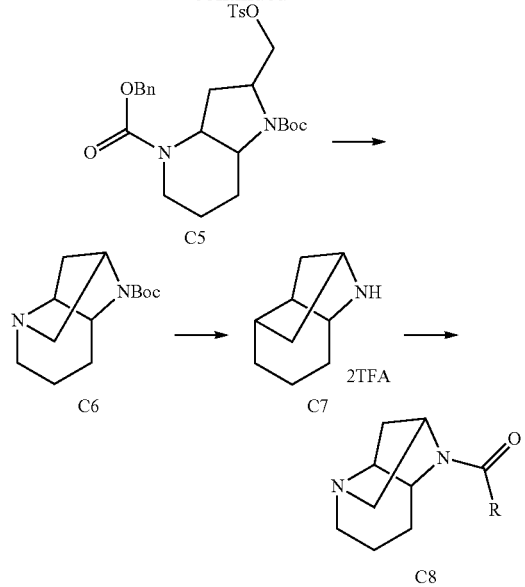

Compounds of Formula I can be prepared as illustrated in Reaction Scheme 1. The bromopyridine of Formula C1 is known and may be prepared by methods known to those skilled in the art. The bromopyridine of Formula C1 may be converted to the azaindole of Formula C2 by reaction with benzyl propargyl ether in the presence of palladium and copper catalysts. Azaindole C2 can be converted to piperidine C3 by hydrogenation over palladium and/or platinum catalysts.

The compound of Formula C3 can be converted to the compound of Formula C4 by treatment with benzylchloroformate. Conversion of the alcohol found in compound C4 into a good leaving group, for example a tosylate, can be achieved under a range of conditions known to those skilled in the art, for example, by treatment with tosyl chloride in pyridine. Tosylate C5 can be cyclized to tricycle C6 by hydrogenolysis over a catalyst, for example palladium on carbon, followed by treatment with base, for example potassium carbonate, and warming.

Cleavage of the Boc group found in tricycle C6, affording amine C7, can be performed by methods known to those skilled in the art, for example, treatment with trifluoroacetic acid or hydrogen chloride. Conversion of C7 to compounds of Formula 1 can be performed by a variety of methods known to those skilled in the art, for example by treatment with the appropriate carboxylic acid, an amide coupling reagent such as HATU or EDC and an amine base such as triethylamine or diisopropylethylamine.

Biological Methods

I) α7 Nicotinic Acetycholine Receptor Binding. Membranes were prepared for binding using HEK293 cells stably expressing the rat α7 nicotinic acetycholine receptor (rat α7 nAChR). Cells were homogenized at 4° C. in hypotonic lysis buffer consisting of 10 mM Tris (pH 7.4), 5 mM EDTA and protease inhibitors and centrifuged at 32000×g for 20 minutes. The pellet was washed once in membrane wash buffer consisting of 50 mM Tris (pH 7.4), 1 mM EDTA and protease inhibitors and centrifuged at 32000×g for 20 minutes. This pellet was then resuspended in assay buffer consisting 50 mM $KH_2PO_4$ (pH 7.4 at 25° C.), 1 mM EDTA, 0.005% Triton-X 100 and 0.1% (v/v) Sigma Protease Inhibitor Cocktail. Aliquots were then frozen in dry ice/ethanol and kept at −80° C. until the day of the assay.

II) A $Ca^{2+}$-Sensitive, Fluorescence-Based Assay α-7 for Nicotinic Acetylcholine Receptor Channel Function in Mammalian Cells ("FLIPR"). Summary: Lead compounds are evaluated for agonist activity at α-7, α3β4, α4β2, and α1β1δε sub-types of nicotinic ACh receptor ion channels expressed in mammalian HEK 293 cells. Agonist potency and efficacy values are determined from kinetic fluorescence $Ca^{2+}$ influx measurements made using a 384 well FLIPR (Fluorescence Image Plate Reader). The utility of fluorescent indicators for measuring changes in intracellular divalent cation concentrations, particularly $Ca^{2+}$, for drug discovery endeavors is well documented (Rudiger, R., et al., *Nature Reviews*, 2003, 4:579-586; Gonzalez J. E., et al., *Receptors and Channels*, 2002, 8:283-295). In this assay, channel expressing HEK cell lines seeded in 384 well assay plates are loaded with a membrane permeant fluorescent $Ca^{2+}$ indicator dye, whose 510 nm green emission signal increases in response to elevation of intracellular $Ca^{2+}$ concentration. The basal fluorescence from the cells is monitored in real time, followed by the acute addition of test compounds. If the compound is an agonist at any of the non-selective cation channels, the latter open and allow the movement of extracellular $Ca^{2+}$ ions into the cell cytoplasm, where they bind to the $Ca^{2+}$ indicator dye, and produce an increase in fluorescence output signal, which is detected by a cooled CCD imaging camera.

Materials and Methods: Reagents: The acetomethoxy (AM) ester of the $Ca^{2+}$ indicator dye Fluo-4 was obtained from InVitrogen, (Carlsbad, Calif.). Acetylcholine and all buffer constituents were purchased from Sigma Chemical Company, St. Louis, Mo. G418 and Minimal Essential Medium were purchased from InVitrogen Life Technologies, Carlsbad, Calif. Fetal bovine serum was purchased from (InVitrogen, Carlsbad, Calif.).

Cell Culture: HEK-293 cells were grown in Minimal Essential Medium containing 10% (v/v) fetal bovine serum at 37° C. in a 5% $CO_2$ incubator. HEK-293 cells stably expressing the ion channels were grown in the same medium with the addition of 500 μg/ml G418.

$Ca^{2+}$ flux assays of $Ca^{2+}$ channels expressed in HEK-293 cells: HEK-293 cells expressing the ion channels of interest were plated in 384 well, black-walled, clear-bottomed, poly-D-lysine coated plates at a density of ~20,000 cells/well in 20 μl of Minimal Essential Medium containing 10% (v/v) fetal bovine serum and incubated for 2 days at 29° C. in a 5% $CO_2$ incubator. Prior to assay, cells were loaded with the Fluo-4 AM ester. Cell loading was accomplished by removing the culture medium and replacing it with 30 μl/well of the AM ester of the dye (5 μM) mixed with Hanks Balanced Salt Solution (#14175-095) containing 20 mM HEPES, 2.5 mM probenecid, 0.5 mM $CaCl_2$, 1 mM MgCl2 and 10 μM atropine. Dye loading was allowed to proceed for 90 minutes at room temperature at which time the dye loading solution was removed and replaced with 40 μl/well of Hanks buffer. Cells loaded with dye were loaded onto a FLIPR384 (Molecular Devices, Sunnyvale, Calif.). Fluo-4 dye was excited using the 488 nm line of an argon laser. Emission was filtered using a 540+/−30 nm bandpass filter. For evaluation of the effects of test compounds using the $Ca^{2+}$ flux assay, compounds to be tested were provided in assay ready plates. For nicotinic receptor ion channel expressing cells, the assay was initiated by the addition of 20 μl/well of Hanks buffer containing test compounds. For all assays, data were collected at 1 Hz for 10 seconds (baseline), at which time the compound containing stimulus buffers are added, and further measurements collected at 0.33 Hz for 3 min.

Data Analysis: The statistical robustness of the nicotinic receptor $Ca^{2+}$ flux assays is determined from blanks and totals wells. The totals wells define maximal channel activation for each compound test plate (Maximum efficacious dose of acetylcholine), and the blanks wells which contain matched DMSO only, define zero channel activation. The raw fluorescence units data files generated on the FLIPR plate reader are automatically exported and processed by in-house data analysis tools. The reduced percent activation data for each concentration of test compound are fit using MathIQ fitting engine (ID Business Solutions Limited, Surrey, UK). Data were analyzed by fitting maximum amplitudes of change in fluorescence, for $Ca^{2+}$ flux for a given condition of test compound. Potencies ($EC_{50}$ values) of compounds are calculated from the average of three assay wells from a twenty point CRC. Test compound efficacy values (Ymax values) are expressed relative to a maximal response to acetylcholine in the total wells.

III) Fos Quantification Assay: Male Wistar rats are treated with drug (1-10 mg/kg) or vehicle (2 ml/kg, sc). Two hours after treatments, the rats are rapidly decapitated and discrete brain regions of interest are isolated on ice and weighed and flash frozen with liquid nitrogen and stored at −80 deg. C. Further processing of the brain tissue for nuclear extracts as well as for Fos quantification are in accordance with the protocol prescribed by a commercially available ELISA-based chemiluminescence detection kit (catalog #89860, EZ-detect c-Fos Trans kit, Pierce Biotechnology Inc., Rockford, Ill.).

IV) MK-801 Disrupted Set-Shift Assay in Rats: This assay uses a modification of the protocol described by Stefani et al. (*Behavioral Neuroscience*, 2003, 117: 728-737). Test compounds are assessed for their ability to reverse an MK-801-induced performance deficit (0.03 mg/kg, i.p., single dose) in this assay.

The activity of compounds described and tested in the above assay (II) is provided in Tables 1-4.

TABLE 1

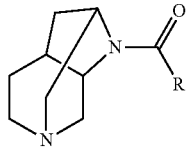

| Example Number | R | FLIPR α7 ($EC_{50}$, nM) |
|---|---|---|
| 1 | 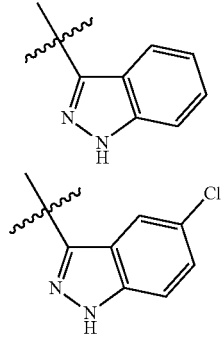 | 73 |
| 2 | | 590 |

TABLE 1-continued
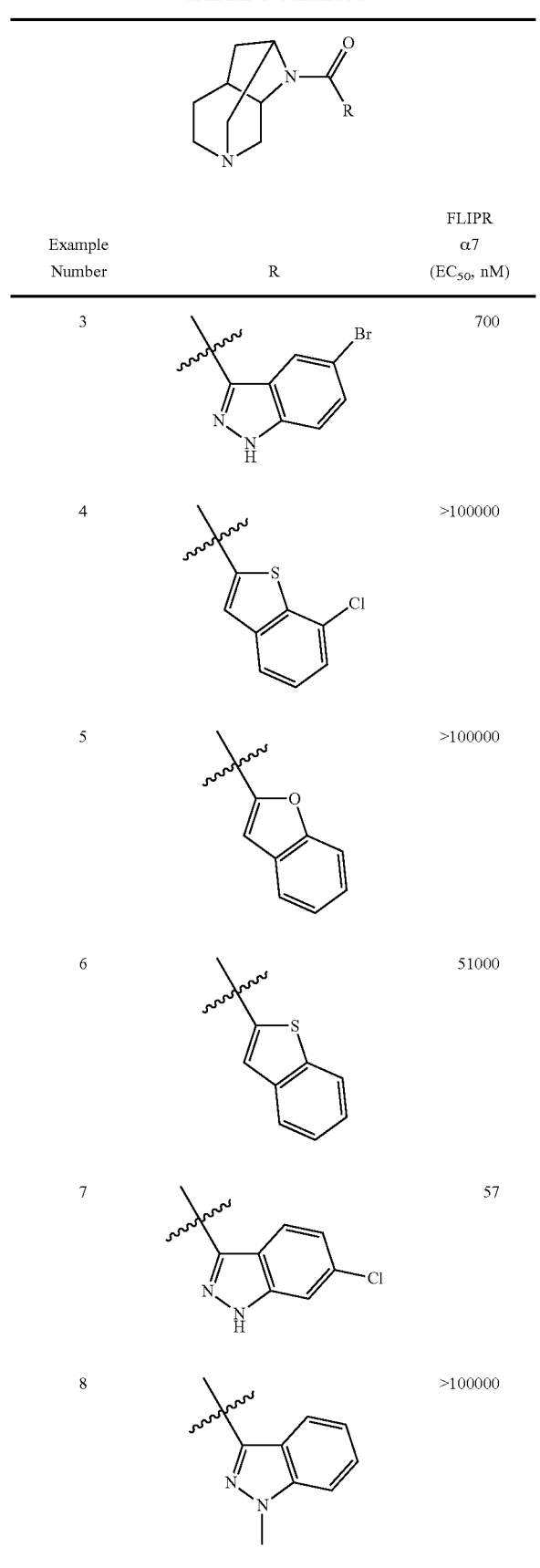
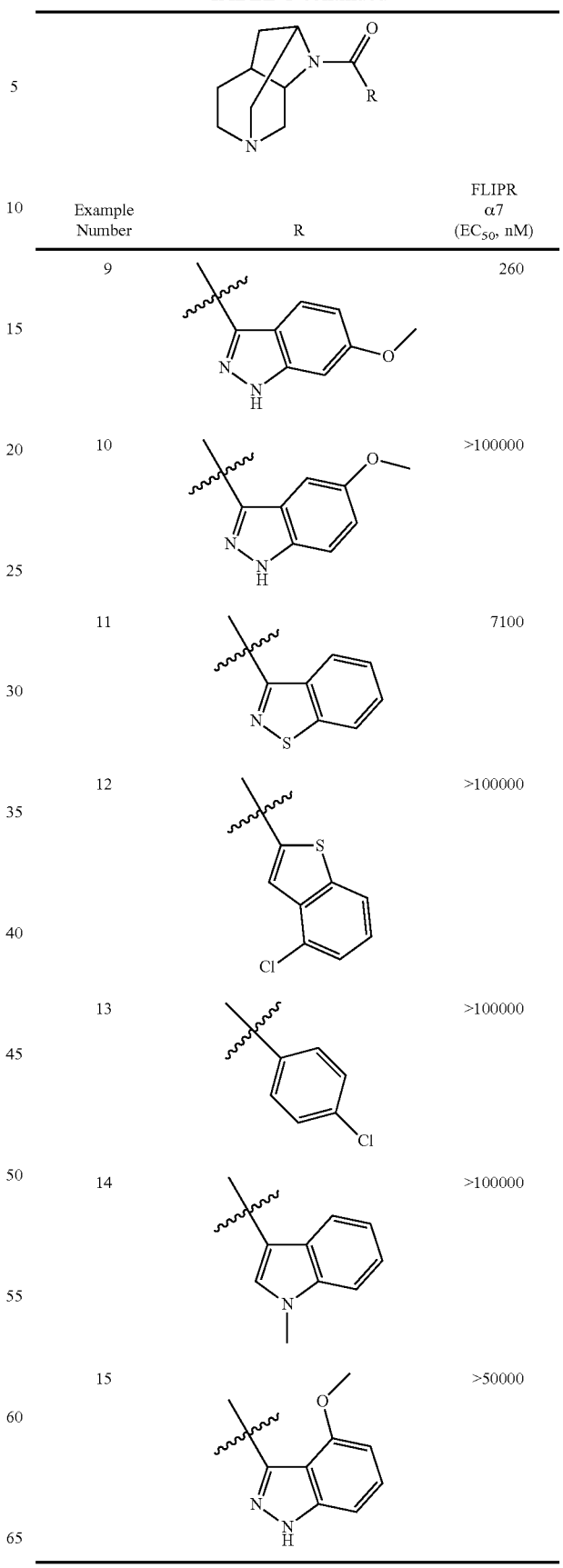

TABLE 2
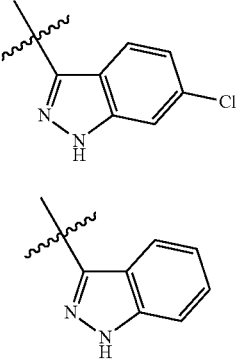
| Example Number | R | FLIPR α7 (EC$_{50}$, nM) |
|---|---|---|
| 17 | 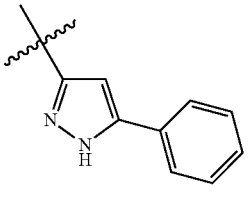 [SMILES: *c1cc(-c2ccccc2)[nH]n1] | 30 |
| 18 | 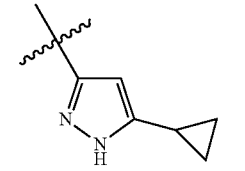 [SMILES: *c1cc(C2CC2)[nH]n1] | 55 |
| 19 | 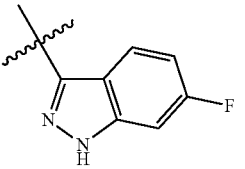 [SMILES: *c1n[nH]c2cc(F)ccc12] | >100000 |
| 20 | 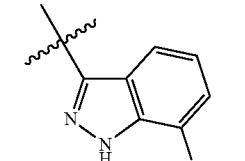 | 26000 |
| 21 | 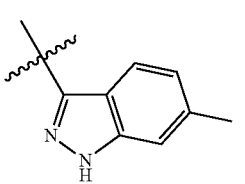 [SMILES: *c1n[nH]c2cc(C)ccc12] | 80 |
| 22 | 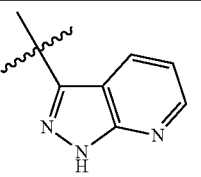 | 3600 |
| 23 | 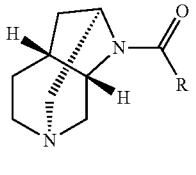 | 39 |
| 24 | 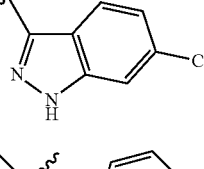 | 1300 |
TABLE 3
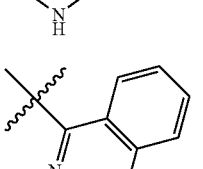
| Example Number | R | FLIPR α7 (EC$_{50}$, nM) |
|---|---|---|
| 16 | 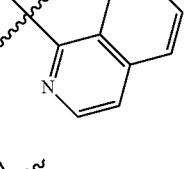 | 86 |
| 25 | 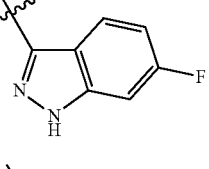 | 45000 |
| 26 | 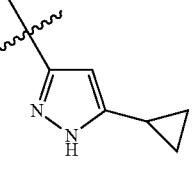 | 430 |
| 27 | 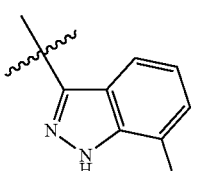 | >100000 |
| 28 | 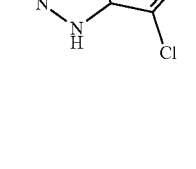 | 36000 |

TABLE 3-continued

[Structure: bicyclic amine scaffold with NH, bridgehead H's, and N-C(=O)-R substituent]

| Example Number | R | FLIPR α7 (EC$_{50}$, nM) |
|---|---|---|
| 29 | 1,2-benzisoxazol-3-yl | 3100 |
| 30 | 6-methyl-1H-indazol-3-yl | 190 |
| 31 | 1H-pyrazolo[3,4-b]pyridin-3-yl | 9200 |
| 32 | 5-phenyl-1H-pyrazol-3-yl | >100000 |
| 33 | 1H-indazol-3-yl | 150 |

TABLE 4

[Structure: bridged bicyclic diamine scaffold with N-C(=O)-R substituent]

| Example Number | R | FLIPR α7-HI (EC$_{50}$, nM) |
|---|---|---|
| 34 | 1H-indazol-3-yl | 29 |
| 34a | 1H-indazol-3-yl | 7.5 |
| 34b | 1H-indazol-3-yl | 250 |
| 35 | 7-chlorobenzo[b]thiophen-2-yl | 5600 |
| 36 | 4-chlorophenyl | >100000 |
| 37 | 1-methyl-1H-indazol-3-yl | >100000 |
| 38 | 5-phenyl-1H-pyrazol-3-yl | >100000 |

TABLE 4-continued

| Example Number | R | FLIPR α7-HI (EC$_{50}$, nM) |
|---|---|---|
| 39 | 1-methyl-1H-indol-3-yl | >100000 |
| 40 | 5-chloro-1H-indazol-3-yl | 79 |
| 41 | 5-methoxy-1H-indazol-3-yl | >100000 |
| 42 | 6-fluoro-1H-indazol-3-yl | 54 |
| 43 | 6-methoxy-1H-indazol-3-yl | 23 |
| 44 | 5-bromo-1H-indazol-3-yl | >100000 |
| 45 | 7-chloro-1H-indazol-3-yl | >100000 |
| 46 | 6-chloro-1H-indazol-3-yl | 10 |
| 47 | 1,2-benzisoxazol-3-yl | 1300 |
| 48 | 4-methoxy-1H-indazol-3-yl | 7400 |
| 49 | 6-methyl-1H-indazol-3-yl | 4.2 |
| 49a | 6-methyl-1H-indazol-3-yl | 3.1 |
| 49b | 6-methyl-1H-indazol-3-yl | 47 |

TABLE 5

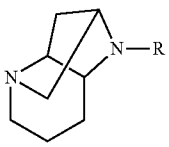

| Example Number | R | FLIPR α7-HI (EC$_{50}$, nM) |
|---|---|---|
| 50 | 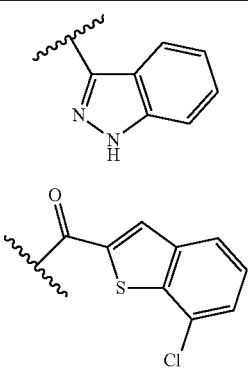 | 360 |
| 51 |  | >100000 |

Pharmaceutical Compositions and Methods of Treatment

Compounds of formula I bind to the alpha7 nicotinic acetylcholine receptor and can be useful in treating affective disorders and neurodegenerative disorders. Therefore, another aspect of the invention is a composition comprising a compound of formula I, or a pharmaceutically acceptable salt thereof, and a pharmaceutically acceptable carrier.

Another aspect of the invention is the use of a compound of formula I in the manufacture of a medicament for the treatment of affective disorders or neurodegenerative disorders.

Another aspect of the invention is the use of a compound of formula I in the manufacture of a medicament for the treatment of schizophrenia or Alzheimer's Disease.

Another aspect of the invention is a method of treating affective disorders or neurodegenerative disorders comprising administering to a patient a therapeutically effective amount of a compound of formula I.

Another aspect of the invention is a method of treating schizophrenia or Alzheimer's Disease comprising administering to a patient a therapeutically effective amount of a compound of formula I.

Another aspect of the invention is a method of treating schizophrenia comprising administering to a patient a therapeutically effective amount of a compound of formula I.

Another aspect of the invention is a method of treating Alzheimer's Disease comprising administering to a patient a therapeutically effective amount of a compound of formula I.

Another aspect of the invention is a method of treating cognitive disorders comprising administering to a patient a therapeutically effective amount of a compound of formula I.

Another aspect of the invention is a method of treating rheumatoid arthritis comprising administering to a patient a therapeutically effective amount of a compound of formula I.

Another aspect of the invention is a method of treating osteoarthritis comprising administering to a patient a therapeutically effective amount of a compound of formula I.

Another aspect of the invention is a method of treating ulcerative colitis comprising administering to a patient a therapeutically effective amount of a compound of formula I.

Another aspect of the invention is a method of treating Crohn's Disease comprising administering to a patient a therapeutically effective amount of a compound of formula I.

Another aspect of the invention is a method of treating diabetes comprising administering to a patient a therapeutically effective amount of a compound of formula I.

"Patient" means a person suitable for therapy as understood by practitioners in the field of affective disorders and neurodegenerative disorders.

"Treatment," "therapy," and related terms are used as understood by practitioners in the field of affective disorders and neurodegenerative disorders.

The compounds of this invention are generally given as pharmaceutical compositions comprised of a therapeutically effective amount of a compound or its pharmaceutically acceptable salt and a pharmaceutically acceptable carrier and may contain conventional excipients. Pharmaceutically acceptable carriers are those conventionally known carriers having acceptable safety profiles. Compositions encompass all common solid and liquid forms including for example capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, Mack Publishing Company, Easton, Pa., 17th edition, 1985.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

DESCRIPTION OF SPECIFIC EMBODIMENTS

$^1$H-NMR spectra were run on a Bruker 600, 500, or 400 MHz instrument and chemical shifts were reported in ppm (δ) with reference to tetramethylsilane (δ=0.0). All evaporations were carried out under reduced pressure.

LC/MS Analysis Methods:

LC/MS analysis Method A: Phenomenex-Luna 50×2.0 mm 3.0 um column employing a flow rate of 0.8 mL/min with Mobile Phase A: 5:95 methanol:water with 10 mM ammonium acetate; Mobile Phase B: 95:5 methanol:water with 10 mM ammonium acetate; Temperature: 40° C.; A gradient elution [0-100% in 4 min, with a 5 min run time] Flow: 0.8 mL/min. and a UV detector set at 220 nm.

LC/MS analysis Method B: Column: Waters BEH C18, 2.0×50 mm, 1.7-μm particles; Mobile Phase A: water with 0.05% TFA; Mobile Phase B: acetonitrile with 0.05% TFA; [2-98% in 1.5 min, with a 2 min run time]; Flow: 0.8 mL/min.

LC/MS analysis Method C: Phenomenex-Luna 50×2.0 mm 3.0 um column employing a flow rate of 0.8 mL/min with solvent A=9:1 Water/Methanol+0.1% TFA and solvent B=1:9 Water/Methanol+0.1% TFA. A gradient elution [0-100% in 4 min, with a 5 min run time] and a UV detector set at 220 nm.

LC/MS analysis Method D: Phenomenex-Luna 50×2.0 mm 3.0 um column employing a flow rate of 0.8 mL/min with solvent A=9:1 Water/Acetonitrile+0.1% TFA and solvent B=1:9 Water/Acetonitrile+0.1% TFA. A gradient elution [0-100% in 4 min, with a 5 min run time] and a UV detector set at 220 nm.

Example 1

(hexahydro-2,6-methanopyrrolo[2,3-c]pyridin-1 (2H)-yl)(1H-indazol-3-yl)methanone

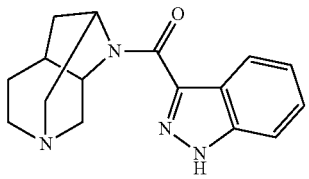 [SMILES: O=C(c1n[nH]c2ccccc12)N1C2CC3CCN(C2)CC31]

Step A: tert-butyl (4-(3-(benzyloxy)prop-1-yn-1-yl) pyridin-3-yl)carbamate

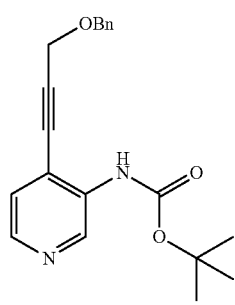 [SMILES: CC(C)(C)OC(=O)Nc1cnccc1C#CCOCc1ccccc1]

A resealable pressure vessel was charged with tert-butyl tert-butyl (4-iodopyridin-3-yl)carbamate (1.54 g, 4.8 mmol), ((prop-2-yn-1-yloxy)methyl)benzene (0.84 g, 5.8 mmol), bis(triphenylphosphine) palladium(II) chloride (0.17 g, 0.24 mmol), copper(I) iodide (0.09 g, 0.48 mmol), triethylamine (15 mL, 108 mmol) and DMF (5 mL). The mixture was degassed by bubbling nitrogen through for several minutes, the flask was sealed and the reaction mixture was stirred for 7 h. The mixture was diluted with EtOAc and washed with saturated ammonium chloride (2×) and brine (1×). The organics were dried over sodium sulfate, filtered and evaporated, and the crude material purified by silica gel chromatography, eluting with 12-100% EtOAc in hexanes, affording tert-butyl (4-(3-(benzyloxy)prop-1-yn-1-yl)pyridin-3-yl) carbamate (1.6 g, 98%). $^1$H NMR (400 MHz, CHLOROFORM-d) δ=9.44 (s, 1H), 8.28 (d, J=4.8 Hz, 1H), 7.45-7.33 (m, 5H), 7.26 (d, J=4.8 Hz, 1H), 7.14-6.93 (m, 1H), 4.71 (s, 2H), 4.50 (s, 2H), 1.56 (s, 9H).

Step B: 2-((benzyloxy)methyl)-1H-pyrrolo[2,3-c]pyridine

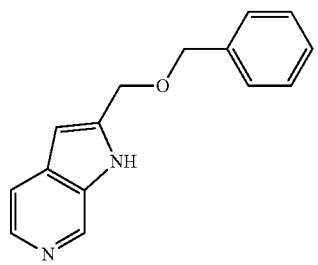 [SMILES: c1ccc(COCc2cc3ccncc3[nH]2)cc1]

A resealable pressure vessel was charged with tert-butyl (4-(3-(benzyloxy)prop-1-yn-1-yl)pyridin-3-yl)carbamate (1.6 g, 4.73 mmol), DBU (5 mL, 33.2 mmol), water (10 mL) and MeOH (30 mL). The vessel was sealed and heated on a 50° C. oil bath overnight. After reacting overnight, the mixture was concentrated on the rotovap to remove the methanol and then cooled on an ice bath. Water (20 mL) was added dropwise by addition funnel, at which point the product oiled out of the mixture giving a two-phase mixture. The aqueous portion was pipetted out of the flask, and during this process, the oil began to solidify. The oil was scraped with a spatula to aid in solidification, and then the combined fractions were filtered to collect the solids, washing with water. A tan solid was collected The HNMR showed that a small amt of DBU was retained in the product, but this was inconsequential and the material was carried on as-is: 2-((benzyloxy)methyl)-1H-pyrrolo[2,3-c]pyridine (1.09 g, 4.57 mmol, 97% yield). $^1$H NMR (400 MHz, DMSO-$d_6$) δ=8.70 (s, 1H), 8.08 (d, J=5.3 Hz, 1H), 7.57-7.19 (m, 7H), 6.49 (s, 1H), 4.73 (s, 2H), 4.65-4.50 (m, 2H).

Step C: tert-butyl 2-((benzyloxy)methyl)-1H-pyrrolo[2,3-c]pyridine-1-carboxylate

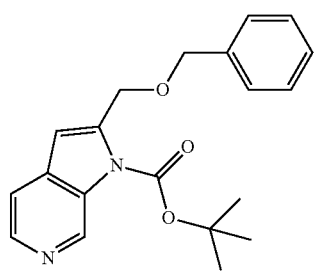 [SMILES: CC(C)(C)OC(=O)n1c(COCc2ccccc2)cc2ccncc21]

A flask was charged with 2-((benzyloxy)methyl)-1H-pyrrolo[2,3-c]pyridine (1.09 g, 4.57 mmol), di-tert-butyl dicarbonate (1.5 g, 6.9 mmol), TEA (1 mL, 7.2 mmol) and DCM (9 mL). The mixture was stirred at ambient temperature for 1 h, the solvent evaporated and the residue purified by silica gel chromatography (12-100% EtOAc/hexanes gradient) affording tert-butyl 2-((benzyloxy)methyl)-1H-pyrrolo[2,3-c]pyridine-1-carboxylate (0.95 g, 61% yield). ¹H NMR (400 MHz, CHLOROFORM-d) δ=9.35 (s, 1H), 8.40 (d, J=5.3 Hz, 1H), 7.53-7.31 (m, 6H), 6.77 (s, 1H), 4.98 (d, J=1.3 Hz, 2H), 4.74 (s, 2H), 1.71 (s, 9H).

Alternate Preparation: Tert-butyl 2-((benzyloxy)methyl)-1H-pyrrolo[2,3-c]pyridine-1-carboxylate was also prepared in an alternate preparation directly from tert-butyl tert-butyl (4-iodopyridin-3-yl)carbamate: In a sealed tube was added ((prop-2-yn-1-yloxy)methyl)benzene (104 µl, 0.750 mmol) and tert-butyl (4-iodopyridin-3-yl)carbamate (200 mg, 0.625 mmol) in DMF (625 µl). To this was added $PdCl_2(PPh_3)_2$ (21.93 mg, 0.031 mmol), copper(I) iodide (11.90 mg, 0.062 mmol) and TEA (1742 µl, 12.50 mmol). This reaction was then degassed for 15 minutes and then allowed to stir at 80° C. sealed. After 4 hours the reaction was complete. The reaction mixture was poured into ethyl acetate and saturated ammonium chloride. The organic was collected and washed several times with ammonium chloride. The organic was then purified on the biotage eluting in 10% ethyl acetate for 10 column volumes and then 10%-40% Ethyl acetate in hexanes over 10 column volumes. The product, tert-butyl 2-((benzyloxy)methyl)-1H-pyrrolo[2,3-c]pyridine-1-carboxylate (179 mg, 85% yield) was collected as a dark yellow oil. ¹H NMR (400 MHz, CHLOROFORM-d) δ=9.58-9.20 (m, 1H), 8.70-8.42 (m, 1H), 7.54-7.34 (m, 6H), 6.78 (s, 1H), 4.98 (d, J=1.3 Hz, 2H), 4.73 (s, 2H), 1.69 (s, 9H).

Step D: tert-butyl 2-(hydroxymethyl)octahydro-1H-pyrrolo[2,3-c]pyridine-1-carboxylate

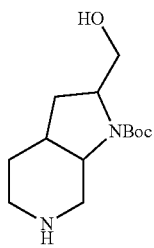

Tert-butyl 2-((benzyloxy)methyl)-1H-pyrrolo[2,3-c]pyridine-1-carboxylate (0.95 g, 2.8 mmol) in ethanol (50 mL) was added to 20% palladium hydroxide on carbon, 50% wet (0.50 g) in a 500 mL Parr bottle. The mixture was hydrogenated at 50 psi overnight. TLC and LC/MS show only partial conversion to first reduction product. An additional portion of 20% palladium hydroxide on carbon, 50% wet (0.28 g) was added along with acetic acid (10 mL). The bottle was recharged with $H_2$ to 55 psi and reacted for 3 days. The mixture was filtered to remove the $Pd(OH)_2$ and $PtO_2$ (~1 g) was added. Hydrogenation was continued 2 days more at which point complete conversion was seen. The catalyst was removed by filtration, and the filtrate was concentrated on the rotovap and carried on crude to the next step.

Step E: 6-benzyl 1-tert-butyl 2-(hydroxymethyl)hexahydro-1H-pyrrolo[2,3-c]pyridine-1,6(2H)-dicarboxylate

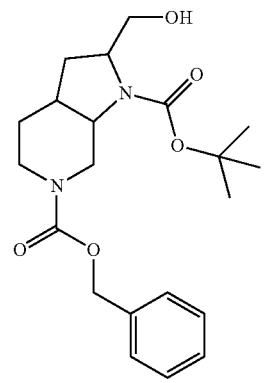 [SMILES: CC(C)(C)OC(=O)N1C(CO)CC2CCN(C(=O)OCc3ccccc3)CC21]

Tert-butyl 2-(hydroxymethyl)octahydro-1H-pyrrolo[2,3-c]pyridine-1-carboxylate, AcOH (0.9 g, 2.8 mmol) was dissolved in THF (14 mL) and 10% aqueous potassium carbonate solution (14 mL) and benzylchloroformate (0.84 mL, 5.9 mmol) was added. The biphasic mixture was stirred for 30 min, diluted with chloroform and the phases separated. The aqueous fraction was extracted twice again with chloroform and the combined organics dried over sodium sulfate. The crude mixture was purified by silica gel chromatography with an ethyl acetate/hexanes mixture (20%-100%). The title compound was obtained (0.85 g, 78%) and taken on to the next step.

Step F: 6-benzyl 1-tert-butyl 2-((tosyloxy)methyl)hexahydro-1H-pyrrolo[2,3-c]pyridine-1,6(2H)-dicarboxylate

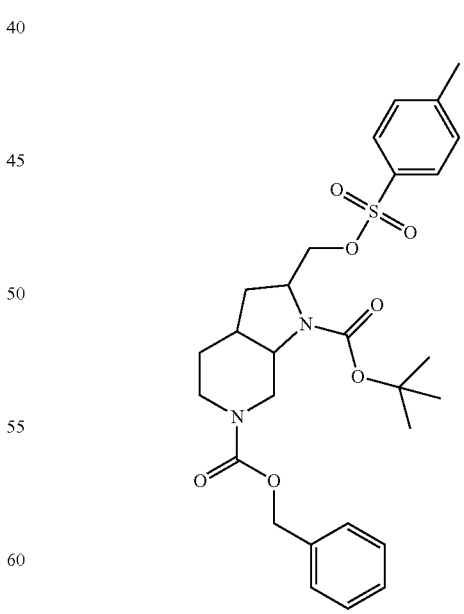

A flask was charged with 6-benzyl 1-tert-butyl 2-(hydroxymethyl)hexahydro-1H-pyrrolo[2,3-c]pyridine-1,6(2H)-dicarboxylate (0.85 g, 2.177 mmol) in Pyridine (6 ml) and cooled on ice bath. Ts-Cl (0.498 g, 2.61 mmol) was added, the ice bath removed and the mixture allowed to age overnight. Most of the solvent was evaporated and the residue was partitioned between EtOAc and 1N HCl and extracted 3× with EtOAc. wash with bicarb and brine. dry over sodium sulfate, filter, strip. Purify by biotage 6-50% EtOAc/Hex. Collect 6-benzyl 1-tert-butyl 2-((tosyloxy)methyl)hexahydro-1H-pyrrolo[2,3-c]pyridine-1,6(2H)-dicarboxylate (0.91 g, 1.671 mmol, 77% yield) LCMS shows correct mass, HNMR complex due to rotomers, but consistent. LCMS METHOD A: retention time=3.66 min, M+H=545.2.

Step G: tert-butyl hexahydro-2,6-methanopyrrolo[2,3-c]pyridine-1(2H)-carboxylate

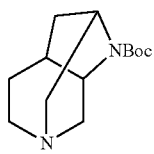

A 500 mL Parr bottle was charged with 6-benzyl 1-tert-butyl 2-((tosyloxy)methyl)hexahydro-1H-pyrrolo[2,3-c]pyridine-1,6(2H)-dicarboxylate (0.91 g, 1.67 mmol), 10% palladium on carbon (0.200 g, 0.1 mmol) and ethanol (40 mL). The mixture was hydrogenated at 50 psi on Parr shaker overnight. LC/MS shows complete cleavage of CBz. The mixture was filtered to remove the catalyst. To the filtrate, potassium carbonate (~1 g). The mixture was refluxed 3 h at which point TLC showed complete conversion to cyclized product. Most of the ethanol was evaporated and water was added. The mixture was extracted with chloroform (3×), dried over sodium sulfate, filtered and evaporated to afford tert-butyl hexahydro-2,6-methanopyrrolo[2,3-c]pyridine-1(2H)-carboxylate (0.28 g, 70% yield) as a clear oil. LCMS METHOD A: retention time=2.51 min (no UV signal at 220 nm), M+H=239.2. $^{1}$H NMR (400 MHz, CHLOROFORM-d) δ=4.10 (br. s., 2H), 3.40 (dd, J=8.2, 13.9 Hz, 2H), 2.80 (d, J=13.6 Hz, 4H), 2.65 (d, J=13.8 Hz, 1H), 2.16 (d, J=4.5 Hz, 1H), 1.83-1.62 (m, 3H), 1.54-1.40 (m, 9H).

Step H: (hexahydro-2,6-methanopyrrolo[2,3-c]pyridin-1(2H)-yl)(1H-indazol-3-yl)methanone

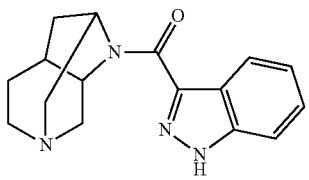 [SMILES: O=C(c1n[nH]c2ccccc12)N1C2CC3CCN(C2)CC31]

A solution of tert-butyl hexahydro-2,6-methanopyrrolo[2,3-c]pyridine-1(2H)-carboxylate (0.055 g, 0.23 mmol) in chloroform (1 mL) was treated with TFA (1 mL) and allowed to age for 30 min. and then evaporated. The residue was redissolved in DMF (1 mL), 1H-indazole-3-carboxylic acid (45 mg, 0.28 mmol), HATU (110 mg, 0.29 mmol) and DIPEA (0.2 mL, 1.15 mmol) were added. The mixture was allowed to stir at ambient temperature overnight. The solvent was removed by evaporation under a stream of nitrogen, and the residue was partitioned between chloroform and saturated aqueous sodium bicarbonate. The phases were separated and the aqueous fraction extracted twice more with chloroform. The combined organic phases were dried over sodium sulfate, filtered and the solvent was removed by evaporation on the rotovap. The resultant residue was purified by silica gel chromatography, eluting with a gradient from 5% to 40% (9:1 MeOH/NH4OH) in chloroform, affording the title compound (50 mg, 73%). LCMS METHOD A: retention time=2.40 min, M+H=283.3. $^{1}$H NMR (500 MHz, CHLOROFORM-d) δ=12.35 (br. s., 1H), 8.30 (dd, J=8.2, 10.7 Hz, 1H), 7.49-7.42 (m, 1H), 7.37 (t, J=7.3 Hz, 1H), 7.24 (t, J=7.6 Hz, 1H), 5.38-4.80 (m, 2H), 3.68-3.58 (m, 1H), 3.56-3.40 (m, 1H), 3.26-3.16 (m, 1H), 3.15-2.71 (m, 4H), 2.34-2.17 (m, 1H), 1.91-1.64 (m, 3H).

Example 2

(5-chloro-1H-indazol-3-yl)(hexahydro-2,6-methanopyrrolo[2,3-c]pyridin-1(2H)-yl)methanone

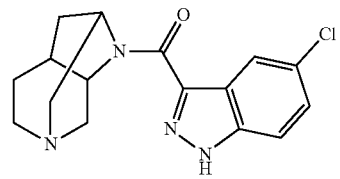 [SMILES: O=C(c1n[nH]c2ccc(Cl)cc12)N1C2CC3CCN(C2)CC31]

Step A:
octahydro-2,6-methanopyrrolo[2,3-c]pyridine, 2TFA

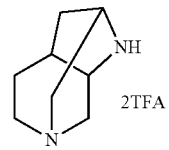

A solution of tert-butyl hexahydro-2,6-methanopyrrolo[2,3-c]pyridine-1(2H)-carboxylate (0.18 g, 0.76 mmol) in chloroform (9 mL) was treated with TFA (5 mL) and allowed to age for 1 h and then evaporated. The residue was azeotroped thrice with chloroform to remove residual TFA. The yield was assumed to be quantitative for the purposes of calculating stoichiometry for subsequent transformations, and the crude material was used without further purification.

Step B: (5-chloro-1H-indazol-3-yl)(hexahydro-2,6-methanopyrrolo[2,3-c]pyridin-1(2H)-yl)methanone

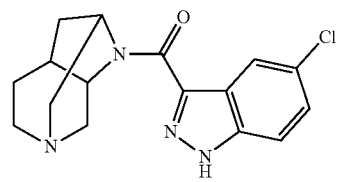 [SMILES: O=C(c1n[nH]c2ccc(Cl)cc12)N1C2CC3CCN(C2)CC31]

Octahydro-2,6-methanopyrrolo[2,3-c]pyridine, 2TFA (0.75 mmol), from Example 1, Step H, was dissolved in DMF (7.5 mL). Into a scintillation vial, 7.0 mL of this stock solution was placed along with DIPEA (0.61 mL, 3.5 mmol). In another scintillation vial, HATU (0.532 g, 1.4 mmol) was added and DMF (7.0 mL) and the mixture was sonicated to facilitate dissolution. To another vial, containing 5-chloro-1H-indazole-3-carboxylic acid (20 mg, 0.10 mmol), 0.5 mL of the HATU stock solution was added and the vial was shaken for 5 minutes, and then 0.5 mL of the amine/DIPEA stock solution was added and the vial was shaken overnight at ambient temperature. The reaction mixture was diluted with additional DMF to afford a total volume of 1.7 mL, and purified by preparative HPLC.

The crude material was purified via preparative LC/MS with the following conditions: Column: Waters XBridge C18, 19×200 mm, 5 μm particles; Guard Column: Waters XBridge C18, 19×10 mm, 5 μm particles; Mobile Phase A: water with 20-mM ammonium acetate; Mobile Phase B: 95:5 methanol:water with 20-mM ammonium acetate; Gradient: 35-65% B over 30 minutes, then a 5-minute hold at 100% B; Flow: 20 mL/min. Fractions containing the desired product were combined and dried via centrifugal evaporation. The yield of the product was 29.7 mg, and its estimated purity by LCMS analysis was 100%. Two analytical LC/MS injections were used to determine the final purity. Injection 1 conditions: Column: Waters BEH C18, 2.0×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7 μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. LCMS Retention time=3.07 min, M+H=317.11. Proton NMR was acquired in deuterated DMSO. $^1$H NMR (500 MHz, DMSO-$d_6$) δ=8.19-8.07 (m, 1H), 7.72-7.62 (m, 1H), 7.45 (dd, J=1.8, 8.9 Hz, 1H), 5.40-4.50 (m, 2H), 3.12-2.64 (m, 8H), 2.25-2.00 (m, 1H), 1.91-1.51 (m, 3H) (integration complicated by large water peak overlapping with some signals).

Example 3

(5-bromo-1H-indazol-3-yl)(hexahydro-2,6-methanopyrrolo[2,3-c]pyridin-1(2H)-yl)methanone

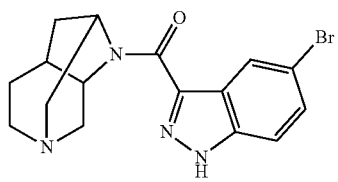 [SMILES: O=C(c1n[nH]c2ccc(Br)cc12)N1C2CC3CCN(C2)CC31]

Reacting 5-bromo-1H-indazole-3-carboxylic acid (24 mg, 0.10 mmol) according to the method of example 2, step B afforded (5-bromo-1H-indazol-3-yl)(hexahydro-2,6-methanopyrrolo[2,3-c]pyridin-1(2H)-yl)methanone. Purification conditions: Column: Waters XBridge C18, 19×200 mm, 5 μm particles; Guard Column: Waters XBridge C18, 19×10 mm, 5 μm particles; Mobile Phase A: water with 20-mM ammonium acetate; Mobile Phase B: 95:5 acetonitrile:water with 20-mM ammonium acetate; Gradient: 0-100% B over 20 minutes, then a 4-minute hold at 100% B; Flow: 25 mL/min. Fractions containing the desired product were combined and dried via centrifugal evaporation. The yield of the product was 13.5 mg, and its estimated purity by LCMS analysis was 100%. Two analytical LC/MS injections were used to determine the final purity. Injection 1 conditions: Column: Waters BEH C18, 2.0×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. LCMS Retention time=1.72 min, M+H=361.06. Injection 2 conditions: Column: Waters BEH C18, 2.0×50 mm, 1.7 μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Proton NMR was acquired in deuterated DMSO. $^1$H NMR (500 MHz, DMSO-$d_6$) δ=8.17-7.78 (m, 2H), 7.61 (dd, J=0.9, 7.6 Hz, 1H), 7.55-7.45 (m, 1H), 4.39-4.17 (m, 1H), 3.95-3.51 (m, 2H), 3.18 (d, J=11.3 Hz, 2H), 2.85-2.56 (m, 4H), 2.38 (d, J=3.7 Hz, 1H), 2.16 (br. s., 1H), 1.80-1.64 (m, 2H) (integration complicated by large water peak overlapping with some signals).

Example 4

(7-chlorobenzo[b]thiophen-2-yl)(hexahydro-2,6-methanopyrrolo[2,3-c]pyridin-1(2H)-yl)methanone

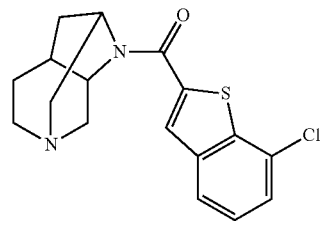 [SMILES: O=C(c1cc2cccc(Cl)c2s1)N1C2CC3CCN(C2)CC31]

Reacting 7-chlorobenzo[b]thiophene-2-carboxylic acid (21 mg, 0.10 mmol) according to the method of example 2, step B afforded (7-chlorobenzo[b]thiophen-2-yl)(hexahydro-2,6-methanopyrrolo[2,3-c]pyridin-1(2H)-yl)methanone. Purification conditions: The crude material was purified via preparative LC/MS with the following conditions: Column: Waters XBridge C18, 19×150 mm, 5 μm particles; Guard Column: Waters XBridge C18, 19×10 mm, 5 μm particles; Mobile Phase A: water with 20-mM ammonium acetate; Mobile Phase B: 95:5 methanol:water with 20-mM ammonium acetate; Gradient: 60-100% B over 10 minutes, then a 3-minute hold at 100% B; Flow: 20 mL/min. Fractions containing the desired product were combined and dried via centrifugal evaporation. The yield of the product was 6.8 mg, and its estimated purity by LCMS analysis was 100%. Two analytical LC/MS injections were used to determine the final purity. Injection 1 conditions: Column: Waters BEH C18, 2.0×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7 μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. LCMS Retention time=3.58 min, M+H=333.08. Proton NMR was acquired in deuterated DMSO. ¹H NMR (500 MHz, DMSO-d₆) δ=7.96 (dd, J=0.9, 7.9 Hz, 2H), 7.61 (dd, J=0.9, 7.9 Hz, 1H), 7.55-7.48 (m, 1H), 4.65-4.45 (m, 2H), 3.16-2.71 (m, 6H), 2.32-1.99 (m, 1H), 1.92-1.57 (m, 3H) (integration complicated by large water peak overlapping with some signals).

Example 5

Benzofuran-2-yl(hexahydro-2,6-methanopyrrolo[2,3-c]pyridin-1(2H)-yl)methanone

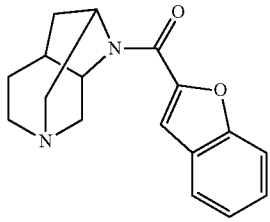 [SMILES: O=C(c1cc2ccccc2o1)N1C2CC3CCN(C2)CC31]

Reacting benzofuran-2-carboxylic acid (16 mg, 0.10 mmol) according to the method of example 2, step B afforded benzofuran-2-yl(hexahydro-2,6-methanopyrrolo[2,3-c]pyridin-1(2H)-yl)methanone Purification conditions: Column: Waters XBridge C18, 19×200 mm, 5 μm particles; Guard Column: Waters XBridge C18, 19×10 mm, 5 μm particles; Mobile Phase A: water with 20-mM ammonium acetate; Mobile Phase B: 95:5 methanol:water with 20-mM ammonium acetate; Gradient: 30-60% B over 30 minutes, then a 5-minute hold at 100% B; Flow: 20 mL/min. Fractions containing the desired product were combined and dried via centrifugal evaporation. The yield of the product was 13.1 mg, and its estimated purity by LCMS analysis was 100%. Two analytical LC/MS injections were used to determine the final purity. Injection 1 conditions: Column: Waters BEH C18, 2.0×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7 μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. LCMS Retention time=2.98 min, M+H=283.14. Proton NMR was acquired in deuterated DMSO. ¹H NMR (500 MHz, DMSO-d₆) δ=7.77 (d, J=7.6 Hz, 1H), 7.69 (d, J=8.2 Hz, 1H), 7.52 (s, 1H), 7.48 (ddd, J=1.2, 7.2, 8.3 Hz, 1H), 7.36 (dt, J=0.9, 7.6 Hz, 1H), 5.00-4.51 (m, 2H), 3.25-2.68 (m, 6H), 1.92 (s, 4H) (integration complicated by large water peak overlapping with some signals).

Example 6

Benzo[b]thiophen-2-yl(hexahydro-2,6-methanopyrrolo[2,3-c]pyridin-1(2H)-yl)methanone

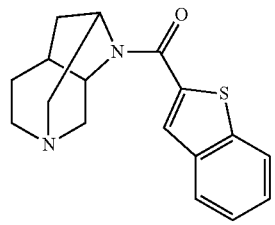 [SMILES: O=C(c1cc2ccccc2s1)N1C2CC3CCN(C2)CC31]

Reacting benzo[b]thiophene-2-carboxylic acid (18 mg, 0.10 mmol) according to the method of example 2, step B afforded Benzo[b]thiophen-2-yl(hexahydro-2,6-methanopyrrolo[2,3-c]pyridin-1(2H)-yl)methanone. Purification conditions: The crude material was purified via preparative LC/MS with the following conditions: Column: Waters XBridge C18, 19×200 mm, 5 μm particles; Guard Column: Waters XBridge C18, 19×10 mm, 5 μm particles; Mobile Phase A: water with 20-mM ammonium acetate; Mobile Phase B: 95:5 methanol:water with 20-mM ammonium acetate; Gradient: 30-60% B over 30 minutes, then a 5-minute hold at 100% B; Flow: 20 mL/min. Fractions containing the desired product were combined and dried via centrifugal evaporation. The yield of the product was 13.1 mg, and its estimated purity by LCMS analysis was 100%. Two analytical LC/MS injections were used to determine the final purity. Injection 1 conditions: Column: Waters BEH C18, 2.0×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7 μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. LCMS Retention time=3.12 min, M+H=299.11. Proton NMR was acquired in deuterated DMSO. ¹H NMR (500 MHz, DMSO-d₆) δ=8.08-8.01 (m, 1H), 7.99-7.93 (m, 1H), 7.86 (br. s., 1H), 7.52-7.42 (m, 2H), 4.65-4.51 (m, 2H), 3.23-2.61 (m, 7H), 2.26-2.03 (m, 1H), 1.87-1.57 (m, 2H) (integration complicated by large water peak overlapping with some signals).

Example 7

(6-chloro-1H-indazol-3-yl)(hexahydro-2,6-methanopyrrolo[2,3-c]pyridin-1(2H)-yl)methanone

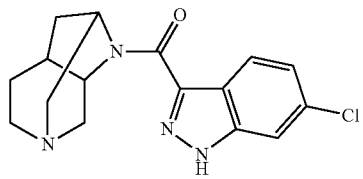 [SMILES: O=C(c1n[nH]c2cc(Cl)ccc12)N1C2CC3CCN(C2)CC31]

Reacting 6-chloro-1H-indazole-3-carboxylic acid (20 mg, 0.10 mmol), according to the method of example 2, step B afforded (6-chloro-1H-indazol-3-yl)(hexahydro-2,6-methanopyrrolo[2,3-c]pyridin-1(2H)-yl)methanone. Purification conditions: Column: Waters XBridge C18, 19×150 mm, 5 µm particles; Guard Column: Waters XBridge C18, 19×10 mm, 5 µm particles; Mobile Phase A: water with 20-mM ammonium acetate; Mobile Phase B: 95:5 methanol:water with 20-mM ammonium acetate; Gradient: 50-100% B over 10 minutes, then a 3-minute hold at 100% B; Flow: 20 mL/min. Fractions containing the desired product were combined and dried via centrifugal evaporation. The yield of the product was 4.3 mg, and its estimated purity by LCMS analysis was 97%. Two analytical LC/MS injections were used to determine the final purity. Injection 1 conditions: Column: Waters BEH C18, 2.0×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7 µm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. LCMS Retention time=3.07 min, M+H=317.11. Proton NMR was acquired in deuterated DMSO. $^1$H NMR (500 MHz, DMSO-$d_6$) δ=8.20-8.06 (m, 1H), 7.71 (td, J=0.9, 1.8 Hz, 1H), 7.33-7.17 (m, 1H), 5.32-5.02 (m, 1H), 4.72-4.46 (m, 1H), 3.27-2.67 (m, 9H), 2.24-1.98 (m, 1H), 1.80-1.53 (m, 2H) (integration complicated by large water peak overlapping with some signals).

Example 8

(Hexahydro-2,6-methanopyrrolo[2,3-c]pyridin-1 (2H)-yl)(1-methyl-1H-indazol-3-yl)methanone

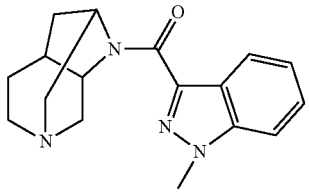 [SMILES: Cn1nc(C(=O)N2C3CC4CCN(C3)CC42)c2ccccc21]

Reacting 1-methyl-1H-indazole-3-carboxylic acid (18 mg, 0.10 mmol), according to the method of example 2, step B afforded hexahydro-2,6-methanopyrrolo[2,3-c]pyridin-1 (2H)-yl)(1-methyl-1H-indazol-3-yl)methanone. Purification conditions: Column: Waters XBridge C18, 19×200 mm, 5 µm particles; Guard Column: Waters XBridge C18, 19×10 mm, 5 µm particles; Mobile Phase A: water with 20-mM ammonium acetate; Mobile Phase B: 95:5 methanol:water with 20-mM ammonium acetate; Gradient: 20-50% B over 30 minutes, then a 5-minute hold at 100% B; Flow: 20 mL/min. Fractions containing the desired product were combined and dried via centrifugal evaporation. The material was further purified via preparative LC/MS with the following conditions: Column: Waters XBridge C18, 19×200 mm, 5 µm particles; Guard Column: Waters XBridge C18, 19×10 mm, 5-µm particles; Mobile Phase A: water with 20-mM ammonium acetate; Mobile Phase B: 95:5 methanol:water with 20-mM ammonium acetate; Gradient: 20-50% B over 30 minutes, then a 5-minute hold at 100% B; Flow: 20 mL/min. Fractions containing the desired product were combined and dried via centrifugal evaporation. The yield of the product was 8.2 mg, and its estimated purity by LCMS analysis was 100%. Two analytical LC/MS injections were used to determine the final purity. Injection 1 conditions: Column: Waters BEH C18, 2.0×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7 µm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. LCMS Retention time=2.76 min, M+H=296.16. Proton NMR was acquired in deuterated DMSO. $^1$H NMR (500 MHz, DMSO-$d_6$) δ=8.20-8.05 (m, 1H), 7.73 (d, J=8.5 Hz, 1H), 7.48 (dt, J=0.9, 7.6 Hz, 1H), 7.26 (t, J=7.5 Hz, 1H), 5.30-5.06 (m, 1H), 4.67-4.50 (m, 1H), 4.16-4.06 (m, 3H), 3.14-2.69 (m, 6H), 2.25-2.04 (m, 1H), 1.96-1.85 (m, 1H), 1.82-1.50 (m, 2H) (integration complicated by large water peak overlapping with some signals).

Example 9

(6-methoxy-1H-indazol-3-yl)(hexahydro-2,6-methanopyrrolo[2,3-c]pyridin-1(2H)-yl)methanone

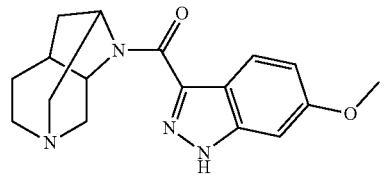 [SMILES: COc1ccc2c(C(=O)N3C4CC5CCN(C4)CC53)n[nH]c2c1]

Reacting 6-methoxy-1H-indazole-3-carboxylic acid (19 mg, 0.10 mmol), according to the method of example 2, step B afforded (6-methoxy-1H-indazol-3-yl)(hexahydro-2,6-methanopyrrolo[2,3-c]pyridin-1(2H)-yl)methanone. Purification conditions: Column: Waters XBridge C18, 19×200 mm, 5 µm particles; Guard Column: Waters XBridge C18, 19×10 mm, 5 µm particles; Mobile Phase A: water with 20-mM ammonium acetate; Mobile Phase B: 95:5 methanol:water with 20-mM ammonium acetate; Gradient: 30-60% B over 30 minutes, then a 5-minute hold at 100% B; Flow: 20 mL/min. Fractions containing the desired product were combined and dried via centrifugal evaporation. The yield of the product was 13.1 mg, and its estimated purity by LCMS analysis was 100%. Two analytical LC/MS injections were used to determine the final purity. Injection 1 conditions: Column: Waters BEH C18, 2.0×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7 µm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. LCMS Retention time 2.65 min, M+H=313.16. Proton NMR was acquired in deuterated DMSO. $^1$H NMR (500 MHz, DMSO-$d_6$) δ=13.36-13.18 (m, 1H), 8.06-7.88 (m, 1H), 7.03-6.92 (m, 1H), 6.85 (dd, J=2.1, 8.9 Hz, 1H), 5.30-4.97 (m, 1H), 4.68-4.46 (m, 1H), 3.84 (s, 3H), 3.09-2.65 (m, 7H), 2.20-1.97 (m, 1H), 1.80-1.51 (m, 2H) (integration complicated by large water peak overlapping with some signals).

Example 10

(5-methoxy-1H-indazol-3-yl)(hexahydro-2,6-methanopyrrolo[2,3-c]pyridin-1(2H)-yl)methanone

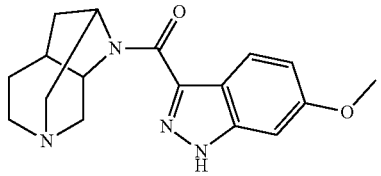 [SMILES: COc1ccc2c(C(=O)N3C4CC5CCN(C4)CC53)n[nH]c2c1]

Reacting 5-methoxy-1H-indazole-3-carboxylic acid (19 mg, 0.10 mmol), according to the method of example 2, step B afforded (5-methoxy-1H-indazol-3-yl)(hexahydro-2,6-methanopyrrolo[2,3-c]pyridin-1(2H)-yl)methanone. Purification conditions: Column: Waters XBridge C18, 19×150 mm, 5 μm particles; Guard Column: Waters XBridge C18, 19×10 mm, 5 μm particles; Mobile Phase A: water with 20-mM ammonium acetate; Mobile Phase B: 95:5 methanol:water with 20-mM ammonium acetate; Gradient: 10-100% B over 15 minutes, then a 3-minute hold at 100% B; Flow: 20 mL/min. Fractions containing the desired product were combined and dried via centrifugal evaporation. The yield of the product was 15.6 mg, and its estimated purity by LCMS analysis was 95%. Two analytical LC/MS injections were used to determine the final purity. Injection 1 conditions: Column: Waters BEH C18, 2.0×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. LCMS Retention time 1.21 min, M+H=313.16. Injection 2 conditions: Column: Waters BEH C18, 2.0×50 mm, 1.7 μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Proton NMR was acquired in deuterated DMSO. $^1$H NMR (500 MHz, DMSO-$d_6$) δ=8.64 (s, 1H), 7.35 (d, J=2.7 Hz, 1H), 7.31-7.26 (m, 1H), 7.25-7.20 (m, 1H), 4.20-4.09 (m, 2H), 3.80 (s, 3H), 2.90 (s, 3H), 2.75 (s, 3H), 2.17-2.07 (m, 1H), 1.88-1.54 (m, 3H) (integration complicated by large water peak overlapping with some signals).

Example 11

Benzo[d]isothiazol-3-yl(hexahydro-2,6-methanopyrrolo[2,3-c]pyridin-1(2H)-yl)methanone

Reacting benzo[d]isothiazole-3-carboxylic acid (18 mg, 0.10 mmol), according to the method of example 2, step B afforded Benzo[d]isothiazol-3-yl(hexahydro-2,6-methanopyrrolo[2,3-c]pyridin-1(2H)-yl)methanone. Purification conditions: Column: Waters XBridge C18, 19×150 mm, 5-μm particles; Guard Column: Waters XBridge C18, 19×10 mm, 5 μm particles; Mobile Phase A: water with 20-mM ammonium acetate; Mobile Phase B: 95:5 methanol:water with 20-mM ammonium acetate; Gradient: 40-100% B over 11 minutes, then a 3-minute hold at 100% B; Flow: 20 mL/min. Fractions containing the desired product were combined and dried via centrifugal evaporation. The yield of the product was 8.4 mg, and its estimated purity by LCMS analysis was 99%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. LCMS Retention time 2.97 min, M+H=300.11. Proton NMR was acquired in deuterated DMSO. $^1$H NMR (500 MHz, DMSO-$d_6$) δ=8.47-8.36 (m, 1H), 8.33 (d, J=8.2 Hz, 1H), 7.73-7.67 (m, 1H), 7.64-7.55 (m, 1H), 4.97-4.65 (m, 2H), 3.70-3.49 (m, 1H), 3.19-2.64 (m, 2H), 1.92 (s, 5H) (integration complicated by large water peak overlapping with some signals).

Example 12

(4-chlorobenzo[b]thiophen-2-yl)(hexahydro-2,6-methanopyrrolo[2,3-c]pyridin-1(2H)-yl)methanone

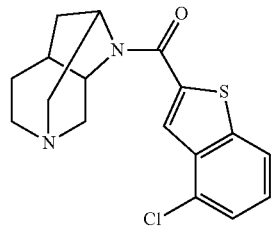 [SMILES: O=C(c1cc2c(Cl)cccc2s1)N1C2CC3CCN(C2)CC31]

Reacting 4-chlorobenzo[b]thiophene-2-carboxylic acid (21 mg, 0.10 mmol) according to the method of example 2, step B afforded (4-chlorobenzo[b]thiophen-2-yl)(hexahydro-2,6-methanopyrrolo[2,3-c]pyridin-1(2H)-yl)methanone. Purification conditions: Column: Waters XBridge C18, 19×150 mm, 5 μm particles; Guard Column: Waters XBridge C18, 19×10 mm, 5 μm particles; Mobile Phase A: water with 20-mM ammonium acetate; Mobile Phase B: 95:5 methanol:water with 20-mM ammonium acetate; Gradient: 60-100% B over 10 minutes, then a 3-minute hold at 100% B; Flow: 20 mL/min. Fractions containing the desired product were combined and dried via centrifugal evaporation. The yield of the product was 6.5 mg, and its estimated purity by LCMS analysis was 100%. Two analytical LC/MS injections were used to determine the final purity. Injection 1 conditions: Column: Waters BEH C18, 2.0×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7 μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. LCMS Retention time 3.54 min, M+H=333.08. Proton NMR was acquired in deuterated DMSO. $^1$H NMR (500 MHz, DMSO-d$_6$) δ=8.09-8.02 (m, 1H), 7.73 (br. s., 1H), 7.56 (dd, J=0.9, 7.6 Hz, 1H), 7.53-7.45 (m, 1H), 4.58-4.38 (m, 2H), 3.29-2.60 (m, 7H), 2.29-1.98 (m, 1H), 1.90-1.52 (m, 3H) (integration complicated by large water peak overlapping with some signals).

Example 13

(4-chlorophenyl)(hexahydro-2,6-methanopyrrolo[2,3-c]pyridin-1(2H)-yl)methanone

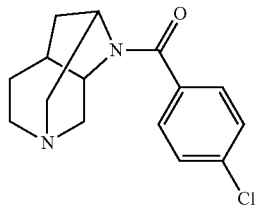 [SMILES: O=C(c1ccc(Cl)cc1)N1C2CC3CCN(C2)CC31]

Reacting 4-chlorobenzoic acid (16 mg, 0.10 mmol) according to the method of example 2, step B afforded (4-chlorophenyl)(hexahydro-2,6-methanopyrrolo[2,3-c]pyridin-1(2H)-yl)methanone. Purification conditions: Column: Waters XBridge C18, 19×150 mm, 5 μm particles; Guard Column: Waters XBridge C18, 19×10 mm, 5 μm particles; Mobile Phase A: water with 20-mM ammonium acetate; Mobile Phase B: 95:5 methanol:water with 20-mM ammonium acetate; Gradient: 40-100% B over 11 minutes, then a 3-minute hold at 100% B; Flow: 20 mL/min. Fractions containing the desired product were combined and dried via centrifugal evaporation.

The material was further purified via preparative LC/MS with the following conditions: Column: Waters XBridge C18, 19×200 mm, 5 μm particles; Guard Column: Waters XBridge C18, 19×10 mm, 5 μm particles; Mobile Phase A: water with 20-mM ammonium acetate; Mobile Phase B: 95:5 methanol:water with 20-mM ammonium acetate; Gradient: 20-50% B over 30 minutes, then a 5-minute hold at 100% B; Flow: 20 mL/min. Fractions containing the desired product were combined and dried via centrifugal evaporation. The yield of the product was 4.3 mg, and its estimated purity by LCMS analysis was 100%. Two analytical LC/MS injections were used to determine the final purity. Injection 1 conditions: Column: Waters BEH C18, 2.0×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. LCMS Retention time 1.52 min, M+H=277.10. Injection 2 conditions: Column: Waters BEH C18, 2.0×50 mm, 1.7 μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Proton NMR was acquired in deuterated DMSO. $^1$H NMR (500 MHz, DMSO-d$_6$) δ=7.56-7.49 (m, 4H), 4.56-4.45 (m, 1H), 3.97-3.82 (m, 1H), 3.25-2.61 (m, 7H), 2.23-2.00 (m, 1H), 1.88-1.58 (m, 3H) (integration complicated by large water peak overlapping with some signals).

Example 14

(Hexahydro-2,6-methanopyrrolo[2,3-c]pyridin-1(2H)-yl)(1-methyl-1H-indol-3-yl)methanone

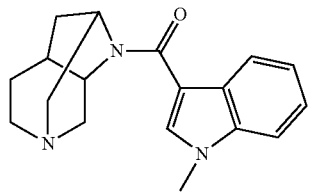 [SMILES: Cn1cc(C(=O)N2C3CC4CCN(C3)CC42)c2ccccc21]

Reacting 1-methyl-1H-indole-3-carboxylic acid (18 mg, 0.10 mmol), according to the method of example 2, step B afforded hexahydro-2,6-methanopyrrolo[2,3-c]pyridin-1(2H)-yl)(1-methyl-1H-indol-3-yl)methanone. Purification conditions: Column: Waters XBridge C18, 19×200 mm, 5 μm particles; Guard Column: Waters XBridge C18, 19×10 mm, 5-μm particles; Mobile Phase A: water with 20-mM ammonium acetate; Mobile Phase B: 95:5 methanol:water with 20-mM ammonium acetate; Gradient: 20-50% B over 30 minutes, then a 5-minute hold at 100% B; Flow: 20 mL/min. Fractions containing the desired product were combined and dried via centrifugal evaporation. The material was further purified via preparative LC/MS with the following conditions: Column: Waters XBridge Shield RP18, 19×200 mm, 5-μm particles; Guard Column: Waters XBridge C18, 19×10 mm, 5 μm particles; Mobile Phase A: water; Mobile Phase B: methanol; Buffer: 20-mM ammonium acetate; Gradient: 30-95% B over 19.5 minutes, then a 14.0 minute hold at 95% B; Flow: 20 mL/min. Fractions containing the desired product were combined and dried via centrifugal evaporation. The yield of the product was 6.2 mg, and its estimated purity by LCMS analysis was 100%.

Two analytical LC/MS injections were used to determine the final purity. Injection 1 conditions: Column: Waters BEH C18, 2.0×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. LCMS Retention time 2.69 min, M+H=296.17. Proton NMR was acquired in deuterated DMSO. $^1$H NMR (500 MHz, DMSO-$d_6$) δ=7.82-7.73 (m, 2H), 7.49 (d, J=8.2 Hz, 1H), 7.23 (d, J=1.2 Hz, 1H), 7.15 (dt, J=1.1, 7.6 Hz, 1H), 4.45-4.23 (m, 2H), 3.84 (s, 3H), 3.27-3.18 (m, 2H), 3.06-2.95 (m, 1H), 2.82 (s, 2H), 2.73-2.62 (m, 2H), 2.18-2.04 (m, 1H), 1.82 (d, J=12.2 Hz, 1H), 1.75-1.47 (m, 2H) (integration complicated by large water peak overlapping with some signals).

Example 15

(4-methoxy-1H-indazol-3-yl)(hexahydro-2,6-methanopyrrolo[2,3-c]pyridin-1(2H)-yl)methanone

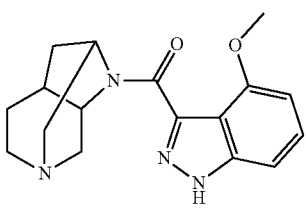 [SMILES: COc1cccc2[nH]nc(C(=O)N3C4CC5CCN(C4)CC53)c12]

Reacting 4-methoxy-1H-indazole-3-carboxylic acid (19 mg, 0.10 mmol), according to the method of example 2, step B afforded (4-methoxy-1H-indazol-3-yl)(hexahydro-2,6-methanopyrrolo[2,3-c]pyridin-1(2H)-yl)methanone. Purification conditions: Column: Waters XBridge C18, 19×150 mm, 5 μm particles; Guard Column: Waters XBridge C18, 19×10 mm, 5 μm particles; Mobile Phase A: water with 20-mM ammonium acetate; Mobile Phase B: 95:5 methanol:water with 20-mM ammonium acetate; Gradient: 30-100% B over 13 minutes, then a 3-minute hold at 100% B; Flow: 20 mL/min. Fractions containing the desired product were combined and dried via centrifugal evaporation. The material was further purified via preparative LC/MS with the following conditions: Column: Waters XBridge C18, 19×200 mm, 5 μm particles; Guard Column: Waters XBridge C18, 19×10 mm, 5-μm particles; Mobile Phase A: water with 20-mM ammonium acetate; Mobile Phase B: 95:5 methanol:water with 20-mM ammonium acetate; Gradient: 15-45% B over 30 minutes, then a 5-minute hold at 100% B; Flow: 20 mL/min. Fractions containing the desired product were combined and dried via centrifugal evaporation. The material was further purified via preparative LC/MS with the following conditions: Column: Waters XBridge C18, 19×150 mm, 5-μm particles; Guard Column: Waters XBridge C18, 19×10 mm, 5-μm particles; Mobile Phase A: water with 20-mM ammonium acetate; Mobile Phase B: 95:5 methanol:water with 20-mM ammonium acetate; Gradient: 30-100% B over 30 minutes, then a 5-minute hold at 100% B; Flow: 20 mL/min. Fractions containing the desired product were combined and dried via centrifugal evaporation. The yield of the product was 2.7 mg, and its estimated purity by LCMS analysis was 99%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. LCMS Retention time 2.39 min, M+H=313.16. Proton NMR was acquired in deuterated DMSO. $^1$H NMR (500 MHz, DMSO-$d_6$) δ=13.27-13.15 (m, 1H), 7.36-7.25 (m, 1H), 7.11 (dd, J=2.9, 8.1 Hz, 1H), 6.59 (dd, J=1.4, 7.5 Hz, 1H), 4.58-4.40 (m, 1H), 3.86 (s, 3H), 3.57-3.48 (m, 1H), 3.23 (br. s., 4H), 2.78 (s, 1H), 2.69-2.57 (m, 1H), 2.18-2.03 (m, 1H), 1.80-1.46 (m, 3H) (integration complicated by large water peak overlapping with some signals).

Example 16

(6-chloro-1H-indazol-3-yl)((2R,3aR,6S,7aS)-hexahydro-2,6-methanopyrrolo[2,3-c]pyridin-1(2H)-yl)methanone

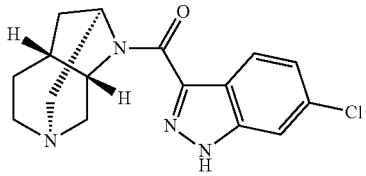 [SMILES: O=C(c1n[nH]c2cc(Cl)ccc12)N1[C@@H]2C[C@H]3CC[N@@](C2)C[C@H]31]

Step A: (R)-tert-butyl 2-((benzyloxy)methyl)-2,3-dihydro-1H-pyrrolo[2,3-c]pyridine-1-carboxylate, (S)-tert-butyl 2-((benzyloxy)methyl)-2, 3-dihydro-1H-pyrrolo[2,3-c]pyridine-1-carboxylate

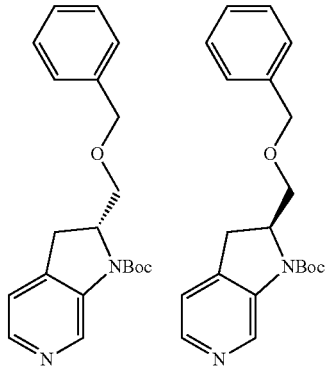 [SMILES: CC(C)(C)OC(=O)N1c2cnccc2C[C@@H]1COCc1ccccc1 ; CC(C)(C)OC(=O)N1c2cnccc2C[C@H]1COCc1ccccc1]

Tert-butyl 2-((benzyloxy)methyl)-1H-pyrrolo[2,3-c]pyridine-1-carboxylate (1.6 g, 4.73 mmol) in ethanol (30 mL) was added to 20% palladium hydroxide on carbon, 50% wet (0.16 g) in a 500 mL Parr bottle. The mixture was hydrogenated at 50 psi overnight. The catalyst was removed by filtration, and the filtrate was concentrated on the rotovap and the enantiomers were separated by chiral preparative SFC. Chromatography conditions: Chiralpak AD-H column, 30×25 mm, 5 um, Mobile Phase: 15% MeOH with 0.1% DEA in C02, temp: 35° C., Pressure: 150 bar, flow rate: 70 mL/min for 10 min, UV monitored at 250 nm, injection: ~1 mL of a 30 mg/mL solution in MeOH. Two peaks were collected: Peak 1 (believed to be (R)-tert-butyl 2-((benzyloxy)methyl)-2,3-dihydro-1H-pyrrolo[2,3-c]pyridine-1-carboxylate), 462 mg; peak 2 (believed to be (S)-tert-butyl 2-((benzyloxy)methyl)-2,3-dihydro-1H-pyrrolo[2,3-c]pyridine-1-carboxylate), 501 mg. Peak 1: LCMS METHOD A: retention time=3.86 min, M+H=341.2.

$^1$H NMR (400 MHz, DMSO-$d_6$) δ=8.73 (br. s., 1H), 8.17 (d, J=4.8 Hz, 1H), 7.38-7.25 (m, 5H), 7.23-7.18 (m, 2H), 4.48 (d, J=2.8 Hz, 3H), 3.68-3.56 (m, 2H), 3.37 (dd, J=10.0, 17.6 Hz, 1H), 3.05 (d, J=2.5 Hz, 1H), 1.49 (br. s., 9H).

Step B: (2R,3aR,7aS)-tert-butyl 2-(hydroxymethyl)octahydro-1H-pyrrolo[2,3-c]pyridine-1-carboxylate, AcOH

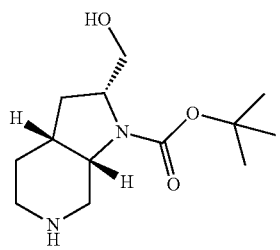 [SMILES: CC(C)(C)OC(=O)N1[C@@H](CO)C[C@H]2CCNC[C@H]21]

Tert-butyl 2-((benzyloxy)methyl)-1H-pyrrolo[2,3-c]pyridine-1-carboxylate (0.46 g, 1.35 mmol) in ethanol (20 mL) and acetic acid (2 mL) was added to 20% palladium hydroxide on carbon, 50% wet (0.05 g) in a 500 mL Parr bottle. The mixture was hydrogenated at 50 psi overnight. The catalyst was removed by filtration, and the filtrate was concentrated on the rotovap and carried on crude to the next step.

Step C: (2R,3aR,7aS)-6-benzyl 1-tert-butyl 2-(hydroxymethyl)hexahydro-1H-pyrrolo[2,3-c]pyridine-1,6(2H)-dicarboxylate

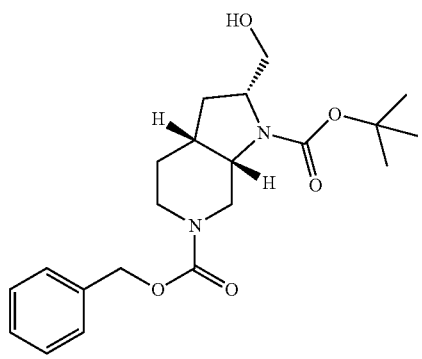 [SMILES: CC(C)(C)OC(=O)N1[C@@H](CO)C[C@H]2CCN(C(=O)OCc3ccccc3)C[C@H]21]

A flask was charged with (2R,3aR,7aS)-tert-butyl 2-(hydroxymethyl)octahydro-1H-pyrrolo[2,3-c]pyridine-1-carboxylate, AcOH (337 mg, 1.315 mmol), THF (10 mL) and 10% aqueous potassium carbonate (10 mL, 7.24 mmol), and CBZ-Cl (0.188 mL, 1.315 mmol) was added. The reaction was allowed to stir overnight and then poured into chloroform and water. The organic phase was collected and concentrated to residue. This was purified on the biotage eluting in 10%-100% ethyl acetate in hexanes. The product was collected and carried on to the next step.

Step D: (2R,3aR,7aS)-6-benzyl 1-tert-butyl 2-((tosyloxy)methyl)hexahydro-1H-pyrrolo[2,3-c]pyridine-1,6(2H)-dicarboxylate

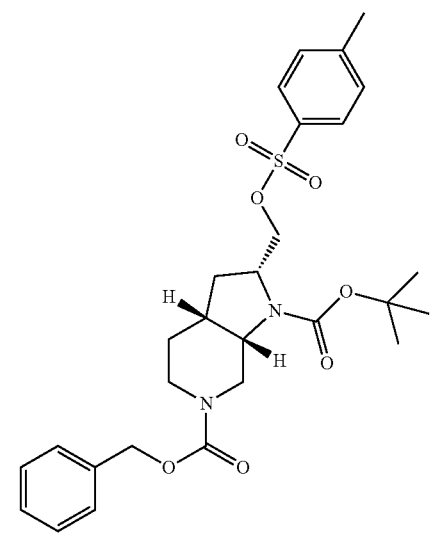 [SMILES: Cc1ccc(S(=O)(=O)OC[C@H]2C[C@H]3CCN(C(=O)OCc4ccccc4)C[C@H]3N2C(=O)OC(C)(C)C)cc1]

A flask was charged with (2R,3aR,7aS)-6-benzyl 1-tert-butyl 2-(hydroxymethyl)hexahydro-1H-pyrrolo[2,3-c]pyridine-1,6(2H)-dicarboxylate (310 mg, 0.79 mmol), and TsCl (151 mg, 0.794 mmol) in Pyridine (2 mL). The reaction mixture was then allowed to stir overnight. The reaction mixture was then diluted with toluene and concentrated to residue. The residue was then purified on Biotage eluting in 10%-100% ethyl acetate in hexanes. The product was collected and used in the next step. LCMS METHOD A: retention time=3.78 min, M+H=545.3.

Step E: (2R,3aR,6S,7aS)-tert-butyl hexahydro-2,6-methanopyrrolo[2,3-c]pyridine-1(2H)-carboxylate

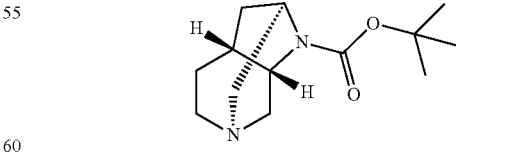

In a Parr bottle was added (2R,3aR,7aS)-6-benzyl 1-tert-butyl 2-((tosyloxy)methyl)hexahydro-1H-pyrrolo[2,3-c]pyridine-1,6(2H)-dicarboxylate (430 mg, 0.789 mmol) and 10% palladium on carbon (84 mg, 0.789 mmol) in ethanol (10 mL). This was placed on the Parr apparatus at 55 PSI for 24 hours. The reaction was removed, filtered through celtie and then the mother liquors were treated with potassium carbonate (109 mg, 0.789 mmol) and the reaction was heated to 70° C. for 2 hours. The reaction mixture was cooled to room temperature and concentrated to residue. The residue was purified on the Biotage eluting in 10%-40% (10% NH₄OH/methanol) in chloroform, affording (2R,3aR,6S,7aS)-tert-butyl hexahydro-2,6-methanopyrrolo[2,3-c]pyridine-1(2H)-carboxylate (0.186 g, 99% yield) LCMS METHOD A: retention time=1.47 min (no UV signal at 220 nm), M+H=239.3.

Step F: (6-chloro-1H-indazol-3-yl)((2R,3aR,6S,7aS)-hexahydro-2,6-methanopyrrolo[2,3-c]pyridin-1(2H)-yl)methanone

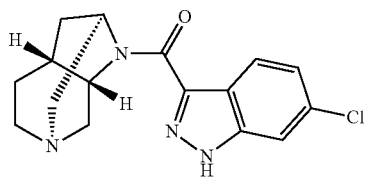 [SMILES: O=C(c1n[nH]c2cc(Cl)ccc12)N1[C@@H]2C[C@H]3CC[N@@](C2)C[C@H]31]

A flask was charged with (2R,3aR,6S,7aS)-tert-butyl hexahydro-2,6-methanopyrrolo[2,3-c]pyridine-1(2H)-carboxylate (50 mg, 0.210 mmol) and DCM (1 mL). This was treated with TFA (1 mL, 12.98 mmol) and the reaction was stirred for 2 hours. The reaction was then concentrated to residue and then taken up in DMF (1.000 mL) and treated with HATU (80 mg, 0.210 mmol), DIPEA (0.147 mL, 0.839 mmol) and with 6-chloro-1H-indazole-3-carboxylic acid (41.2 mg, 0.210 mmol). The reaction mixture was stirred overnight and then poured into chloroform and water. The organic was collected and the water layer was re-extracted with chloroform/methanol. The combined organics were purified on the Biotage eluting with 10%(10% NH₄OH/Methanol) in chloroform, affording (6-chloro-1H-indazol-3-yl)((2R,3aR,6S,7aS)-hexahydro-2,6-methanopyrrolo[2,3-c]pyridin-1(2H)-yl)methanone (20.1 mg, 29% yield). LCMS METHOD B: retention time=0.85 min, M+H=317.05. ¹H NMR (400 MHz, CHLOROFORM-d) δ=8.24 (d, J=8.3 Hz, 1H), 7.51 (s, 1H), 7.25 (dd, J=1.6, 8.7 Hz, 1H), 5.38-5.14 (m, 2H), 4.94-4.77 (m, 1H), 3.65-3.45 (m, 2H), 3.24-2.79 (m, 5H), 2.40-2.19 (m, 1H), 1.89 (d, J=12.8 Hz, 2H), 1.82-1.68 (m, 1H).

Example 17

(6-chloro-1H-indazol-3-yl)((2S,3aS,6R,7aR)-hexahydro-2,6-methanopyrrolo[2,3-c]pyridin-1(2H)-yl)methanone

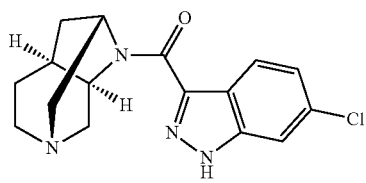 [SMILES: O=C(c1n[nH]c2cc(Cl)ccc12)N1[C@H]2C[C@@H]3CC[N@](C2)C[C@@H]31]

(S)-tert-butyl 2-((benzyloxy)methyl)-2,3-dihydro-1H-pyrrolo[2,3-c]pyridine-1-carboxylate was subjected to the conditions employed in example 16, steps B-F to afford (6-chloro-1H-indazol-3-yl)((2S,3aS,6R,7aR)-hexahydro-2,6-methanopyrrolo [2,3-c]pyridin-1(2H)-yl)methanone (26 mg) LCMS METHOD C: retention time=2.72, M+H=317.13. ¹H NMR (400 MHz, CHLOROFORM-d) δ=8.21 (t, J=8.8 Hz, 1H), 7.45 (d, J=1.3 Hz, 1H), 7.25-7.12 (m, 1H), 5.37-5.09 (m, 1H), 5.00-4.75 (m, 1H), 3.83-3.42 (m, 2H), 3.33-2.68 (m, 5H), 2.38-2.17 (m, 1H), 1.96-1.68 (m, 3H), 0.90 (br. s., 1H).

Example 18

((2S,3aS,6R,7aR)-hexahydro-2,6-methanopyrrolo[2,3-c]pyridin-1(2H)-yl)(1H-indazol-3-yl)methanone

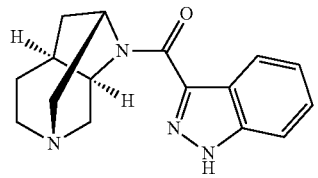 [SMILES: O=C(c1n[nH]c2ccccc12)N1[C@H]2C[C@@H]3CC[N@](C2)C[C@@H]31]

Step A: (2R,3aR,7aS)-6-benzyl 1-tert-butyl 2-((tosyloxy)methyl)hexahydro-1H-pyrrolo[2,3-c]pyridine-1,6(2H)-dicarboxylate and (2S,3aS,7aR)-6-benzyl 1-tert-butyl 2-((tosyloxy)methyl) hexahydro-1H-pyrrolo[2,3-c]pyridine-1,6(2H)-dicarboxylate

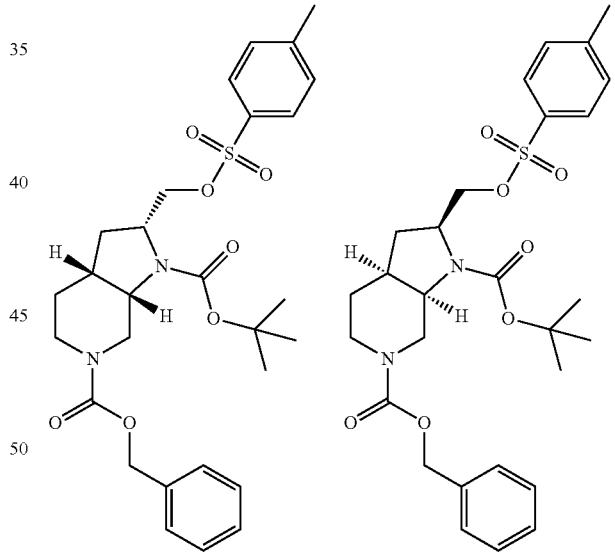

Chiral SFC separation was performed on 6-benzyl 1-tert-butyl 2-((tosyloxy)methyl)hexahydro-1H-pyrrolo[2,3-c]pyridine-1,6(2H)-dicarboxylate (racemic mixture of diastereomers) (~1 g). Conditions: Column=Chiralpak AD-H 30×250 mm, 5 um; Mobile phase=15% IPA in C02; Temp=35° C.; Pressure=150 bar; flow rate=70 mL/min; UV monitored at 220 nm; injection: ~1 mL of a ~50 mg/mL solution in IPA. Four peaks were collected, two major (first two eluting) and two minor. The minor peaks were believed to be undesired and discarded. The first eluting peak was believed to be (2R,3aR,7aS)-6-benzyl 1-tert-butyl 2-((tosyloxy)methyl)hexahydro-1H-pyrrolo[2,3-c]pyridine-1,6

(2H)-dicarboxylate (301.4 mg, 30% of total) and the second peak was believed to be (2S,3aS,7aR)-6-benzyl 1-tert-butyl 2-((tosyloxy)methyl)hexahydro-1H-pyrrolo[2,3-c]pyridine-1,6(2H)-dicarboxylate (299.3 mg, 30% of total).

Step B: (2S,3aS,6R,7aR)-octahydro-2,6-methanopyrrolo[2,3-c]pyridine, 2 TFA

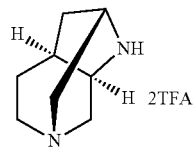

In a Parr bottle was added (2S,3aS,7aR)-6-benzyl 1-tert-butyl 2-((tosyloxy)methyl)hexahydro-1H-pyrrolo[2,3-c]pyridine-1,6(2H)-dicarboxylate (301 mg, 0.789 mmol) and 10% palladium on carbon (75 mg, 0.789 mmol) in ethanol (15 mL). This was placed on the Parr apparatus at 55 PSI for 24 hours. The reaction was removed, filtered through celite and then the mother liquors were treated with potassium carbonate (1 g), and the reaction was heated to reflux for 3 hours. The reaction mixture was cooled to room temperature and concentrated to residue to give the Boc-protected intermediate (85 mg, 65% yield). The residue was dissolved in 1 mL chloroform and TFA (1 mL) was added. The mixture was stirred for 1 h and evaporated to dryness, and then azeotroped with chloroform to remove residual TFA. Quantitative yield on the deprotection step was assumed for the purposes of calculating stoichiometry in the next step: (2S,3aS,6R,7aR)-octahydro-2,6-methanopyrrolo[2,3-c]pyridine, 2 TFA (0.13 g, 0.36 mmol, 65% yield).

Step C: ((2S,3aS,6R,7aR)-hexahydro-2,6-methanopyrrolo[2,3-c]pyridin-1(2H)-yl)(indazol-3-yl)methanone

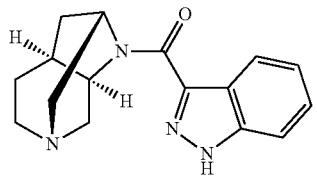 [SMILES: O=C(c1n[nH]c2ccccc12)N1[C@H]2C[C@@H]3CC[N@](C2)C[C@@H]31]

Reacting (2S,3aS,6R,7aR)-octahydro-2,6-methanopyrrolo[2,3-c]pyridine, 2 TFA and 1H-indazole-3-carboxylic acid (16 mg, 0.10 mmol), according to the method of example 2, step B afforded ((2S,3aS,6R,7aR)-hexahydro-2,6-methanopyrrolo[2,3-c]pyridin-1(2H)-yl)(1H-indazol-3-yl)methanone. Purification conditions: Column: Waters XBridge C18, 19×250 mm, 5-μm particles; Guard Column: Waters XBridge C18, 19×10 mm, 5-μm particles; Mobile Phase A: water with 20-mM ammonium-hydroxide; Mobile Phase B: 95:5 methanol:water with 20-mM ammonium-hydroxide; Gradient: 30-95% B over 28 minutes, then a 5-minute hold at 95% B; Flow: 20 mL/min. Fractions containing the desired product were combined and dried via centrifugal evaporation. The yield of the product was 11.1 mg, and its estimated purity by LCMS analysis was 100%. Two analytical LC/MS injections were used to determine the final purity. Injection 1 conditions: Column: Waters BEH C18, 2.0×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7 μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. LCMS retention time=2.46 min, M+H=283.15. Proton NMR was acquired in deuterated DMSO. $^1$H NMR (500 MHz, DMSO-$d_6$) δ=13.51 (br. s., 1H), 8.21-8.01 (m, 1H), 7.61 (d, J=8.5 Hz, 1H), 7.42 (t, J=7.6 Hz, 1H), 7.23 (t, J=7.5 Hz, 1H), 5.30-5.05 (m, 1H), 4.68-4.48 (m, 1H), 3.28-2.77 (m, 8H), 2.21-1.96 (m, 1H), 1.62 (br. s., 2H).

Example 19

((2S,3aS,6R,7aR)-hexahydro-2,6-methanopyrrolo[2,3-c]pyridin-1(2H)-yl)(5-phenyl-1H-pyrazol-3-yl)methanone

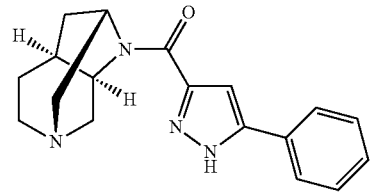 [SMILES: O=C(c1cc(-c2ccccc2)[nH]n1)N1[C@H]2C[C@@H]3CC[N@](C2)C[C@@H]31]

Reacting (2S,3aS,6R,7aR)-octahydro-2,6-methanopyrrolo[2,3-c]pyridine, 2 TFA and 3-phenyl-1H-pyrazole-5-carboxylic acid (19 mg, 0.10 mmol), according to the method of example 2, step B afforded ((2S,3aS,6R,7aR)-hexahydro-2,6-methanopyrrolo[2,3-c]pyridin-1(2H)-yl)(5-phenyl-1H-pyrazol-3-yl)methanone. Purification conditions: Column: Waters XBridge C18, 19×250 mm, 5-μm particles; Guard Column: Waters XBridge C18, 19×10 mm, 5-μm particles; Mobile Phase A: water with 20-mM ammonium-hydroxide; Mobile Phase B: 95:5 methanol:water with 20-mM ammonium-hydroxide; Gradient: 30-95% B over 28 minutes, then a 5-minute hold at 95% B; Flow: 20 mL/min. Fractions containing the desired product were combined and dried via centrifugal evaporation. The yield of the product was 11.1 mg, and its estimated purity by LCMS analysis was 100%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. LCMS retention time=2.83 min, M+H=309.16. Proton NMR was acquired in deuterated DMSO. $^1$H NMR (500 MHz, DMSO-d$_6$) δ=13.79-13.43 (m, 1H), 7.82 (d, J=6.4 Hz, 2H), 7.56-7.28 (m, 3H), 7.17-6.94 (m, 1H), 4.59-4.43 (m, 1H), 3.29-2.63 (m, 9H), 2.22-1.97 (m, 1H), 1.77-1.52 (m, 2H).

Example 20

((2S,3aS,6R,7aR)-hexahydro-2,6-methanopyrrolo[2,3-c]pyridin-1(2H)-yl)(5-cyclopropyl-1H-pyrazol-3-yl)methanone

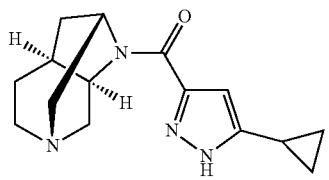 [SMILES: O=C(c1cc(C2CC2)[nH]n1)N1[C@H]2C[C@@H]3CC[N@](C2)C[C@@H]31]

Reacting (2S,3aS,6R,7aR)-octahydro-2,6-methanopyrrolo[2,3-c]pyridine, 2 TFA and 3-cyclopropyl-1H-pyrazole-5-carboxylic acid (15 mg, 0.10 mmol), according to the method of example 2, step B afforded ((2S,3aS,6R,7aR)-hexahydro-2,6-methanopyrrolo[2,3-c]pyridin-1(2H)-yl)(5-cyclopropyl-1H-pyrazol-3-yl)methanone. Purification conditions: Column: Waters XBridge C18, 19×250 mm, 5-μm particles; Guard Column: Waters XBridge C18, 19×10 mm, 5-μm particles; Mobile Phase A: water with 20-mM ammonium-hydroxide; Mobile Phase B: 95:5 methanol:water with 20-mM ammonium-hydroxide; Gradient: 30-95% B over 28 minutes, then a 5-minute hold at 95% B; Flow: 20 mL/min. Fractions containing the desired product were combined and dried via centrifugal evaporation. The yield of the product was 11.6 mg, and its estimated purity by LCMS analysis was 99%. Two analytical LC/MS injections were used to determine the final purity. Injection 1 conditions: Column: Waters BEH C18, 2.0×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7 μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. LCMS retention time=2.20 min, M+H=273.29. Proton NMR was acquired in deuterated DMSO. $^1$H NMR (500 MHz, DMSO-d$_6$) δ=12.89 (br. s., 1H), 6.26 (s, 1H), 5.23-4.84 (m, 1H), 4.56-4.29 (m, 1H), 3.24-2.65 (m, 8H), 2.08-1.91 (m, 1H), 1.82 (d, J=12.5 Hz, 1H), 1.74-1.52 (m, 2H), 0.94 (br. s., 2H), 0.79-0.62 (m, 2H).

Example 21

(6-fluoro-1H-indazol-3-yl)((2S,3aS,6R,7aR)-hexahydro-2,6-methanopyrrolo[2,3-c]pyridin-1(2H)-yl)methanone

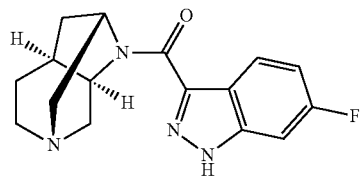 [SMILES: O=C(c1n[nH]c2cc(F)ccc12)N1[C@H]2C[C@@H]3CC[N@](C2)C[C@@H]31]

Reacting (2S,3aS,6R,7aR)-octahydro-2,6-methanopyrrolo[2,3-c]pyridine, 2 TFA and 6-fluoro-1H-indazole-3-carboxylic acid (18 mg, 0.10 mmol), according to the method of example 2, step B afforded (6-fluoro-1H-indazol-3-yl)((2S,3aS,6R,7aR)-hexahydro-2,6-methanopyrrolo[2,3-c]pyridin-1(2H)-yl)methanone. Purification conditions: Column: Waters XBridge C18, 19×250 mm, 5-μm particles; Guard Column: Waters XBridge C18, 19×10 mm, 5 μm particles; Mobile Phase A: water with 20-mM ammonium-hydroxide; Mobile Phase B: 95:5 methanol:water with 20-mM ammonium-hydroxide; Gradient: 30-95% B over 28 minutes, then a 5-minute hold at 95% B; Flow: 20 mL/min. Fractions containing the desired product were combined and dried via centrifugal evaporation. The yield of the product was 11.9 mg, and its estimated purity by LCMS analysis was 95%. Two analytical LC/MS injections were used to determine the final purity. Injection 1 conditions: Column: Waters BEH C18, 2.0×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7 μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. LCMS retention time=2.67 min, M+H=299.14. Proton NMR was acquired in deuterated DMSO. $^1$H NMR (500 MHz, DMSO-d$_6$) δ=13.59 (br. s., 1H), 8.13 (dt, J=5.5, 8.7 Hz, 1H), 7.41 (d, J=9.5 Hz, 1H), 7.21-7.04 (m, 1H), 5.34-5.01 (m, 1H), 4.64-4.48 (m, 1H), 3.29-2.79 (m, 8H), 2.26-2.04 (m, 1H), 1.80-1.54 (m, 2H).

Example 22

(7-Chloro-1H-indazol-3-yl)((2S,3aS,6R,7aR)-hexahydro-2,6-methanopyrrolo[2,3-c]pyridin-1(2H)-yl)methanone

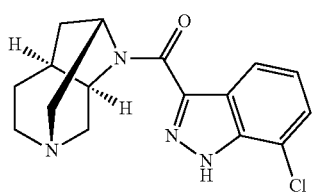 [SMILES: O=C(c1n[nH]c2c(Cl)cccc12)N1[C@H]2C[C@@H]3CC[N@](C2)C[C@@H]31]

Reacting (2S,3aS,6R,7aR)-octahydro-2,6-methanopyrrolo[2,3-c]pyridine, 2 TFA and 7-chloro-1H-indazole-3-carboxylic acid (20 mg, 0.10 mmol), according to the method of example 2, step B afforded (7-Chloro-1H-indazol-3-yl)((2S,3aS,6R,7aR)-hexahydro-2,6-methanopyrrolo[2,3-c]pyridin-1(2H)-yl)methanone. Purification conditions: Column: Waters XBridge C18, 19×250 mm, 5 μm particles; Guard Column: Waters XBridge C18, 19×10 mm, 5-μm particles; Mobile Phase A: water with 20-mM ammonium-hydroxide; Mobile Phase B: 95:5 methanol:water with 20-mM ammonium-hydroxide; Gradient: 30-95% B over 28 minutes, then a 5-minute hold at 95% B; Flow: 20 mL/min. Fractions containing the desired product were combined and dried via centrifugal evaporation. The yield of the product was 7.6 mg, and its estimated purity by LCMS analysis was 99%. Two analytical LC/MS injections were used to determine the final purity. Injection 1 conditions: Column: Waters BEH C18, 2.0×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7 μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. LCMS retention time=2.96 min, M+H=317.11. Proton NMR was acquired in deuterated DMSO. $^1$H NMR (500 MHz, DMSO-d$_6$) δ=14.34-13.62 (m, 1H), 8.16-7.92 (m, 1H), 7.53 (d, J=7.3 Hz, 1H), 7.23 (t, J=7.6 Hz, 1H), 5.23-5.02 (m, 1H), 4.73-4.53 (m, 1H), 3.29-2.73 (m, 8H), 2.26-1.99 (m, 1H), 1.83-1.56 (m, 2H).

Example 23

(6-methyl-1H-indazol-3-yl)((2S,3aS,6R,7aR)-hexahydro-2,6-methanopyrrolo[2,3-c]pyridin-1(2H)-yl)methanone

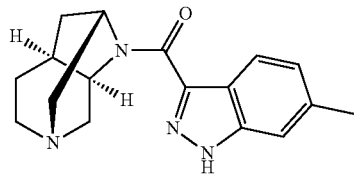 [SMILES: Cc1ccc2c(C(=O)N3[C@H]4C[C@@H]5CC[N@](C4)C[C@@H]53)n[nH]c2c1]

Reacting (2S,3aS,6R,7aR)-octahydro-2,6-methanopyrrolo[2,3-c]pyridine, 2 TFA and 6-methyl-1H-indazole-3-carboxylic acid (18 mg, 0.10 mmol), according to the method of example 2, step B afforded (6-methyl-1H-indazol-3-yl)((2S,3aS,6R,7aR)-hexahydro-2,6-methanopyrrolo[2,3-c]pyridin-1(2H)-yl)methanone. Purification conditions: Column: Waters XBridge C18, 19×250 mm, 5 μm particles; Guard Column: Waters XBridge C18, 19×10 mm, 5 μm particles; Mobile Phase A: water with 20-mM ammonium-hydroxide; Mobile Phase B: 95:5 methanol:water with 20-mM ammonium-hydroxide; Gradient: 30-95% B over 28 minutes, then a 5-minute hold at 95% B; Flow: 20 mL/min. Fractions containing the desired product were combined and dried via centrifugal evaporation. The yield of the product was 11.1 mg, and its estimated purity by LCMS analysis was 92%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. LCMS retention time=2.83 min, M+H=297.28. Proton NMR was acquired in deuterated DMSO. $^1$H NMR (500 MHz, DMSO-d$_6$) δ=13.40-13.16 (m, 1H), 8.04-7.92 (m, 1H), 7.37 (s, 1H), 7.06 (d, J=8.2 Hz, 1H), 5.27-4.98 (m, 1H), 4.65-4.47 (m, 1H), 3.26-2.70 (m, 8H), 2.46 (s, 3H), 2.21-1.98 (m, 1H), 1.61 (d, J=2.7 Hz, 2H).

Example 24

((2S,3aS,6R,7aR)-hexahydro-2,6-methanopyrrolo[2,3-c]pyridin-1(2H)-yl)(1H-pyrazolo[3,4-b]pyridin-3-yl)methanone

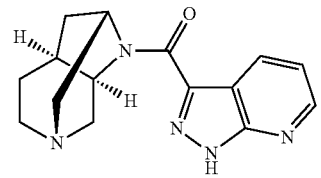

Reacting (2S,3aS,6R,7aR)-octahydro-2,6-methanopyrrolo[2,3-c]pyridine, 2 TFA and 1H-pyrazolo[3,4-b]pyridine-3-carboxylic acid (16 mg, 0.10 mmol), according to the method of example 2, step B afforded ((2S,3aS,6R,7aR)-hexahydro-2,6-methanopyrrolo[2,3-c]pyridin-1(2H)-yl)(1H-pyrazolo[3,4-b]pyridin-3-yl)methanone. Purification conditions: Column: Waters XBridge C18, 19×250 mm, 5-μm particles; Guard Column: Waters XBridge C18, 19×10 mm, 5-μm particles; Mobile Phase A: water with 20-mM ammonium-hydroxide; Mobile Phase B: 95:5 methanol:water with 20-mM ammonium-hydroxide; Gradient: 30-95% B over 28 minutes, then a 5-minute hold at 95% B; Flow: 20 mL/min. Fractions containing the desired product were combined and dried via centrifugal evaporation. The yield of the product was 12.0 mg, and its estimated purity by LCMS analysis was 99%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. LCMS retention time=2.12 min, M+H=282.26. Proton NMR was acquired in deuterated DMSO. ¹H NMR (500 MHz, DMSO-d₆) δ=14.27-13.96 (m, 1H), 8.60 (dd, J=1.7, 4.4 Hz, 1H), 8.53-8.47 (m, 1H), 7.32 (dd, J=4.4, 8.1 Hz, 1H), 5.32-5.12 (m, 1H), 4.55 (d, J=5.8 Hz, 1H), 3.29-2.75 (m, 8H), 2.22-2.00 (m, 1H), 1.83-1.51 (m, 2H).

Example 25

((2R,3aR,6S,7aS)-hexahydro-2,6-methanopyrrolo[2,3-c]pyridin-1(2H)-yl)(isoquinolin-1-yl)methanone

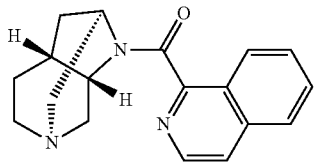 [SMILES: O=C(c1nccc2ccccc12)N1[C@@H]2C[C@H]3CC[N@@](C2)C[C@H]31]

Step A: (2R,3aR,6S,7aS)-octahydro-2,6-methanopyrrolo[2,3-c]pyridine, 2 TFA

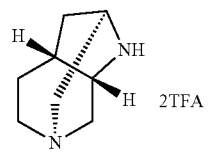

(2R,3aR,7aS)-6-benzyl 1-tert-butyl 2-((tosyloxy)methyl)hexahydro-1H-pyrrolo[2,3-c]pyridine-1,6(2H)-dicarboxylate (301 mg, 0.55 mmol) was reacted according to the method of Example 18, step B to afford (2R,3aR,6S,7aS)-octahydro-2,6-methanopyrrolo[2,3-c]pyridine, 2 TFA (110 mg, 84% yield). ¹H NMR (400 MHz, DMSO-d₆) δ=11.08-10.26 (m, 1H), 9.52-9.14 (m, 2H), 4.32-4.20 (m, 2H), 3.80-3.64 (m, 2H), 3.59-3.37 (m, 4H), 2.88 (t, J=9.0 Hz, 1H), 2.37-2.12 (m, 2H), 1.99-1.83 (m, 2H).

Step B: ((2R,3aR,6S,7aS)-hexahydro-2,6-methanopyrrolo[2,3-c]pyridin-1(2H)-yl)(isoquinolin-1-yl)methanone

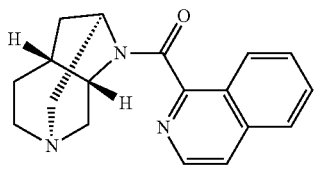 [SMILES: O=C(c1nccc2ccccc12)N1[C@@H]2C[C@H]3CC[N@@](C2)C[C@H]31]

Reacting (2R,3aR,6S,7aS)-octahydro-2,6-methanopyrrolo[2,3-c]pyridine, 2 TFA and isoquinoline-1-carboxylic acid (17 mg, 0.10 mmol), according to the method of example 2, step B afforded ((2R,3aR,6S,7aS)-hexahydro-2,6-methanopyrrolo[2,3-c]pyridin-1(2H)-yl)(isoquinolin-1-yl)methanone. Purification conditions: Column: Waters XBridge C18, 19×200 mm, 5 μm particles; Guard Column: Waters XBridge C18, 19×10 mm, 5 μm particles; Mobile Phase A: water; Mobile Phase B: methanol; Buffer: 20-mM ammonium acetate; Gradient: 30-95% B over 19.5 minutes, then a 14.0 minute hold at 95% B; Flow: 20 mL/min. Fractions containing the desired product were combined and dried via centrifugal evaporation. The yield of the product was 4.5 mg, and its estimated purity by LCMS analysis was 100%. Two analytical LC/MS injections were used to determine the final purity. Injection 1 conditions: Column: Waters BEH C18, 2.0×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. LCMS retention time=1.42 min, M+H=294.15. Injection 2 conditions: Column: Waters BEH C18, 2.0×50 mm, 1.7 μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Proton NMR was acquired in deuterated DMSO. ¹H NMR (500 MHz, DMSO-d₆) δ=8.62-8.49 (m, 1H), 8.17 (t, J=9.5 Hz, 1H), 8.09 (d, J=8.2 Hz, 1H), 8.00 (d, J=5.5 Hz, 1H), 7.87 (t, J=7.5 Hz, 1H), 7.84-7.70 (m, 1H), 5.04-4.91 (m, 1H), 4.02 (br. s., 1H), 3.49 (d, J=12.2 Hz, 4H), 3.27-3.11 (m, 2H), 2.98 (br. s., 1H), 2.36-2.13 (m, 1H), 1.94 (d, J=13.1 Hz, 1H), 1.93-1.59 (m, 1H).

Example 26

(6-fluoro-1H-indazol-3-yl)((2R,3aR,6S,7aS)-hexahydro-2,6-methanopyrrolo[2,3-c]pyridin-1(2H)-yl)methanone

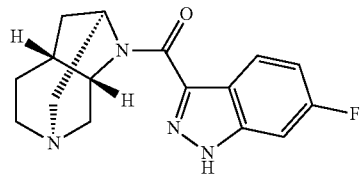 [SMILES: O=C(c1n[nH]c2cc(F)ccc12)N1[C@@H]2C[C@H]3CC[N@@](C2)C[C@H]31]

Reacting (2R,3aR,6S,7aS)-octahydro-2,6-methanopyrrolo[2,3-c]pyridine, 2 TFA and 6-fluoro-1H-indazole-3-carboxylic acid (18 mg, 0.10 mmol), according to the method of example 2, step B afforded (6-fluoro-1H-indazol-3-yl)((2R,3aR,6S,7aS)-hexahydro-2,6-methanopyrrolo[2,3-c]pyridin-1(2H)-yl)methanone. Purification conditions: Column: Waters XBridge C18, 19×200 mm, 5 μm particles; Guard Column: Waters XBridge C18, 19×10 mm, 5 μm particles; Mobile Phase A: water; Mobile Phase B: methanol; Buffer: 20-mM ammonium hydroxide; Gradient: 30-95% B over 19.5 minutes, then a 14.0 minute hold at 95% B; Flow: 20 mL/min. Fractions containing the desired product were combined and dried via centrifugal evaporation. The yield of the product was 16.3 mg, and its estimated purity by LCMS analysis was 98%. Two analytical LC/MS injections were used to determine the final purity. Injection 1 conditions: Column: Waters BEH C18, 2.0×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7-μm particles; Mobile Phase A: 5:95 methanol:water with 10 mM ammonium acetate; Mobile Phase B:

95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. LCMS retention time=2.65 min, M+H=301.14. Proton NMR was acquired in deuterated DMSO. $^1$H NMR (500 MHz, DMSO-$d_6$) δ=8.13 (dt, J=5.5, 8.7 Hz, 1H), 7.42 (d, J=9.5 Hz, 1H), 7.12 (t, J=9.3 Hz, 1H), 5.30-4.96 (m, 1H), 4.55 (d, J=8.2 Hz, 1H), 3.17-2.69 (m, 9H), 2.24-2.04 (m, 1H), 1.76-1.47 (m, 2H) (integration complicated by large water peak that obscures some signals).

Example 27

((2R,3aR,6S,7aS)-hexahydro-2,6-methanopyrrolo[2,3-c]pyridin-1(2H)-yl)(5-cyclopropyl-1H-pyrazol-3-yl)methanone

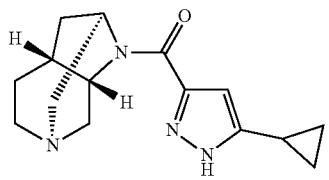 [SMILES: O=C(c1cc(C2CC2)[nH]n1)N1[C@@H]2C[C@H]3CC[N@@](C2)C[C@H]31]

Reacting (2R,3aR,6S,7aS)-octahydro-2,6-methanopyrrolo[2,3-c]pyridine, 2 TFA and 3-cyclopropyl-1H-pyrazole-5-carboxylic acid (15 mg, 0.10 mmol), according to the method of example 2, step B afforded ((2R,3aR,6S,7aS)-hexahydro-2,6-methanopyrrolo[2,3-c]pyridin-1(2H)-yl)(5-cyclopropyl-1H-pyrazol-3-yl)methanone. Purification conditions: Column: Waters XBridge C18, 19×200 mm, 5-μm particles; Guard Column: Waters XBridge C18, 19×10 mm, 5-μm particles; Mobile Phase A: water; Mobile Phase B: methanol; Buffer: 20-mM ammonium hydroxide; Gradient: 30-95% B over 19.5 minutes, then a 14.0 minute hold at 95% B; Flow: 20 mL/min. Fractions containing the desired product were combined and dried via centrifugal evaporation. The yield of the product was 16.0 mg, and its estimated purity by LCMS analysis was 96%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. LCMS retention time=2.20 min, M+H=271.16. Proton NMR was acquired in deuterated DMSO. $^1$H NMR (500 MHz, DMSO-$d_6$) δ=13.18-12.61 (m, 1H), 6.26 (s, 1H), 5.29-4.79 (m, 1H), 4.65-4.32 (m, 1H), 3.08-2.67 (m, 6H), 2.08 (br. s., 1H), 1.87-1.49 (m, 4H), 0.94 (d, J=7.0 Hz, 2H), 0.79-0.52 (m, 3H) (integration complicated by large water peak that obscures some signals).

Example 28

(7-chloro-1H-indazol-3-yl)((2R,3aR,6S,7aS)-hexahydro-2,6-methanopyrrolo[2,3-c]pyridin-1(2H)-yl)methanone

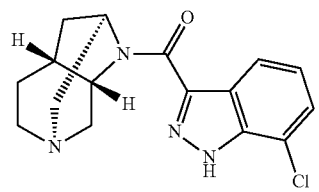 [SMILES: O=C(c1n[nH]c2c(Cl)cccc12)N1[C@@H]2C[C@H]3CC[N@@](C2)C[C@H]31]

Reacting (2R,3aR,6S,7aS)-octahydro-2,6-methanopyrrolo[2,3-c]pyridine, 2 TFA and 7-chloro-1H-indazol-3-carboxylic acid (20 mg, 0.10 mmol), according to the method of example 2, step B afforded (7-chloro-1H-indazol-3-yl)((2R,3aR,6S,7aS)-hexahydro-2,6-methanopyrrolo[2,3-c]pyridin-1(2H)-yl)methanone. Purification conditions: Column: Waters XBridge C18, 19×200 mm, 5 μm particles; Guard Column: Waters XBridge C18, 19×10 mm, 5 μm particles; Mobile Phase A: water; Mobile Phase B: methanol; Buffer: 20-mM ammonium hydroxide; Gradient: 30-95% B over 19.5 minutes, then a 14.0 minute hold at 95% B; Flow: 20 mL/min. Fractions containing the desired product were combined and dried via centrifugal evaporation. The yield of the product was 14.4 mg, and its estimated purity by LCMS analysis was 97%. Two analytical LC/MS injections were used to determine the final purity. Injection 1 conditions: Column: Waters BEH C18, 2.0×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7 μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. LCMS retention time=2.94 min, M+H=317.11. Proton NMR was acquired in deuterated DMSO. $^1$H NMR (500 MHz, DMSO-$d_6$) δ=8.08 (t, J=8.4 Hz, 1H), 7.54 (d, J=7.3 Hz, 1H), 7.24 (t, J=7.8 Hz, 1H), 5.23-4.95 (m, 1H), 4.69-4.51 (m, 1H), 3.12-2.65 (m, 5H), 2.25-2.01 (m, 1H), 1.62 (d, J=4.3 Hz, 2H) (some signals obscured by large water peak).

Example 29 benzo[d]isoxazol-3-yl((2R,3aR,6S,7aS)-hexahydro-2,6-methanopyrrolo[2,3-c]pyridin-1(2H)-yl)methanone

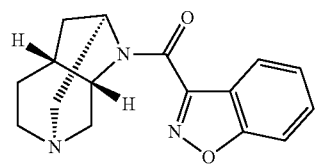 [SMILES: O=C(c1noc2ccccc12)N1[C@@H]2C[C@H]3CC[N@@](C2)C[C@H]31]

Reacting (2R,3aR,6S,7aS)-octahydro-2,6-methanopyrrolo[2,3-c]pyridine, 2 TFA and benzo[d]isoxazole-3-carboxylic acid (16 mg, 0.10 mmol), according to the method of example 2, step B afforded benzo[d]isoxazol-3-yl((2R,3aR,6S,7aS)-hexahydro-2,6-methanopyrrolo[2,3-c]pyridin-1(2H)-yl)methanone. Purification conditions: Phase A: water; Mobile Phase B: methanol; Buffer: 20-mM ammonium hydroxide; Gradient: 30-95% B over 19.5 minutes, then a 14.0 minute hold at 95% B; Flow: 20 mL/min. Fractions containing the desired product were combined and dried via centrifugal evaporation. The yield of the product was 10.6 mg, and its estimated purity by LCMS analysis was 99%. Two analytical LC/MS injections were used to determine the final purity. Injection 1 conditions: Column: Waters BEH C18, 2.0×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7 μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. LCMS retention time=2.92 min, M+H=317.11. Proton NMR was acquired in deuterated DMSO. $^1$H NMR (500 MHz, DMSO-$d_6$) δ=8.08-7.96 (m, 1H), 7.88 (d, J=8.5 Hz, 1H), 7.75 (t, J=7.8 Hz, 1H), 7.50 (t, J=7.6 Hz, 1H), 4.60 (d, J=10.7 Hz, 2H), 3.27-2.70 (m, 6H), 2.23-2.07 (m, 1H), 1.63 (br. s., 2H) (some signals obscured by large water peak).

Example 30

(6-methyl-1H-indazol-3-yl)((2R,3aR,6S,7aS)-hexahydro-2,6-methanopyrrolo[2,3-c]pyridin-1(2H)-yl)methanone

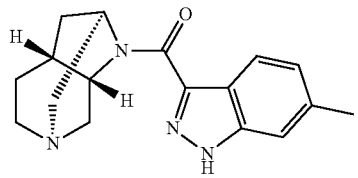 [SMILES: Cc1ccc2c(C(=O)N3[C@@H]4C[C@H]5CC[N@@](C4)C[C@H]53)n[nH]c2c1]

Reacting (2R,3aR,6S,7aS)-octahydro-2,6-methanopyrrolo[2,3-c]pyridine, 2 TFA and 6-methyl-1H-indazole-3-carboxylic acid (18 mg, 0.10 mmol), according to the method of example 2, step B afforded (6-methyl-1H-indazol-3-yl)((2R,3aR,6S,7aS)-hexahydro-2,6-methanopyrrolo[2,3-c]pyridin-1(2H)-yl)methanone. Purification conditions: Column: Waters XBridge C18, 19×200 mm, 5 μm particles; Guard Column: Waters XBridge C18, 19×10 mm, 5 μm particles; Mobile Phase A: water; Mobile Phase B: methanol; Buffer: 20-mM ammonium hydroxide; Gradient: 30-95% B over 19.5 minutes, then a 14.0 minute hold at 95% B; Flow: 20 mL/min. Fractions containing the desired product were combined and dried via centrifugal evaporation. The yield of the product was 14.2 mg, and its estimated purity by LCMS analysis was 98%. Two analytical LC/MS injections were used to determine the final purity. Injection 1 conditions: Column: Waters BEH C18, 2.0×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7 μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. LCMS retention time=2.81 min, M+H=297.16. Proton NMR was acquired in deuterated DMSO. $^1$H NMR (500 MHz, DMSO-$d_6$) δ=13.81-12.70 (m, 1H), 7.98 (t, J=8.4 Hz, 1H), 7.37 (s, 1H), 7.06 (d, J=8.2 Hz, 1H), 5.34-5.02 (m, 1H), 4.73-4.51 (m, 1H), 3.10-2.62 (m, 6H), 2.21-2.01 (m, 1H), 1.86-1.53 (m, 2H) (some signals obscured by large water peak).

Example 31

((2R,3aR,6S,7aS)-hexahydro-2,6-methanopyrrolo[2,3-c]pyridin-1(2H)-yl)(1H-pyrazolo[3,4-b]pyridin-3-yl)methanone

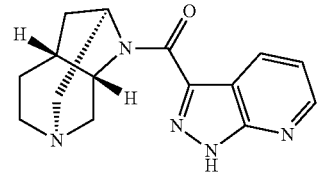 [SMILES: O=C(c1n[nH]c2ncccc12)N1[C@@H]2C[C@H]3CC[N@@](C2)C[C@H]31]

Reacting (2R,3aR,6S,7aS)-octahydro-2,6-methanopyrrolo[2,3-c]pyridine, 2 TFA and 1H-pyrazolo[3,4-b]pyridine-3-carboxylic acid (16 mg, 0.10 mmol), according to the method of example 2, step B afforded ((2R,3aR,6S,7aS)-hexahydro-2,6-methanopyrrolo[2,3-c]pyridin-1(2H)-yl)(1H-pyrazolo[3,4-b]pyridin-3-yl)methanone. Purification conditions: Column: Waters XBridge C18, 19×200 mm, 5 μm particles; Guard Column: Waters XBridge C18, 19×10 mm, 5 μm particles; Mobile Phase A: water; Mobile Phase B: methanol; Buffer: 20-mM ammonium hydroxide; Gradient: 30-95% B over 19.5 minutes, then a 14.0 minute hold at 95% B; Flow: 20 mL/min. Fractions containing the desired product were combined and dried via centrifugal evaporation. The yield of the product was 16.4 mg, and its estimated purity by LCMS analysis was 97%. Two analytical LC/MS injections were used to determine the final purity. Injection 1 conditions: Column: Waters BEH C18, 2.0×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7 μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. LCMS retention time=2.13 min, M+H=284.14. Proton NMR was acquired in deuterated DMSO. $^1$H NMR (500 MHz, DMSO-$d_6$) δ=8.60 (d, J=4.6 Hz, 1H), 8.50 (t, J=6.9 Hz, 1H), 7.32 (dd, J=4.6, 7.9 Hz, 1H), 5.35-5.09 (m, 1H), 4.68-4.45 (m, 1H), 3.20-2.61 (m, 7H), 2.23-2.03 (m, 1H), 1.88-1.56 (m, 3H)) (some signals obscured by large water peak).

Example 32

((2R,3aR,6S,7aS)-hexahydro-2,6-methanopyrrolo[2,3-c]pyridin-1(2H)-yl)(5-phenyl-1H-pyrazol-3-yl)methanone

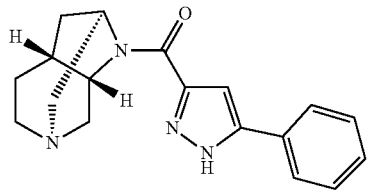 [SMILES: O=C(c1cc(-c2ccccc2)[nH]n1)N1[C@@H]2C[C@H]3CC[N@@](C2)C[C@H]31]

Reacting (2R,3aR,6S,7aS)-octahydro-2,6-methanopyrrolo[2,3-c]pyridine, 2 TFA and 3-phenyl-1H-pyrazole-5-carboxylic acid (19 mg, 0.10 mmol), according to the method of example 2, step B afforded ((2R,3aR,6S,7aS)-hexahydro-2,6-methanopyrrolo[2,3-c]pyridin-1(2H)-yl)(5-phenyl-1H-pyrazol-3-yl)methanone. purification conditions: Column: Waters XBridge C18, 19×200 mm, 5 µm particles; Guard Column: Waters XBridge C18, 19×10 mm, 5 µm particles; Mobile Phase A: water; Mobile Phase B: methanol; Buffer: 20-mM ammonium hydroxide; Gradient: 30-95% B over 19.5 minutes, then a 14.0 minute hold at 95% B; Flow: 20 mL/min. Fractions containing the desired product were combined and dried via centrifugal evaporation. The material was further purified via preparative LC/MS with the following conditions: Column: Waters XBridge C18, 19×200 mm, 5 µm particles; Guard Column: Waters XBridge C18, 19×10 mm, 5 µm particles; Mobile Phase A: water; Mobile Phase B: acetonitrile; Buffer: 20-mM ammonium acetate; Gradient: 20-95% B over 20.5 minutes, then a 7.0 minute hold at 95% B; Flow: 25 mL/min. Fractions containing the desired product were combined and dried via centrifugal evaporation. The yield of the product was 15.8 mg, and its estimated purity by LCMS analysis was 97%. Two analytical LC/MS injections were used to determine the final purity. Injection 1 conditions: Column: Waters BEH C18, 2.0×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. LCMS retention time=1.53 min, M+H=309.16. Injection 2 conditions: Column: Waters BEH C18, 2.0×50 mm, 1.7 µm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Proton NMR was acquired in deuterated DMSO. $^1$H NMR (500 MHz, DMSO-$d_6$) δ=7.88-7.78 (m, 2H), 7.52-7.43 (m, 2H), 7.38 (d, J=7.6 Hz, 1H), 7.10-7.03 (m, 1H), 4.58-4.41 (m, 1H), 3.08-2.62 (m, 7H), 2.20-1.96 (m, 2H), 1.75-1.52 (m, 2H) (some signals obscured by large water peak).

Example 33

((2R,3aR,6S,7aS)-hexahydro-2,6-methanopyrrolo[2,3-c]pyridin-1(2H)-yl)(1H-indazol-3-yl)methanone

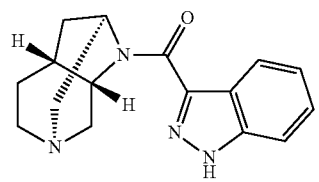 [SMILES: O=C(c1n[nH]c2ccccc12)N1[C@@H]2C[C@H]3CC[N@@](C2)C[C@H]31]

Reacting (2R,3aR,6S,7aS)-tert-butyl hexahydro-2,6-methanopyrrolo[2,3-c]pyridine-1(2H)-carboxylate and 1H-indazole-3-carboxylic acid (34 mg, 0.21 mmol), according to the method of example 16, step F afforded ((2R,3aR,6S,7aS)-hexahydro-2,6-methanopyrrolo[2,3-c]pyridin-1(2H)-yl)(1H-indazol-3-yl)methanone (52 mg, 83% yield). Purification conditions: Silica gel column, 5-40% (9:1 MeOH/NH$_4$OH) in chloroform. LCMS METHOD C: retention time=2.36, M+H=283.25. $^1$H NMR (400 MHz, CHLOROFORM-d) δ=11.43-10.87 (m, 1H), 8.38-8.18 (m, 1H), 7.58-7.48 (m, 1H), 7.47-7.39 (m, 1H), 7.33-7.21 (m, 1H), 5.35-5.13 (m, 1H), 4.98-4.79 (m, 1H), 3.68-3.57 (m, 1H), 3.31-2.78 (m, 5H), 2.42-2.22 (m, 1H), 1.93-1.72 (m, 3H), 1.47-1.27 (m, 1H) (HNMR shows some residual Ethanol (from the chloroform used in the purification).

Example 34

((2S*,3aR*,5R*,7aS*)-hexahydro-2,5-methanopyrrolo[3,2-c]pyridin-1(6H)-yl)(1H-indazol-3-yl)methanone

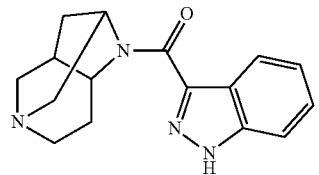 [SMILES: O=C(c1n[nH]c2ccccc12)N1C2CCN3CCC1C(C2)C3]

Step A: tert-butyl (3-(3-(benzyloxy)prop-1-yn-1-yl)pyridin-4-yl)carbamate

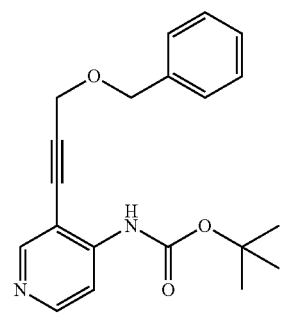 [SMILES: CC(C)(C)OC(=O)Nc1ccncc1C#CCOCc1ccccc1]

A resealable pressure vessel was charged with DMF (15.6 mL), tert-butyl (3-iodopyridin-4-yl)carbamate (5.0 g, 15.6 mmol), ((prop-2-yn-1-yloxy)methyl)benzene (3.04 g, 18.74 mmol), bis(triphenylphosphine)palladium(II) chloride (0.55 g, 0.78 mmol), copper(I) iodide (0.297 g, 1.56 mmol) and triethylamine (43.5 mL, 312 mmol) and the mixture was degassed by bubbling nitrogen through the mixture for several minutes. The reaction mixture was stirred at ambient temperature overnight, diluted with ethyl acetate, washed twice with saturated ammonium chloride solution and once with brine. The combined organic phases were dried over sodium sulfate, filtered and evaporated to dryness. The crude material was purified by silica gel chromatography, eluting with a gradient from 20-50% EtOAc in hexanes. The major peak was collected, affording tert-butyl (3-(3-(benzyloxy)prop-1-yn-1-yl)pyridin-4-yl)carbamate (4.27 g, 81%). $^1$H NMR (400 MHz, CHLOROFORM-d) δ=8.56 (s, 1H), 8.49-8.34 (m, 1H), 8.14 (d, J=5.8 Hz, 1H), 7.51-7.32 (m, 6H), 4.71 (s, 2H), 4.51 (s, 2H), 1.56 (s, 9H).

Step B:
2-((benzyloxy)methyl)-1H-pyrrolo[3,2-c]pyridine

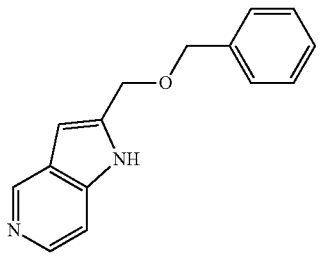 [SMILES: c1ccc(COCc2cc3cnccc3[nH]2)cc1]

A resealable pressure vessel was charged with tert-butyl (3-(3-(benzyloxy)prop-1-yn-1-yl)pyridin-4-yl)carbamate (4.27 g, 12.6 mmol), methanol (80 mL) and water (20 mL) and DBU (13.3 mL, 88 mmol) was added, the vessel was sealed, and the mixture was warmed to 60° C. and maintained at that temperature for 2 h. The mixture was then cooled to ambient temperature, the methanol was removed on the rotovap and the resultant mixture was cooled on an ice bath until precipitate began to form. Cold water (100 mL) was added in a slow stream to further precipitate the product, which was then collected by filtration. The tan solids were then azeotroped with toluene to remove residual water, affording 2-((benzyloxy)methyl)-1H-pyrrolo[3,2-c]pyridine (2.36 g, 78%) as a tan solid. $^1$H NMR (400 MHz, DMSO-$d_6$) δ=12.10-11.21 (m, 1H), 8.79 (d, J=1.0 Hz, 1H), 8.31-7.98 (m, 1H), 7.77-7.06 (m, 6H), 6.56 (s, 1H), 4.69 (s, 2H), 4.56 (s, 2H).

Step C: tert-butyl 2-((benzyloxy)methyl)-1H-pyrrolo[3,2-c]pyridine-1-carboxylate

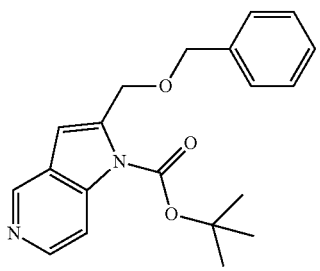 [SMILES: CC(C)(C)OC(=O)n1c(COCc2ccccc2)cc2cnccc21]

A round bottom flask was charged with 2-((benzyloxy)methyl)-1H-pyrrolo[3,2-c]pyridine (2.36 g, 9.9 mmol), dichloromethane (20 mL), di-tert-butyldicarbonate (3.24 mL, 14.9 mmol) and triethylamine (2.2 mL, 15.9 mmol) and allowed to stir overnight. The reaction mixture was evaporated to remove most of the solvent and then purified by silica gel chromatography, eluting with 20-50% EtOAc in hexanes, affording tert-butyl 2-((benzyloxy)methyl)-1H-pyrrolo[3,2-c]pyridine-1-carboxylate (3.16 g, 94%). $^1$H NMR (400 MHz, CHLOROFORM-d) δ=8.87 (d, J=0.8 Hz, 1H), 8.46 (d, J=5.8 Hz, 1H), 7.99 (d, J=6.0 Hz, 1H), 7.51-7.31 (m, 5H), 6.83 (s, 1H), 4.93 (d, J=1.3 Hz, 2H), 4.71 (s, 2H), 1.70 (s, 9H).

Tert-butyl 2-((benzyloxy)methyl)-1H-pyrrolo[3,2-c]pyridine-1-carboxylate was also prepared by the following alternate method: To a stirred solution of tert-butyl (3-iodopyridin-4-yl)carbamate (230 g, 718 mmol) in DMF (2.3 L) was added ((prop-2-yn-1-yloxy)methyl)benzene (126 g, 862 mmol). The mixture was purged with nitrogen for 15 min at which point copper(I) iodide (13.68 g, 71.8 mmol), triethylamine (2.003 L, 1.44E+04 mmol) and bis(triphenylphosphine)palladium(II) chloride (25.2 g, 35.9 mmol) were added and the mixture purged again with nitrogen for 15 min. The reaction mixture was heated to 65° C. for 24 h, at which point TLC (40% EtOAc in petroleum ether) showed some remaining intermediate, so the reaction mixture was re-heated to the same temperature for an additional 24 h. The reaction mixture was then cooled to ambient temperature and concentrated to remove DMF. The residue was diluted with ethyl acetate (3.0 L) and quenched with saturated ammonium chloride solution. The phases were separated, the organics washed with brine and evaporated to afford the crude product, which was purified by silica gel chromatography, eluting with 25-80% of EtOAc in petroleum ether. Mixed fractions were re-purified under the same conditions, and the pure fractions from both columns were combined to afford tert-butyl 2-((benzyloxy)methyl)-1H-pyrrolo[3,2-c]pyridine-1-carboxylate (200 g, 81%). LC/MS Method A: Retention time=2.44 min, M+H=339.0.

Step D: tert-butyl 2-(hydroxymethyl)octahydro-1H-pyrrolo[3,2-c]pyridine-1-carboxylate

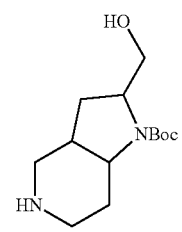

Tert-butyl 2-((benzyloxy)methyl)-1H-pyrrolo[3,2-c]pyridine-1-carboxylate (3.16 g, 9.34 mmol) in EtOH (100 mL) was added to and 20% palladium hydroxide on carbon, 50% wet (1.6 g, 1.139 mmol) in a 500 mL Parr bottle. The mixture was reacted overnight at 55 psi, at which point most of the starting material was consumed. Acetic acid (10 mL) was added to the reaction mixture and it was returned to the Parr shaker and hydrogenated an additional 2 d. TLC again indicated that the reaction was incomplete (this was determined by the presence of UV activity in the reaction mixture), so platinum oxide (750 mg) was added and the mixture again hydrogenated at 55 psi for 2 d more. Again, TLC indicated that the reaction was incomplete, so the catalyst was removed by filtration through celite, and the filtrate was concentrated on the rotovap, made basic by the addition of saturated sodium bicarbonate, extracted 3× with chloroform and dried over sodium sulfate. The mixture was purified by biotage 5-40% (9:1 MeOH/NH₄OH) in chloroform. Two main fractions were obtained, the fully reduced title compound (tert-butyl 2-(hydroxymethyl)octahydro-1H-pyrrolo[3,2-c]pyridine-1-carboxylate (1.06 g, 4.14 mmol, 44.3% yield, mixture of diastereomers)) and the partially reduced tert-butyl 2-(hydroxymethyl)-2,3-dihydro-1H-pyrrolo[3,2-c]pyridine-1-carboxylate (1.0 g, 4.00 mmol, 42.8% yield).

The partially reduced material, tert-butyl 2-(hydroxymethyl)-2,3-dihydro-1H-pyrrolo[3,2-c]pyridine-1-carboxylate (1.0 g, 4.00 mmol) was treated with platinum(IV) oxide (0.5 g, 2.202 mmol) in EtOH (100 mL) and Acetic Acid (20 mL) in a 500 mL Parr bottle and reacted overnight at 55 psi, at which time the reaction was deemed complete by TLC. The mixture was flushed with nitrogen, filtered through celite and evaporated. The resultant residue was partitioned between chloroform and 10% $Na_2CO_3$, and extracted 3×. The combined organics were dried over sodium sulfate, filtered and evaporated to afford tert-butyl 2-(hydroxymethyl)octahydro-1H-pyrrolo[3,2-c]pyridine-1-carboxylate (0.69 g, 2.69 mmol, 67.4% yield, mixture of diastereomers). $^1$H NMR (400 MHz, CHLOROFORM-d) δ=4.24-3.48 (m, 4H), 3.18-2.85 (m, 2H), 2.63-1.56 (m, 7H), 1.55-1.20 (m, 11H). (The product $^1$H NMR is complicated by the diastereomixture and also rotomers from the Boc group).

Tert-butyl 2-(hydroxymethyl)octahydro-1H-pyrrolo[3,2-c]pyridine-1-carboxylate was also prepared by the following alternate method: In a (5 L) auto cleave Ethanol (3.0 L) followed by tert-butyl 2-((benzyloxy)methyl)-1H-pyrrolo[3,2-c]pyridine-1-carboxylate (200 g, 591 mmol) were added under nitrogen purging. To the reaction mixture 5% palladium on carbon (400 g, 1879 mmol) was added under nitrogen atmosphere at RT. To the reaction mixture 15 kg/cm2 of hydrogen pressure was applied and heated to 60° C., stirred for 48 h. The reaction mixture was filtered through a bed of celite and washed with methanol. The filtrate was concentrated and the reaction mixture recharged. In a (5 L) auto cleave Ethanol (3.0 L) followed by reaction mixture (150 g) were added under nitrogen purging. To the reaction mixture 5% palladium on carbon (400 g, 1879 mmol) was added under nitrogen atmosphere at ambient temperature. To the reaction mixture 15 kg/cm2 of hydrogen pressure was applied and heated to 60° C., stirred for an additional 24 h. The reaction mixture was again filtered through celite bed and washed with methanol, and the filtrate was concentrated and taken for the recharge.

In a (5 L) auto cleave Ethanol (3.0 L) followed by reaction mixture (110 g) was added under nitrogen purging. To the reaction mixture 5% palladium on carbon (400 g, 1879 mmol) was added under nitrogen atmosphere at ambient temperature. To the reaction mixture 15 kg/cm2 of hydrogen pressure was applied and heated to 60° C., stirred for 48 h more. The reaction mixture was again filtered through celite bed and washed with methanol, and the filtrate was concentrated and taken for the recharge. In a (5 L) auto cleave Ethanol (3.0 L) followed by reaction mixture (90 g) were added under nitrogen purging. To the reaction mixture 5% palladium on carbon (400 g, 1879 mmol) was added under nitrogen atmosphere at RT. To the reaction mixture 15 kg/cm2 of hydrogen pressure was applied and heated to 60° C., stirred for an additional 24 h. At this point, LCMS monitoring showed the reaction to be ~90% complete, the reaction mixture filtered through celite bed and washed with methanol. The filtrate was concentrated to afford the title compound as a light brown oil (86 g, 57%), which was taken for the next step without further purification. LC/MS Method A (no UV signal): Retention time=1.34 min, M+H=257.2.

Step E: 5-benzyl 1-tert-butyl 2-(hydroxymethyl) hexahydro-1H-pyrrolo[3,2-c]pyridine-1,5(6H)-dicarboxylate

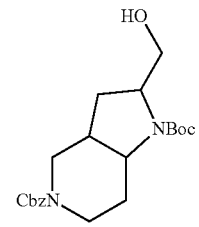

Tert-butyl 2-(hydroxymethyl)octahydro-1H-pyrrolo[3,2-c]pyridine-1-carboxylate (1.75 g, 5.53 mmol) was dissolved in THF (25 mL) and 10% aqueous potassium carbonate solution (25 mL) and benzylchloroformate (1.7 mL, 11.6 mmol) was added. The biphasic mixture was stirred for 30 min, diluted with chloroform and the phases separated. The aqueous fraction was extracted twice again with chloroform and the combined organics dried over sodium sulfate. The crude mixture was purified by silica gel chromatography with an ethyl acetate/hexanes mixture (15%-50%, then hold at 50%). The title compound was obtained as a mixture of diastereomers (2.13 g, 99%) and taken on to the next step as such. LC/MS Method B: Retention time=3.80 min, M+H=391.22.

Step F: (2S*,3aR*,7aS*)-5-benzyl 1-tert-butyl 2-((tosyloxy)methyl)hexahydro-1H-pyrrolo[3,2-c]pyridine-1,5(6H)-dicarboxylate

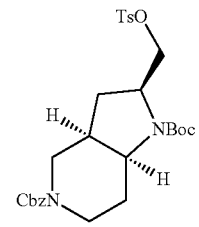

5-benzyl 1-tert-butyl 2-(hydroxymethyl)hexahydro-1H-pyrrolo[3,2-c]pyridine-1,5(6H)-dicarboxylate (2.13 g, 5.45 mmol) was dissolved in pyridine (15 mL) and tosyl chloride (1.25 g, 6.56 mmol) was added. The yellow reaction mixture was stirred overnight. The bulk of the pyridine was evaporated on the rotovap and the mixture was partitioned between 0.1N HCl and Chloroform. The aqueous fraction was extracted 3×, wash with saturated sodium bicarbonate and brine, and dried over sodium sulfate. After filtration and evaporation of the solvent, silica gel chromatography with a gradient of 20-100% EtOAc in hexanes afforded two diastereomers, the second eluting peak (1.8 g, 61%), which was the major component, was taken on to the next step. LC/MS Method B: Retention time=4.26 min, M+H=545.29.

Step G: tert-butyl hexahydro-2,5-methanopyrrolo[3,2-c]pyridine-1(6H)-carboxylate

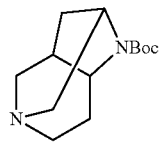 [SMILES: CC(C)(C)OC(=O)N1C2CC3CN(CCC31)C2]

(2S*,3aR*,7aS*)-5-benzyl 1-tert-butyl 2-((tosyloxy)methyl)hexahydro-1H-pyrrolo[3,2-c]pyridine-1,5(6H)-dicarboxylate (1.8 g, 3.30 mmol) and palladium on carbon (0.6 g, 0.564 mmol) were charged to a 500 mL Parr bottle, and ethanol (100 mL) was added. The mixture was flushed with nitrogen and then hydrogenated at 60 psi for 2 h. The reaction mixture was flushed with nitrogen and filtered through celite to remove palladium, washing with 150 mL more EtOH. To the combined filtrates, $K_2CO_3$ (2 g) was added and the mixture was heated on a 75° C. oil bath for 40 min. After evaporation of the solvent, the residue was taken up ~20 mL water, and extracted with chloroform 3×, dried over sodium sulfate, filtered and the solvent evaporated to afford the title compound (0.55 g) as a clear, colorless oil that solidified upon standing cyclized pdt as mixture of rotomers, with EtOH present. ¹H NMR (400 MHz, CHLOROFORM-d) Shift=4.29-3.99 (m, 2 H), 3.33 (dd, J=8.3, 13.6 Hz, 1 H), 3.03 (d, J=13.8 Hz, 1 H), 2.95-2.67 (m, 4 H), 2.42-2.03 (m, 2 H), 1.88 (tdd, J=2.7, 5.5, 10.8 Hz, 1 H), 1.75-1.55 (m, 2 H), 1.54-1.40 (m, 9 H). LC/MS Method B (no UV activity): Retention time=2.33 min, M+H=239.21.

Step H: (2S*,3aR*,5R*,7aS*)-octahydro-2,5-methanopyrrolo[3,2-c]pyridine, 2TFA

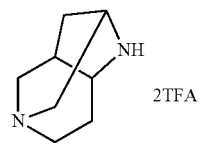

Tert-butyl hexahydro-2,5-methanopyrrolo[3,2-c]pyridine-1 (6H)-carboxylate (0.05 g, 0.21 mmol) was dissolved in chloroform (1 mL) and trifluoroacetic acid was added (0.5 mL) and the mixture was stirred at ambient temperature for 1 h. The solvent was evaporated and the mixture was azeotroped thrice with chloroform to remove excess TFA. The title compound was isolated as a viscous oil and was used directly in the next step without further purification. ¹H NMR (400 MHz, DMSO-$d_6$) δ=10.74 (br. s, 1H), 9.79 (br. s, 1H), 9.46 (br. s., 1H), 4.26 (br. s., 1H), 4.19 (br. s., 1H), 3.83-3.67 (m, 2H), 3.44-3.20 (m, 4H), 2.86-2.75 (m, 1H), 2.31-2.05 (m, 3H), 2.00-1.86 (m, 1H).

Step I: (2S*,3aR*,5R*,7aS*)-(hexahydro-2,5-methanopyrrolo[3,2-c]pyridin-1(6H)-yl)(1H-indazol-3-yl)methanone

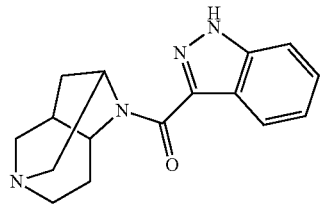 [SMILES: O=C(c1n[nH]c2ccccc12)N1C2CC3CN(CCC31)C2]

A scintillation vial was charged with (2S*,3aR*,5R*,7aS*)-octahydro-2,5-methanopyrrolo[3,2-c]pyridine, 2TFA (39 mg, 0.105 mmol), HATU (50 mg, 0.131 mmol), 1H-indazole-3-carboxylic acid (20 mg, 0.126 mmol) DIPEA (0.1 mL, 0.57 mmol) and DMF (1 mL). The mixture was allowed to stir at ambient temperature overnight. The solvent was removed by evaporation under a stream of nitrogen, and the residue was partitioned between chloroform and saturated aqueous sodium bicarbonate. The phases were separated and the aqueous fraction extracted twice more with chloroform. The combined organic phases were dried over sodium sulfate, filtered and the solvent was removed by evaporation on the rotovap. The resultant residue was purified by silica gel chromatography, eluting with a gradient from 5% to 40% (9:1 MeOH/NH4OH) in chloroform, affording the title compound (24.3 mg). ¹H NMR (400 MHz, CHLOROFORM-d) δ=11.12-10.28 (m, 1H), 8.46-8.24 (m, 1H), 7.65-7.38 (m, 2H), 7.31 (dd, J=0.9, 8.2 Hz, 1H), 5.41-5.05 (m, 1H), 4.95-4.68 (m, 1H), 3.62-2.82 (m, 7H), 2.66-2.37 (m, 2H), 2.13-1.91 (m, 2H).

Examples 34a and 34b ((2S,3aR,5R,7aS)-hexahydro-2,5-methanopyrrolo[3,2-c]pyridin-1(6H)-yl)(1H-indazol-3-yl)methanone and ((2R,3aS,5S,7aR)-hexahydro-2,5-methanopyrrolo[3,2-c]pyridin-1(6H)-yl)(1H-indazol-3-yl)methanone

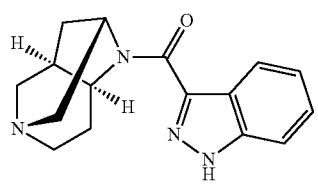

1a

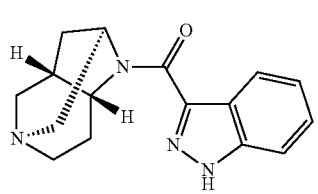

1b (2S*,3aR*,5R*,7aS*)-(hexahydro-2,5-methanopyrrolo[3,2-c]pyridin-1 (6H)-yl)(1H-indazol-3-yl)methanone (75 mg) was separated into individual enantiomers by supercritical fluid chromatography on a Chiralpak IC column (30×250 mm, 5 uM), eluting with 40% MeOH containing 0.1% diethylamine in $CO_2$ (temperature=35° C., Pressure=150 bar, Flow rate: 70 mL/min for 25 min, injection: 1 mL of ~5 mg/mL solution in MeOH, UV monitored at 290 nm). The first peak was collected to afford ((2S,3aR,5R,7aS)-hexahydro-2,5-methanopyrrolo[3,2-c]pyridin-1(6H)-yl)(1H-indazol-3-yl)methanone (31.6 mg, 80%). The second peak was collected to give ((2R,3aS,5S,7aR)-hexahydro-2,5-methanopyrrolo[3,2-c]pyridin-1 (6H)-yl)(1H-indazol-3-yl)methanone (34.7 mg, 88%).

((2S,3aR,5R,7aS)-hexahydro-2,5-methanopyrrolo[3,2-c]pyridin-1(6H)-yl)(1H-indazol-3-yl)methanone was also prepared by the following alternate method:

Step A: (2S,3aR,7aS)-5-benzyl 1-tert-butyl 2-(hydroxymethyl)hexahydro-1H-pyrrolo[3,2-c]pyridine-1,5(6H)-dicarboxylate

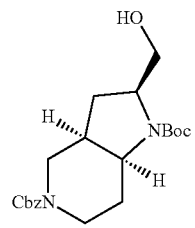 [SMILES: CC(C)(C)OC(=O)N1[C@H](CO)C[C@@H]2CN(C(=O)OCc3ccccc3)CC[C@@H]21]

Tert-butyl 2-(hydroxymethyl)octahydro-1H-pyrrolo[3,2-c]pyridine-1-carboxylate (263 g, 1026 mmol) was charged to a 20 L three neck round bottom flask. To this THF (4000 mL) was added followed by a 10% solution of potassium carbonate (464 g, 3355 mmol)(i.e., 464 g in 4640 mL of water) and the mixture was stirred for 5 min, then neat CBZ-Cl (308 mL, 2155 mmol) was added drop wise over a period of 30 min. After the addition is over the reaction mixture was stirred for another 2 h. When TLC was checked the reaction was completed. The mixture was extracted with ethyl acetate (3×300 mL) and washed with water (200 mL) and brine (200 mL) dried and concentrated to get crude compound as thick liquid, which was purified through silica column first to remove all the impurities and to get the both diastereomers together. 220 g of the diastereomeric mixture obtained from column after purification and the same is submitted for SFC purification.

70 g of first eluting enantiomer obtained from SFC ((2S,3aR,7aS)-5-benzyl 1-tert-butyl 2-(hydroxymethyl)hexahydro-1H-pyrrolo[3,2-c]pyridine-1,5(6H)-dicarboxylate). Specific OR=+18.0°. The mixture of opposite enantiomer and undesired diastereomer was collected separately and kept aside. LC/MS Method A: Retention time=2.23 min, M+H=391.0 (fragments from losing Boc group also present).

This reaction and separation was run multiple times with minor variations. In one variation, the SFC separation was performed on the crude diasteromixture, affording four peaks (Chirlapak AD-H column, 20% EtOH in $CO_2$). In this case, the second eluting peak was taken forward in the following transformations and used for the assignment of the absolute stereochemistry.

Step B: (2S,3aR,7aS)-5-benzyl 1-tert-butyl 2-((tosyloxy)methyl)hexahydro-1H-pyrrolo[3,2-c]pyridine-1,5(6H)-dicarboxylate

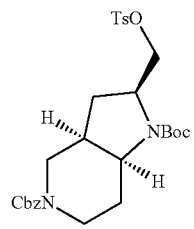

(2S,3aR,7aS)-5-benzyl 1-tert-butyl 2-(hydroxymethyl) hexahydro-1H-pyrrolo[3,2-c]pyridine-1,5(6H)-dicarboxylate (67 g, 172 mmol) was charged to a 2000 mL round bottom flask. Under nitrogen, pyridine (670 mL) was added, followed by tosyl-Cl (72.0 g, 377 mmol) and stirring continued at room temperature overnight. When TLC was checked, starting material was over. The reaction mixture was concentrated and extracted into ethyl acetate (3×250 mL), washed with 1.5N HCl (100 mL) washed with brine (100 mL) and dried over anh. $Na_2SO_4$. The mixture was concentrated to get the crude compound, which was purified by silica gel chromatography using ethyl acetate and petroleum ether gradient as the solvent system. After purification, (2S,3aR,7aS)-5-benzyl 1-tert-butyl 2-((tosyloxy)methyl) hexahydro-1H-pyrrolo[3,2-c]pyridine-1,5(6H)-dicarboxylate (73.8 g, 77%) was obtained. LC/MS Method A: Retention time=2.43 min, M+Na=567.2 (fragments from losing Boc group also present).

Step C: (2S,3aR,5R,7aS)-tert-butyl hexahydro-2,5-methanopyrrolo[3,2-c]pyridine-1(6H)-carboxylate

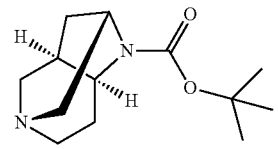 [SMILES: CC(C)(C)OC(=O)N1[C@H]2C[C@@H]3C[N@@](CC[C@@H]31)C2]

(2S,3aR,7aS)-5-benzyl 1-tert-butyl 2-((tosyloxy)methyl) hexahydro-1H-pyrrolo[3,2-c]pyridine-1,5(6H)-dicarboxylate (150 g, 275 mmol) and dry EtOH (4500 mL) were charged to a 10 L autoclave and under nitrogen atmosphere was charged palladium on carbon (49.8 g, 46.8 mmol). Applied 4 kg/$Cm^2$ pressure and stirring was continued for 3 hr at room temp. The reaction mixture filtered though celite and washed with dry ethanol. All the mother liquors were charged to 10000 mL round bottom flask under nitrogen flow, added potassium carbonate (190 g, 1377 mmol) and arranged a reflux condenser and heated to 75° C. overnight.

The reaction mixture was concentrated and diluted with 500 mL water and extracted with chloroform (3×500 mL) and dried over anhydrous $Na_2SO_4$. Removal of the solvent afforded (2S,3aR,5R,7aS)-tert-butyl hexahydro-2,5-methanopyrrolo[3,2-c]pyridine-1(6H)-carboxylate (53 g, 80%) of the crude compound as off white solid, which was of sufficient purity to use as such in the following transformations.

The absolute stereochemistry of this compound (and by analogy the preceding and subsequent compounds) is believed to be (2S,3aR,7aS) based on X-ray diffraction analysis performed on a sample of (2S,3aR,5R,7aS)-5-benzyl 1-tert-butyl 2-((tosyloxy)methyl)hexahydro-1H-pyrrolo[3,2-c]pyridine-1,5(6H)-dicarboxylate that was converted to (2S,3aR,5R,7aS)-octahydro-2,5-methanopyrrolo[3,2-c]pyridine, 2TsOH upon treatment with 2 equivalents of p-toluenesulfonic acid.

Step D: (2S,3aR,5R,7aS)-octahydro-2,5-methanopyrrolo[3,2-c]pyridine, 2HCl

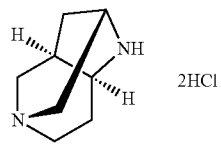

To a solution of hydrogen chloride, 4 N in dioxane (287 ml, 1150 mmol) was added finely ground (2S,3aR,5R,7aS)-tert-butyl hexahydro-2,5-methanopyrrolo[3,2-c]pyridine-1(6H)-carboxylate (27.4 g, 115 mmol) at rt over 15 min. After the addition, the internal temperature was 36.7° C. The mixture was stirred at ambient temperature. After 19 h, the LC/MS indicated absence of SM (M+H 239). The excess of 4 N HCl was removed by distillation under house vacuum at 45-50° C. The remaining residue was treated with EtOAc. The solvent was evaporated, dried under house vacuum to afford (2S,3aR,5R,7aS)-octahydro-2,5-methanopyrrolo[3,2-c]pyridine, 2HCl (25.6 g, 105%, small amount of water likely present by HNMR) NMR indicated absence of Boc. $^1$H NMR (400 MHz, DMSO-$d_6$) δ=11.85 (br. s., 1H), 10.70-9.86 (m, 2H), 4.34-3.93 (m, 4H), 3.78-3.48 (m, 3H), 3.41-3.23 (m, 2H), 3.22-3.11 (m, 1H), 2.75 (q, J=5.5 Hz, 1H), 2.36-2.19 (m, 1H), 2.18-2.03 (m, 2H), 2.03-1.88 (m, 1H). Integration totals 2 protons more than expected, possibly due to a small amount (~1 eq) of water.

Step E: ((2S,3aR,5R,7aS)-hexahydro-2,5-methanopyrrolo[3,2-c]pyridin-1(6H)-yl)(1H-indazol-3-yl)methanone

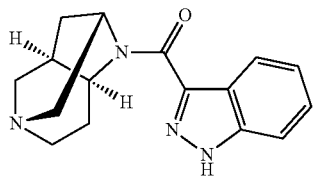

A mixture of 1H-indazole-3-carboxylic acid (4.05 g, 25.00 mmol), 1-hydroxypyridin-2(1H)-one (2.78 g, 25.00 mmol) and N1-((ethylimino)methylene)-N3,N3-dimethylpropane-1,3-diamine hydrochloride (4.79 g, 25.00 mmol) in MeCN (180 ml) was stirred at rt for 2 h 30 min. The mixture was then added via an addition funnel to a solution of (2S,3aR,5R,7aS)-octahydro-2,5-methanopyrrolo[3,2-c]pyridine, 2 HCl (5.28 g, 25.0 mmol) and N-ethyl-N-isopropylpropan-2-amine (12.92 g, 100 mmol) in MeCN (90 ml) over 40 min. After addition, the internal temperature was −6° C. The mixture was stirred with a cooling bath. After 18 h, the solvent in the reaction solution was evaporated to dryness. The remaining viscous oil was treated with $CHCl_3$ (150 mL) and saturated aqueous $NaHCO_3$ (100 mL). The layers were separated. The aqueous layer was extracted with $CHCl_3$ (2×50 mL). The combined extracts were washed with brine (2×75 mL), dried ($MgSO_4$), evaporated to give 8.4 g of the crude material. This batch was combined with a slightly smaller batches (4.22 g of (2S,3aR,5R,7aS)-octahydro-2,5-methanopyrrolo[3,2-c]pyridine, 2 HCl) for purification.

The combined batches were purified by silica gel chromatography on a 750 g RediSep column, flow rate=300 mL/min, equilibration volume=3.0 column volumes. Solvent A was chloroform, solvent B was 20% (2N Ammonia in methanol) in chloroform. The purification was performed by first eluting with 1.0 CV of solvent A, followed by a gradient 0-62% B over 8 CV and then holding at 62% B for 5.0 CV. $^1$H NMR indicated it contained about 12.7% of CHCl3.

This sample was combined with the purified product from another smaller reaction (4.25 g of (2S,3aR,5R,7aS)-octahydro-2,5-methanopyrrolo[3,2-c]pyridine, 2 HCl) for final purification and removal of residual chloroform. The combined lots (total 17.26 g) were dissolved in EtOH (150 mL) with sonication. The solvent was evaporated. The remaining residue was redissolved in EtOH (150 mL) with sonication. The solvent was evaporated to give 13.9 g. The sample was further dried under house vacuum. ((2S,3aR,5R,7aS)-hexahydro-2,5-methanopyrrolo[3,2-c]pyridin-1(6H)-yl)(1H-indazol-3-yl)methanone was obtained as a white solid (13.8 g, 74% yield), with a HPLC purity of 99.8%. LCMS Conditions: Waters BEH C18, 1.7 um, 150 mm (L)×2.1 mm (ID), 35° C., Flow rate=0.35 mL/min, Solvent A: 0.1% TFA in water, Solvent B: Acetonitrile. Gradient: 0-15 min, gradient 10-25% B, 15-28 min, gradient 25-95% B, 28-30 min, 95% B. Injection volume=2 uL of a 1 mg/mL sample in methanol. Retention time=6.43 min, [M+H]$^+$ at m/z=283. Accurate mass: [M+H]$^+$ at m/z=283.1546. Optical Rotation: $[α]_D^{25\ c}$=+142.9° (1.29 mg/mL in MeOH). $^1$H NMR (600 MHz, DMSO-$d_6$) δ 13.49 (br. s., 1H), 8.12 (d, J=8.3 Hz, 1H), 7.60 (d, J=8.4 Hz, 1H), 7.41 (t, J=7.5 Hz, 1H), 7.22 (t, J=7.4 Hz, 1H), 4.98 (br. s., 1H), 4.62 (br. s., 1H), 3.21 (dd, J=13.5, 8.3 Hz, 1H), 2.98 (m, 2H), 2.81 (m, 2H), 2.69 (d, J=13.0 Hz, 1H), 2.37 (d, J=4.8 Hz, 1H), 2.19 (m, 1H), 1.79 (m, 2H), 1.65 (m, 1H). $^{13}$C NMR (126 MHz, DMSO-$d_6$) δ 159.5, 140.3, 139.4, 126.5, 122.8, 121.9, 121.6, 110.4, 60.2, 56.5, 54.5, 50.4, 50.0, 37.9, 32.9, 21.2. Elemental analysis: (C,H, N) Calculated: (57.77%, 5.45%, 19.74%), found: (58.17%, 6.50%, 19.81%).

Example 35

((2S*,3aR*,5R*,7aS*)-(7-chloro-benzo[b]thiophen-2-yl)(hexahydro-2,5-methanopyrrolo[3,2-c]pyridin-1(6H)-yl)methanone

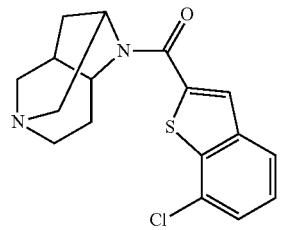 [SMILES: O=C(c1cc2cccc(Cl)c2s1)N1C2CC3CN(CCC31)C2]

(2S*,3aR*,5R*,7aS*)-octahydro-2,5-methanopyrrolo[3,2-c]pyridine, 2TFA (38.5 mg, 0.105 mmol), from Example 34, Step H, was reacted with 7-chlorobenzo[b]thiophene-2-carboxylic acid (22 mg, 0.105 mmol) according to the method of Example 1, Step G, affording the title compound, ((2S*,3aR*,5R*,7aS*)-(7-chloro-benzo[b]thiophen-2-yl)(hexahydro-2,5-methanopyrrolo[3,2-c]pyridin-1(6H)-yl)methanone (11 mg). $^1$H NMR (400 MHz, CHLOROFORM-d) δ=7.76 (d, J=7.8 Hz, 1H), 7.65 (br. s., 1H), 7.51-7.34 (m, 2H), 4.94-4.77 (m, 1H), 4.64-4.38 (m, 1H), 3.57-3.38 (m, 1H), 3.37-2.82 (m, 5H), 2.62-2.29 (m, 2H), 2.13-1.82 (m, 3H).

Example 36

((2S*,3aR*,5R*,7aS*)-(4-chlorophenyl)(hexahydro-2,5-methanopyrrolo[3,2-c]pyridin-1(6H)-yl)methanone

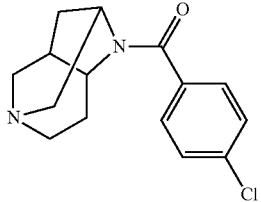 [SMILES: O=C(c1ccc(Cl)cc1)N1C2CC3CN(CCC31)C2]

(2S*,3aR*,5R*,7aS*)-octahydro-2,5-methanopyrrolo[3,2-c]pyridine, 2TFA (0.75 mmol), from Example 34, Step H, was dissolved in DMF (7.5 mL). Into a scintillation vial, 7.0 mL of this stock solution was placed along with DIPEA (0.61 mL, 3.5 mmol). In another scintillation vial, HATU (0.532 g, 1.4 mmol) was added and DMF (7.0 mL) and the mixture was sonicated to facilitate dissolution. To another vial, containing 4-chlorobenzoic acid (16 mg, 0.1 mmol), 0.5 mL of the HATU stock solution was added and the vial was shaken for 5 minutes, and then 0.5 mL of the amine/DIPEA stock solution was added and the vial was shaken overnight at ambient temperature. The reaction mixture was diluted with additional DMF to afford a total volume of 1.7 mL, and purified by preparative HPLC.

The crude material was purified via preparative LC/MS with the following conditions: Column: Waters XBridge C18, 19×100 mm, 5 µm particles; Guard Column: Waters XBridge C18, 19×10 mm, 5 µm particles; Mobile Phase A: water; Mobile Phase B: methanol; Buffer: 20-mM ammonium acetate; Gradient: 20-95% B over 8.3 minutes, then a 6.7 minute hold at 95% B; Flow: 25 mL/min. Fractions containing the desired product were combined and dried via centrifugal evaporation. The yield of the product was 16.9 mg, and its estimated purity by LCMS analysis was 100%. Two analytical LC/MS injections were used to determine the final purity. Injection 1 conditions: Column: Waters BEH C18, 2.0×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Retention time=1.34 min, M+H=277.16. Injection 2 conditions: Column: Waters BEH C18, 2.0×50 mm, 1.7 µm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Proton NMR was acquired in deuterated DMSO. $^1$H NMR (500 MHz, DMSO-d6) Shift=7.64-7.43 (m, 4H), 4.56-4.32 (m, 1H), 4.29-3.64 (m, 1H), 3.25-2.58 (m, 6H), 2.42-2.29 (m, 1H), 2.13-1.84 (m, 1H), 1.83-1.72 (m, 1H), 1.72-1.56 (m, 2H).

Example 37

((2S*,3aR*,5R*,7aS*)-(hexahydro-2,5-methanopyrrolo[3,2-c]pyridin-1(6H)-yl)(1-methyl-1H-indazol-3-yl)methanone

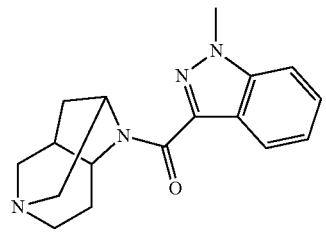 [SMILES: Cn1nc(C(=O)N2C3CC4CN(CCC42)C3)c2ccccc21]

The title compound was prepared according to the method of Example 36, starting with 1-methyl-1H-indazole-3-carboxylic acid (0.18 mg, 0.10 mmol).

The crude material was purified via preparative LC/MS with the following conditions: Column: Waters XBridge C18, 19×200 mm, 5 µm particles; Guard Column: Waters XBridge C18, 19×10 mm, 5 µm particles; Mobile Phase A: water; Mobile Phase B: methanol; Buffer: 20-mM ammonium acetate; Gradient: 20-95% B over 19.5 minutes, then a 14.0 minute hold at 95% B; Flow: 20 mL/min. Fractions containing the desired product were combined and dried via centrifugal evaporation. The yield of the product was 11.6 mg, and its estimated purity by LCMS analysis was 98%. Two analytical LC/MS injections were used to determine the final purity. Injection 1 conditions: Column: Waters BEH C18, 2.0×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Retention time=1.44 min, M+H=297.22. Injection 2 conditions: Column: Waters BEH C18, 2.0×50 mm, 1.7 µm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Proton NMR was acquired in deuterated DMSO. $^1$H NMR (500 MHz, DMSO-d6) Shift=8.21-8.03 (m, 1H), 7.80-7.66 (m, 1H), 7.47 (t, J=7.6 Hz, 1H), 7.26 (t, J=7.6 Hz, 1H), 5.17-4.96 (m, 1H), 4.66-4.48 (m, 1H), 4.16-4.07 (m, 3H), 3.25-2.97 (m, 3H), 2.86-2.62 (m, 3H), 2.49-2.35 (m, 1H), 2.25-2.13 (m, 1H), 1.93-1.52 (m, 3H).

Example 38

((2S*,3aR*,5R*,7aS*)-(hexahydro-2,5-methanopyrrolo[3,2-c]pyridin-1(6H)-yl)(3-phenyl-1H-pyrazol-5-yl)methanone

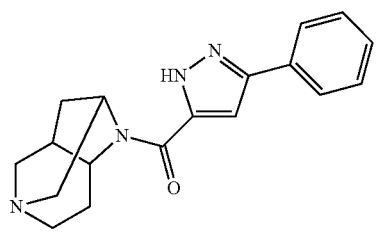 [SMILES: O=C(c1cc(-c2ccccc2)n[nH]1)N1C2CC3CN(CCC31)C2]

The title compound was prepared according to the method of Example 36, starting with 3-phenyl-1H-pyrazole-5-carboxylic acid (0.19 mg, 0.10 mmol).

The crude material was purified via preparative LC/MS with the following conditions: Column: Waters XBridge C18, 19×200 mm, 5 μm particles; Guard Column: Waters XBridge C18, 19×10 mm, 5 μm particles; Mobile Phase A: water; Mobile Phase B: methanol; Buffer: 20-mM ammonium acetate; Gradient: 20-95% B over 19.5 minutes, then a 14.0 minute hold at 95% B; Flow: 20 mL/min. Fractions containing the desired product were combined and dried via centrifugal evaporation. The yield of the product was 13.1 mg, and its estimated purity by LCMS analysis was 100%. Two analytical LC/MS injections were used to determine the final purity. Injection 1 conditions: Column: Waters BEH C18, 2.0×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; low: 1 mL/min. Injection 2 conditions: Column: Waters BEH C18, 2.0×50 mm, 1.7 μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Retention time=2.57 min, M+H=309.20. Proton NMR was acquired in deuterated DMSO. $^1$H NMR (500 MHz, DMSO-d6) Shift=13.69-13.55 (m, 1H), 7.82 (d, J=6.4 Hz, 2H), 7.47 (t, J=7.6 Hz, 2H), 7.42-7.33 (m, 1H), 7.20-7.02 (m, 1H), 5.14-4.66 (m, 1H), 4.58-4.42 (m, 1H), 3.24-3.11 (m, 1H), 3.09-2.90 (m, 2H), 2.84-2.63 (m, 3H), 2.47-2.30 (m, 1H), 2.19-2.06 (m, 1H), 1.92-1.73 (m, 2H), 1.68-1.57 (m, 1H).

Example 39

((2S*,3aR*,5R*,7aS*)-(hexahydro-2,5-methanopyrrolo[3,2-c]pyridin-1(6H)-yl)(1-methyl-1H-indol-3-yl)methanone

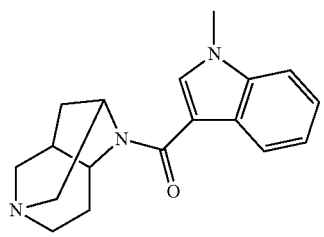 [SMILES: Cn1cc(C(=O)N2C3CC4CN(CCC42)C3)c2ccccc21]

The title compound was prepared according to the method of Example 36, starting with 1-methyl-1H-indole-3-carboxylic acid (0.18 mg, 0.10 mmol). The crude material was purified via preparative LC/MS with the following conditions: Column: Waters XBridge C18, 19×100 mm, 5 μm particles; Guard Column: Waters XBridge C18, 19×10 mm, 5 μm particles; Mobile Phase A: water; Mobile Phase B: ethanol; Buffer: 20-mM ammonium acetate; Gradient: 20-95% B over 8.3 minutes, then a 6.7 minute hold at 95% B; Flow: 25 mL/min. Fractions containing the desired product were combined and dried via centrifugal evaporation. The yield of the product was 21.4 mg, and its estimated purity by LCMS analysis was 100%. Two analytical LC/MS injections were used to determine the final purity. Injection 1 conditions: Column: Waters BEH C18, 2.0×50 mm, 1.7 μm particles; Mobile Phase A: 5:95 acetonitrile:water with 10 mM ammonium acetate; Mobile Phase B: 95:5 acetonitrile: water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7 μm particles; Mobile Phase A: 5:95 methanol:water with 10 mM ammonium acetate; Mobile Phase B: 95:5 methanol: water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Retention time=2.37 min, M+H=296.21. Proton NMR was acquired in deuterated DMSO. $^1$H NMR (500 MHz, DMSO-d6) Shift=7.93 (d, J=7.9 Hz, 1H), 7.73 (br. s., 1H), 7.49 (d, J=8.2 Hz, 1H), 7.28-7.19 (m, 1H), 7.17-7.07 (m, 1H), 4.68-4.59 (m, 1H), 4.39-4.27 (m, 1H), 3.85 (s, 3H), 3.25-3.09 (m, 2H), 3.08-2.61 (m, 5H), 2.42-2.29 (m, 1H), 1.87-1.52 (m, 3H).

Example 40

((2S*,3aR*,5R*,7aS*)-(5-chloro-1H-indazol-3-yl)(hexahydro-2,5-methanopyrrolo[3,2-c]pyridin-1(6H)-yl)methanone

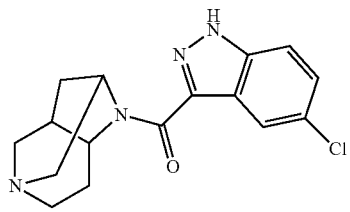 [SMILES: O=C(c1n[nH]c2ccc(Cl)cc12)N1C2CC3CN(CCC31)C2]

The title compound was prepared according to the method of Example 36, starting with 5-chloro-1H-indazole-3-carboxylic acid (0.18 mg, 0.10 mmol).

The crude material was purified via preparative LC/MS with the following conditions: Column: Waters XBridge C18, 19×200 mm, 5-µm particles; Guard Column: Waters XBridge C18, 19×10 mm, 5-µm particles; Mobile Phase A: water; Mobile Phase B: methanol; Buffer: 20-mM ammonium acetate; Gradient: 30-95% B over 19.5 minutes, then a 14.0 minute hold at 95% B; Flow: 20 mL/min. Fractions containing the desired product were combined and dried via centrifugal evaporation. The yield of the product was 11.8 mg, and its estimated purity by LCMS analysis was 95%. Two analytical LC/MS injections were used to determine the final purity. Injection 1 conditions: Column: Waters BEH C18, 2.0×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7 µm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Retention time=2.80 min, M+H=317.19. Proton NMR was acquired in deuterated DMSO. ¹H NMR (500 MHz, DMSO-d6) Shift=8.22-8.08 (m, 1H), 7.72-7.61 (m, 1H), 7.44 (dd, J=2.1, 8.9 Hz, 1H), 5.21-4.97 (m, 1H), 4.66-4.49 (m, 1H), 3.17-2.63 (m, 5H), 2.43-2.33 (m, 1H), 2.25-2.14 (m, 1H), 1.95-1.55 (m, 4H) (large water peak obscures some signals & complicates integration).

Example 41

((2S*,3aR*,5R*,7aS*)-(5-methoxy-1H-indazol-3-yl)(hexahydro-2,5-methanopyrrolo[3,2-c]pyridin-1(6H)-yl)methanone

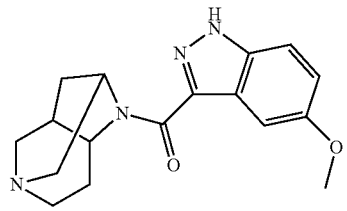 [SMILES: COc1ccc2[nH]nc(C(=O)N3C4CC5CN(CCC53)C4)c2c1]

The title compound was prepared according to the method of Example 36, starting with 5-methoxy-1H-indazole-3-carboxylic acid (0.19 mg, 0.10 mmol).

The crude material was purified via preparative LC/MS with the following conditions: Column: Waters XBridge C18, 19×200 mm, 5 µm particles; Guard Column: Waters XBridge C18, 19×10 mm, 5 µm particles; Mobile Phase A: water; Mobile Phase B: methanol; Buffer: 20-mM ammonium acetate; Gradient: 10-95% B over 19.5 minutes, then a 14.0 minute hold at 95% B; Flow: 20 mL/min. Fractions containing the desired product were combined and dried via centrifugal evaporation. The yield of the product was 27.3 mg, and its estimated purity by LCMS analysis was 100%. Two analytical LC/MS injections were used to determine the final purity. Injection 1 conditions: Column: Waters BEH C18, 2.0×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7-µm particles; Mobile Phase A: 5:95 methanol:water with 10 mM ammonium acetate; MobilePhase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Retention time=1.72 min, M+H=313.23. Proton NMR was acquired in deuterated DMSO. ¹H NMR (500 MHz, DMSO-d6) Shift=8.36 (s, 1H), 7.34 (d, J=3.1 Hz, 1H), 7.32 (d, J=8.9 Hz, 1H), 7.22 (dd, J=2.9, 9.0 Hz, 1H), 4.36-4.27 (m, 1H), 4.20-4.10 (m, 1H), 3.80 (s, 3H), 3.20-3.11 (m, 1H), 2.98-2.71 (m, 4H), 2.68-2.60 (m, 1H), 2.42-2.32 (m, 1H), 2.26-2.13 (m, 1H), 1.86-1.69 (m, 2H), 1.63-1.51 (m, 1H).

Example 42

((2S*,3aR*,5R*,7aS*)-(6-fluoro-1H-indazol-3-yl)(hexahydro-2,5-methanopyrrolo[3,2-c]pyridin-1(6H)-yl)methanone

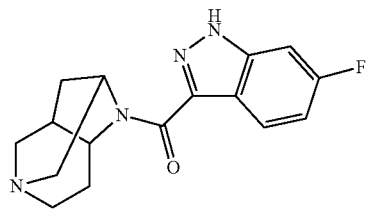 [SMILES: O=C(c1n[nH]c2cc(F)ccc12)N1C2CC3CN(CCC31)C2]

The title compound was prepared according to the method of Example 36, starting with 6-fluoro-1H-indazole-3-carboxylic acid (0.18 mg, 0.10 mmol).

The crude material was purified via preparative LC/MS with the following conditions: Column: Waters XBridge C18, 19×100 mm, 5-µm particles; Guard Column: Waters XBridge C18, 19×10 mm, 5 µm particles; Mobile Phase A: water; Mobile Phase B: methanol; Buffer: 20-mM ammonium acetate; Gradient: 20-95% B over 8.3 minutes, then a 6.7 minute hold at 95% B; Flow: 25 mL/min. Fractions containing the desired product were combined and dried via centrifugal evaporation. The yield of the product was 17.5 mg, and its estimated purity by LCMS analysis was 98%. Two analytical LC/MS injections were used to determine the final purity. Injection 1 conditions: Column: Waters BEH C18, 2.0×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Retention time=1.38 min, M+H=301.13. Injection 2 conditions: Column: Waters BEH C18, 2.0×50 mm, 1.7 µm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Proton NMR was acquired in deuterated DMSO. 1H NMR (500 MHz, DMSO-d6) Shift=8.21-8.09 (m, 1H), 7.41 (dd, J=2.1, 9.5 Hz, 1H), 7.12 (dt, J=2.1, 9.2 Hz, 1H), 5.17-4.94 (m, 1H), 4.65-4.51 (m, 1H), 3.24-2.64 (m, 6H), 2.43-2.33 (m, 1H), 2.23-2.12 (m, 1H), 1.91 (s, 3H).

Example 43

((2S*,3aR*,5R*,7aS*)-(6-methoxy-1H-indazol-3-yl)(hexahydro-2,5-methanopyrrolo[3,2-c]pyridin-1(6H)-yl)methanone

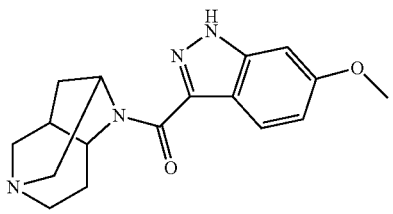 [SMILES: COc1ccc2c(C(=O)N3C4CC5CN(CCC53)C4)n[nH]c2c1]

The title compound was prepared according to the method of Example 36, starting with 6-methoxy-1H-indazole-3-carboxylic acid (0.19 mg, 0.10 mmol). The crude material was purified via preparative LC/MS with the following conditions: Column: Waters XBridge C18, 19×200 mm, 5 µm particles; Guard Column: Waters XBridge C18, 19×10 mm, 5 µm particles; Mobile Phase A: water; Mobile Phase B: methanol; Buffer: 20-mM ammonium hydroxide; Gradient: 10-95% B over 19.5 minutes, then a 14.0 minute hold at 95% B; Flow: 20 mL/min. Fractions containing the desired product were combined and dried via centrifugal evaporation. The yield of the product was 14.2 mg, and its estimated purity by LCMS analysis was 100%. Two analytical LC/MS injections were used to determine the final purity. Injection 1 conditions: Column: Waters BEH C18, 2.0×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Retention time=1.35 min, M+H=313.20. Injection 2 conditions: Column: Waters BEH C18, 2.0×50 mm, 1.7 µm particles; Mobile Phase A: 5:95 methanol:water with 10 mM ammonium acetate; Mobile Phase B: 95:5 methanol: water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Proton NMR was acquired in deuterated DMSO. $^1$H NMR (500 MHz, DMSO-d6) Shift=8.21-8.09 (m, 1H), 7.41 (dd, J=2.1, 9.5 Hz, 1H), 7.12 (dt, J=2.1, 9.2 Hz, 1H), 5.17-4.94 (m, 1H), 4.65-4.51 (m, 1H), 3.24-2.64 (m, 6H), 2.43-2.33 (m, 1H), 2.23-2.12 (m, 1H), 1.91 (s, 3H).

Example 44

((2S*,3aR*,5R*,7aS*)-(5-bromo-1H-indazol-3-yl)(hexahydro-2,5-methanopyrrolo[3,2-c]pyridin-1(6H)-yl)methanone

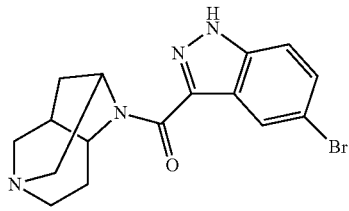

The title compound was prepared according to the method of Example 36, starting with 5-bromo-1H-indazole-3-carboxylic acid (0.24 mg, 0.10 mmol).

The crude material was purified via preparative LC/MS with the following conditions: Column: Waters XBridge C18, 19×200 mm, 5 µm particles; Guard Column: Waters XBridge C18, 19×10 mm, 5 µm particles; Mobile Phase A: water; Mobile Phase B: methanol; Buffer: 20-mM ammonium hydroxide; Gradient: 10-95% B over 19.5 minutes, then a 14.0 minute hold at 95% B; Flow: 20 mL/min. Fractions containing the desired product were combined and dried via centrifugal evaporation. The yield of the product was 13.3 mg, and its estimated purity by LCMS analysis was 100%. Two analytical LC/MS injections were used to determine the final purity. Injection 1 conditions: Column: Waters BEH C18, 2.0×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Retention time=1.63 min, M+H=361.10. Injection 2 conditions: Column: Waters BEH C18, 2.0×50 mm, 1.7 µm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Proton NMR was acquired in deuterated DMSO. 1H NMR (500 MHz, DMSO-d6) Shift=14.19-13.05 (m, 1H), 8.36-8.29 (m, 1H), 7.64-7.59 (m, 1H), 7.57-7.52 (m, 1H), 5.04 (br. s., 1H), 4.67-4.49 (m, 1H), 3.25-2.63 (m, 6H), 2.42-2.31 (m, 1H), 2.29-2.14 (m, 1H), 1.94-1.54 (m, 3H).

Example 45

((2S*,3aR*,5R*,7aS*)-(7-chloro-1H-indazol-3-yl)(hexahydro-2,5-methanopyrrolo[3,2-c]pyridin-1(6H)-yl)methanone

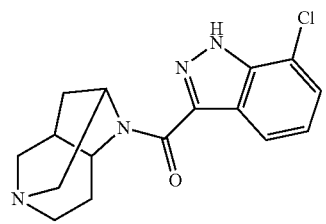 [SMILES: O=C(c1n[nH]c2c(Cl)cccc12)N1C2CC3CN(CCC31)C2]

The title compound was prepared according to the method of Example 36, starting with 7-chloro-1H-indazole-3-carboxylic acid (0.19 mg, 0.10 mmol).

The crude material was purified via preparative LC/MS with the following conditions: Column: Waters XBridge C18, 19×200 mm, 5 μm particles; Guard Column: Waters XBridge C18, 19×10 mm, 5 μm particles; Mobile Phase A: water; Mobile Phase B: methanol; Buffer: 20-mM ammonium hydroxide; Gradient: 10-95% B over 19.5 minutes, then a 14.0 minute hold at 95% B; Flow: 20 mL/min. Fractions containing the desired product were combined and dried via centrifugal evaporation. The yield of the product was 15.8 mg, and its estimated purity by LCMS analysis was 100%. Two analytical LC/MS injections were used to determine the final purity. Injection 1 conditions: Column: Waters BEH C18, 2.0×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Retention time=1.49 min, M+H=317.17. Injection 2 conditions: Column: Waters BEH C18, 2.0×50 mm, 1.7 μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Proton NMR was acquired in deuterated DMSO. 1H NMR (500 MHz, DMSO-d6) Shift=14.27-13.96 (m, 1H), 8.18-8.03 (m, 1H), 7.53 (d, J=7.3 Hz, 1H), 7.24 (t, J=7.8 Hz, 1H), 5.18-4.91 (m, 1H), 4.66-4.50 (m, 1H), 3.07 (s, 3H), 2.92-2.66 (m, 3H), 2.38 (br. s., 1H), 2.24-2.08 (m, 1H), 1.98-1.57 (m, 3H).

Example 46

((2S*,3aR*,5R*,7aS*)-(6-chloro-1H-indazol-3-yl)(hexahydro-2,5-methanopyrrolo[3,2-c]pyridin-1(6H)-yl)methanone

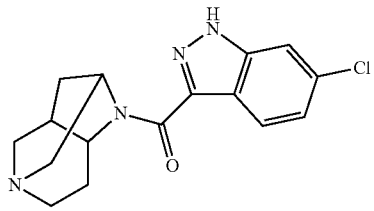 [SMILES: O=C(c1n[nH]c2cc(Cl)ccc12)N1C2CC3CN(CCC31)C2]

The title compound was prepared according to the method of Example 36, starting with 6-chloro-1H-indazole-3-carboxylic acid (0.19 mg, 0.10 mmol). The crude material was purified via preparative LC/MS with the following conditions: Column: Waters XBridge C18, 19×200 mm, 5 μm particles; Guard Column: Waters XBridge C18, 19×10 mm, 5 μm particles; Mobile Phase A: water; Mobile Phase B: methanol; Buffer: 20-mM ammonium hydroxide; Gradient: 10-95% B over 19.5 minutes, then a 14.0 minute hold at 95% B; Flow: 20 mL/min. Fractions containing the desired product were combined and dried via centrifugal evaporation. The material was further purified via preparative LC/MS with the following conditions: Column: Waters XBridge C18, 19×200 mm, 5 μm particles; Guard Column: Waters XBridge C18, 19×10 mm, 5 μm particles; Mobile Phase A: water; Mobile Phase B: methanol; Buffer: 20-mM ammonium acetate; Gradient: 30-95% B over 19.5 minutes, then a 14.0 minute hold at 95% B; Flow: 20 mL/min. Fractions containing the desired product were combined and dried via centrifugal evaporation. The yield of the product was 14.4 mg, and its estimated purity by LCMS analysis was 98%. Two analytical LC/MS injections were used to determine the final purity. Injection 1 conditions: Column: Waters BEH C18, 2.0×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Retention time=1.55 min, M+H=317.13. Injection 2 conditions: Column: Waters BEH C18, 2.0×50 mm, 1.7 μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Proton NMR was acquired in deuterated DMSO. 1H NMR (500 MHz, DMSO-d6) Shift=14.06-12.96 (m, 1H), 8.13 (d, J=8.5 Hz, 1H), 7.71 (s, 1H), 7.26 (dd, J=1.5, 8.5 Hz, 1H), 5.19-4.88 (m, 1H), 4.69-4.48 (m, 1H), 3.22-2.62 (m, 10H), 2.45-2.31 (m, 1H), 2.24-2.10 (m, 1H), 1.65 (d, J=14.0 Hz, 1H).

Example 47

((2S*,3aR*,5R*,7aS*)-benzo[d]isoxazol-3-yl(hexahydro-2,5-methanopyrrolo[3,2-c]pyridin-1(6H)-yl)methanone

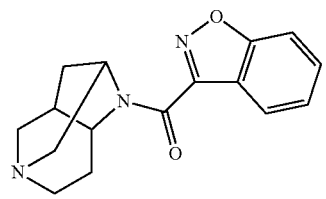 [SMILES: O=C(c1noc2ccccc12)N1C2CC3CN(CCC31)C2]

The title compound was prepared according to the method of Example 36, starting with benzo[d]isoxazole-3-carboxylic acid (0.16 mg, 0.10 mmol).

The crude material was purified via preparative LC/MS with the following conditions: Column: Waters XBridge C18, 19×200 mm, 5 μm particles; Guard Column: Waters XBridge C18, 19×10 mm, 5 μm particles; Mobile Phase A: water; Mobile Phase B: methanol; Buffer: 20-mM ammonium hydroxide; Gradient: 10-95% B over 19.5 minutes, then a 14.0 minute hold at 95% B; Flow: 20 mL/min. Fractions containing the desired product were combined and dried via centrifugal evaporation. The yield of the product was 14.4 mg, and its estimated purity by LCMS analysis was 99%. Two analytical LC/MS injections were used to determine the final purity. Injection 1 conditions: Column: Waters BEH C18, 2.0×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Retention time=1.40 min, M+H=284.18. Injection 2 conditions: Column: Waters BEH C18, 2.0×50 mm, 1.7 μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Proton NMR was acquired in deuterated DMSO. 1H NMR (500 MHz, DMSO-d6) Shift=8.07-7.98 (m, 1H), 7.91-7.85 (m, 1H), 7.78-7.72 (m, 1H), 7.50 (t, J=7.3 Hz, 1H), 4.72-4.58 (m, 1H), 4.51-4.43 (m, 1H), 3.29-3.01 (m, 2H), 2.90-2.61 (m, 4H), 2.47-2.38 (m, 1H), 2.27-2.13 (m, 1H), 1.99-1.76 (m, 2H), 1.75-1.46 (m, 1H).

Example 48

((2S*,3aR*,5R*,7aS*)-(4-methoxy-1H-indazol-3-yl)(hexahydro-2,5-methanopyrrolo[3,2-c]pyridin-1(6H)-yl)methanone

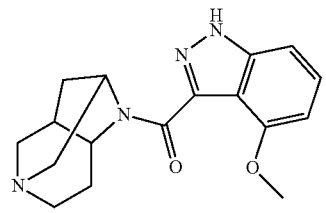 [SMILES: COc1cccc2[nH]nc(C(=O)N3C4CC5CN(CCC53)C4)c12]

The title compound was prepared according to the method of Example 36, starting with 4-methoxy-1H-indazole-3-carboxylic acid (0.19 mg, 0.10 mmol).

The crude material was purified via preparative LC/MS with the following conditions: Column: Waters XBridge C18, 19×200 mm, 5-μm particles; Guard Column: Waters XBridge C18, 19×10 mm, 5-μm particles; Mobile Phase A: water; Mobile Phase B: methanol; Buffer: 20-mM ammonium acetate; Gradient: 10-95% B over 19.5 minutes, then a 14.0 minute hold at 95% B; Flow: 20 mL/min. Fractions containing the desired product were combined and dried via centrifugal evaporation. The yield of the product was 17.4 mg, and its estimated purity by LCMS analysis was 98%. Two analytical LC/MS injections were used to determine the final purity. Injection 1 conditions: Column: Waters BEH C18, 2.0×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7 μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Retention time=2.07 min, M+H=313.20. Proton NMR was acquired in deuterated DMSO. $^1$H NMR (500 MHz, DMSO-d6) Shift=13.28-13.10 (m, 1H), 7.36-7.27 (m, 1H), 7.11 (d, J=8.5 Hz, 1H), 6.64-6.54 (m, 1H), 4.57-4.41 (m, 1H), 3.86 (s, 3H), 4.04-3.48 (m, 1H), 3.17-2.57 (m, 6H), 2.45-2.33 (m, 1H), 2.32-2.24 (m, 1H), 1.93-1.79 (m, 2H), 1.68 (s, 1H).

Example 49

((2S*,3aR*,5R*,7aS*)-(6-methyl-1H-indazol-3-yl)(hexahydro-2,5-methanopyrrolo[3,2-c]pyridin-1(6H)-yl)methanone

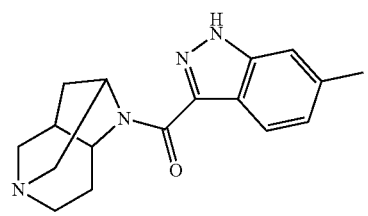 [SMILES: Cc1ccc2c(C(=O)N3C4CC5CN(CCC53)C4)n[nH]c2c1]

The title compound was prepared according to the method of Example 36, starting with 6-methyl-1H-indazole-3-carboxylic acid (0.18 mg, 0.10 mmol).

The crude material was purified via preparative LC/MS with the following conditions: Column: Waters XBridge C18, 19×200 mm, 5-μm particles; Guard Column: Waters XBridge C18, 19×10 mm, 5-μm particles; Mobile Phase A: water; Mobile Phase B: methanol; Buffer: 20-mM ammonium acetate; Gradient: 10-95% B over 19.5 minutes, then a 14.0 minute hold at 95% B; Flow: 20 mL/min. Fractions containing the desired product were combined and dried via centrifugal evaporation. The yield of the product was 12.9 mg, and its estimated purity by LCMS analysis was 98%. Two analytical LC/MS injections were used to determine the final purity. Injection 1 conditions: Column: Waters BEH C18, 2.0×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7 μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Retention time=2.65 min, M+H=297.21. Proton NMR was acquired in deuterated DMSO. $^1$H NMR (500 MHz, DMSO-d6) Shift=13.43-13.24 (m, 1H), 7.99 (d, J=8.5 Hz, 1H), 7.42-7.31 (m, 1H), 7.06 (d, J=8.5 Hz, 1H), 5.21-4.95 (m, 1H), 4.67-4.48 (m, 1H), 3.24-2.60 (m, 9H), 2.46 (s, 3H), 2.41-2.31 (m, 1H), 2.26-2.09 (m, 1H), 1.79 (s, 3H).

Examples 49a and 49b (2S,3aR,5R,7aS)-(6-methyl-1H-indazol-3-yl)(hexahydro-2,5-methanopyrrolo[3, 2-c]pyridin-1(6H)-yl)methanone and (2R,3aS,5S,7aR)-(6-methyl-1H-indazol-3-yl)(hexahydro-2,5-methanopyrrolo[3,2-c]pyridin-1(6H)-yl)methanone

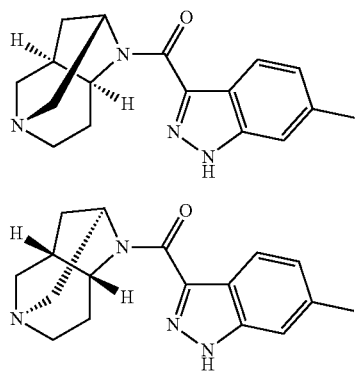

49a

49b (2S*,3aR*,5R*,7aS*)-(6-methyl-1H-indazol-3-yl)(hexahydro-2,5-methanopyrrolo[3,2-c]pyridin-1 (6H)-yl)methanone (100 mg) was separated into individual enantiomers by supercritical fluid chromatography on a Chiralpak IC-H column (30×250 mm, 5 uM), eluting with 30% MeOH containing 0.1% diethylamine in $CO_2$ (temperature=35° C., Pressure=150 bar, Flow rate: 70 mL/min for 25 min, injection: 1 mL of ~10 mg/mL solution in $CHCl_3$:MeOH (4:1), UV monitored at 290 nm). The first peak was collected to afford (2S,3aR,5R,7aS)-(6-methyl-1H-indazol-3-yl)(hexahydro-2,5-methanopyrrolo[3,2-c]pyridin-1(6H)-yl)methanone (42 mg, 80%). The second peak was collected to give (2R,3aS,5S,7aR)-(6-methyl-1H-indazol-3-yl)(hexahydro-2,5-methanopyrrolo[3,2-c]pyridin-1(6H)-yl)methanone (48 mg, 91%).

(2S,3aR,5R,7aS)-(6-methyl-1H-indazol-3-yl)(hexahydro-2,5-methanopyrrolo[3,2-c]pyridin-1 (6H)-yl)methanone was also prepared by the following alternate method:

In a 3000 ml 4 neck flask was charged (2S,3aR,5R,7aS)-octahydro-2,5-methanopyrrolo[3,2-c]pyridine (22.77 g, 108 mmol), Acetonitrile (450 ml), and DIPEA (75 ml, 431 mmol). This was stirred under nitrogen at rt.

Meanwhile in a second 2000 ml single neck flask was charged 6-methyl-1h-indazole-3-carboxylic acid (19.00 g, 108 mmol), 2-pyridinol-1-oxide (11.98 g, 108 mmol), EDC (20.67 g, 108 mmol) and Acetonitrile (850 ml). This suspension was stirred vigorously for 1 hr.

The amine was cooled down to approx. −5° C. in a MeOH/$CO_2$ bath. Using a piece of teflon tubing and a slight vacuum, the activated ester suspension was drawn over to the main reaction vessel slowly. Addition time was about 20 min, keeping the temperature of the reaction mixture under 0° C. When transfer was completed, the bath was replaced with crushed ice and the reaction was stirred at 0° C. After 5 h, the reaction mixture was concentrated to remove volatiles. The crude was combined with the crude material from two smaller reactions (2.68 and 0.55 g (2S,3aR,5R,7aS)-octahydro-2,5-methanopyrrolo[3,2-c]pyridine) for purification.

The combined batches were divided in half and each half was purified by silica gel chromatography on a 1500 g RediSep column, flow rate=1000 mL/min, equilibration volume=3.0 column volumes. Solvent A was chloroform, solvent B was 20% (2N Ammonia in methanol) in chloroform. The purification was performed by first eluting with 1.0 CV of solvent A, followed by a gradient 0-50% B over 10 CV and then holding at 50% B for 5.0 CV.

The two samples obtained after chromatography, both contained residual chloroform. To remove residual chloroform, they were combined (34.36 g) and dissolved in EtOH (350 mL). The mixture was warmed at 35° C. to become a clear, light yellow solution. After 1 h, the solution was cooled to rt. The solvent in the solution was evaporated to dryness, dried in vacuo overnight affording 29.6 g.

NMR indicated that EDC urea (M+H 174) was present.

The solvent of SFC purified fractions (total about 16 L) was evaporated. The off-white solid was dissolved in EtOH (250 mL) at 40° C. with stirring. The solvents in the solution were evaporated. The solid was then transferred to a crystal dish, dried under a desiccator in vacuo at rt. After 2.5 h, the NMR indicated about 1.3 wt % of EtOH was present. The sample was continued to dried in vacuo overnight.

After drying at rt for 17 h, NMR indicated about same amount of EtOH remained as that of 2.5 h. The sample in the crystal dish was ground and transferred to a 2-oz amber bottle, dried in a desiccator in vacuo for 2 h to give 25.50 g. Submitted for GC analysis. The results indicated about 1.8 wt % of EtOH present. The sample was further dried at rt.

The sample approached constant weight to give (2S,3aR,5R,7aS)-(6-methyl-1H-indazol-3-yl)(hexahydro-2,5-methanopyrrolo[3,2-c]pyridin-1(6H)-yl)methanone (25.48 g) with a HPLC purity of 99.6%. LCMS Conditions: Waters BEH C18, 1.7 um, 150 mm (L)×2.1 mm (ID), 35° C., Flow rate=0.35 mL/min, Solvent A: 0.1% TFA in water, Solvent B: 0.05% TFA in Acetonitrile. Gradient: 0-15 min, gradient 10-25% B, 15-28 min, gradient 25-95% B, 28-30 min, 95% B. Injection volume=2 uL of a 1 mg/mL sample in methanol. Retention time=9.46 min, $[M+H]^+$ at m/z=297. Accurate mass: $[M+H]^+$ at m/z=297.1702. Optical Rotation: $[\alpha]_D^{25\ c}$=+135.45° (0.1 mg/mL in MeOH). $^1$H NMR (DMSO-$d_6$) δ: 13.33 (s, 1H), 7.97-8.02 (m, 1H), 7.36 (s, 1H), 7.03-7.07 (m, 1H), 4.99 (br. s., 1H), 4.58-4.62 (m, 1H), 3.20 (dd, J=13.4, 8.4 Hz, 1H), 2.97-3.12 (m, 2H), 2.74-2.84 (m, 2H), 2.65-2.72 (m, 1H), 2.45 (s, 4H), 2.32-2.40 (m, 1H), 2.15-2.22 (m, 1H), 1.74-1.89 (m, 2H), 1.54-1.68 (m, 1H). $^{13}$C NMR (DMSO-$d_6$) δ: 160.1, 141.4, 139.8, 136.7, 124.4, 122.0, 121.6, 110.0, 60.7, 56.9, 55.0, 50.9, 50.5, 38.3, 33.4, 21.9, 21.7. Karl Fischer: 0.72% water. Elemental analysis: (C,H,N) Calculated: (68.23%, 6.89%, 18.60%), found: (68.55%, 7.22%, 18.60%).

(2R,3aS,5S,7aR)-(6-methyl-1H-indazol-3-yl)(hexahydro-2,5-methanopyrrolo[3,2-c]pyridin-1 (6H)-yl)methanone was also prepared by the following alternate method:

(2R,3aS,5S,7aR)-octahydro-2,5-methanopyrrolo[3,2-c]pyridine, 2 HCl was prepared in the same manner as (2S,3aR,5R,7aS)-octahydro-2,5-methanopyrrolo[3,2-c]pyridine, 2 HCl by the method of example 1a, alternate route, from the opposite enantiomer from the SFC separation of example 1a, alternate step A.

To a mixture of 6-methyl-1H-indazole-3-carboxylic acid (11.08 g, 62.9 mmol), 1-hydroxypyridin-2(1H)-one (6.99 g, 62.9 mmol) in MeCN (440 ml) was added N1-((ethylimino)methylene)-N3,N3-dimethylpropane-1,3-diamine hydrochloride (12.06 g, 62.9 mmol) in portions over 5 minutes. After addition was complete, the mixture was stirred at rt (3:40 pm) for 2 h 30 min. The mixture was transferred to an addition funnel. This mixture was added to a solution of (2R,3aS,5S,7aR)-octahydro-2,5-methanopyrrolo[3,2-c]

pyridine, 2 HCl (13.28 g, 62.9 mmol) and N-ethyl-N-isopropylpropan-2-amine (32.5 g, 252 mmol) in MeCN (220 ml) over 15 min, while maintaining internal temperature between −30 to −25° C. with acetone/dry ice bath. After addition, the mixture was stirred with an cooling bath and slowly warmed to ambient temperature.

After 16 h, the LC/MS was taken and it looked identical to that of 40 min. the reaction was worked up. The solid was filtered off. The solvent in the filtrate was evaporated to dryness. The remaining oil was dissolved in CHCl₃ (400 mL), washed with saturated NaHCO₃ (160 mL). The layers were separated. The aqueous layer was extracted with CHCl₃ (1×100 mL). The combined extracts were washed with saturated NaHCO₃ (2×120 mL), dried (MgSO₄), evaporated to give the crude material.

The crude was purified by silica gel chromatography on a 750 g RediSep column, flow rate=300 mL/min, equilibration volume=3.0 column volumes. Solvent A was chloroform, solvent B was 20% (2N Ammonia in methanol) in chloroform. The purification was performed by first eluting with 1.0 CV of solvent A, followed by a gradient 0-50% B over 10 CV and then holding at 50% B for 5.0 CV, affording (2R,3aS,5S,7aR)-(6-methyl-1H-indazol-3-yl)(hexahydro-2,5-methanopyrrolo[3,2-c]pyridin-1 (6H)-yl)methanone (16.2 g)

The sample was recrystallized from MeCN (600 mL) at 65° C. for 3 h and then slowly cooled to rt overnight. The white solid was collected on a filter, washed with MeCN, dried under house vacuum under a stream of nitrogen. To give (2R,3aS,5S,7aR)-(6-methyl-1H-indazol-3-yl)(hexahydro-2,5-methanopyrrolo[3,2-c]pyridin-1(6H)-yl)methanone (12.1 g, 64.8%) with a HPLC purity of 99.8%. LCMS Conditions: Waters BEH C18, 1.7 um, 150 mm (L)×2.1 mm (ID), 35° C., Flow rate=0.35 mL/min, Solvent A: 0.1% TFA in water, Solvent B: 0.05% TFA in Acetonitrile. Gradient: 0-15 min, gradient 10-25% B, 15-28 min, gradient 25-95% B, 28-30 min, 95% B. Injection volume=2 uL of a 1 mg/mL sample in methanol. Retention time=9.21 min, [M+H]⁺ at m/z=297. Accurate mass: [M+H]⁺ at m/z=297.1698. Optical Rotation: $[\alpha]_D^{25}$ ᶜ=−132.14° (1.66 mg/mL in MeOH). Karl Fischer: 0.75% water. Elemental analysis: (C,H,N) Calculated: (67.77%, 6.45%, 19.74%), found: (68.17%, 6.51%, 19.81%).

Example 50

(1H-indazol-3-yl)(octahydro-2,8-epiminoindolizin-9-yl)methanone

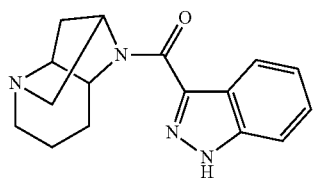 [SMILES: O=C(c1n[nH]c2ccccc12)N1C2CC3C1CCCN3C2]

Step A: tert-butyl 2-((benzyloxy)methyl)-1H-pyrrolo[3,2-b]pyridine-1-carboxylate

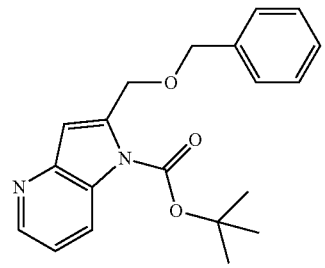

A resealable pressure vessel was charged with tert-butyl (2-bromopyridin-3-yl) carbamate (6.75 g, 24.7 mmol), ((prop-2-yn-1-yloxy)methyl)benzene (4.34 g, 29.7 mmol), bis(triphenylphosphine) palladium(II) chloride (0.87 g, 1.24 mmol), copper(I) iodide (0.47 g, 2.47 mmol), triethylamine (69 mL, 494 mmol) and DMF (25 mL). The mixture was degassed by bubbling nitrogen through for several minutes, the flask was sealed and the reaction mixture was stirred overnight. After ~18 h, LC/MS showed a ~7:4 mixture of intermediate and fully cyclized product. This ratio was essentially unchanged after an additional ~7 h, so an additional portion of copper(I) iodide (1 g, ~5 mmol) was added and the mixture was stirred at rt for an additional ~18 h, at which time, the conversion was complete by LC/MS (LC/MS Method A: retention time=3.41 min, M+H=339.15). The mixture was diluted with EtOAc and washed with saturated ammonium chloride (4×) and brine (1×). The organics were dried over sodium sulfate, filtered and evaporated, and the crude material purified by silica gel chromatography, eluting with 20-50% EtOAc in hexanes, affording tert-butyl 2-((benzyloxy)methyl)-1H-pyrrolo[3,2-b]pyridine-1-carboxylate (7.6 g, 91%). ¹H NMR (400 MHz, CHLOROFORM-d) δ=8.52 (d, J=3.5 Hz, 1H), 8.34 (d, J=8.3 Hz, 1H), 7.48-7.32 (m, 5H), 7.21 (dd, J=4.6, 8.4 Hz, 1H), 6.95 (s, 1H), 4.97 (d, J=0.8 Hz, 2H), 4.72 (s, 2H), 1.69 (s, 9H).

Step B: tert-butyl 2-(hydroxymethyl)octahydro-1H-pyrrolo[3,2-b]pyridine-1-carboxylate

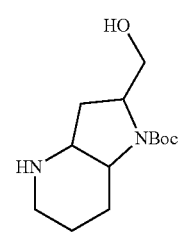

Tert-butyl 2-((benzyloxy)methyl)-1H-pyrrolo[3,2-b]pyridine-1-carboxylate (7.6 g, 22.46 mmol) in Ethanol (200 mL) added to 20% palladium hydroxide on carbon, 50% wet (4 g, 2.85 mmol) in a 500 mL Parr bottle. The mixture was hydrogenated at 50 psi overnight. TLC and LC/MS show only partial conversion to first reduction product. The bottle was recharged with H₂ to 55 psi and reacted overnight again, at which point starting material still remained. The mixture was transferred to larger 2 L bottle, diluted with additional EtOH (200 mL) and AcOH (40 mL) and the bottle was returned to the Parr shaker. After ~4 h, LC/MS showed some further conversion to debenzylated material. The mixture was allowed to react on Parr shaker over the weekend, at which point reduction was still incomplete. The mixture was filtered to remove the Pd(OH)₂ and PtO₂(~1 g) was added. Hydrogenation was continued 2 days more at which point complete conversion was seen. The catalyst was removed by filtration, and the filtrate was concentrated on the rotovap, made basic by the addition of saturated sodium bicarbonate, extracted 3× with chloroform, dried over sodium sulfate and evaporated and carried on crude to the next step.

Step C: 4-benzyl 1-tert-butyl 2-(hydroxymethyl) hexahydro-1H-pyrrolo[3,2-b]pyridine-1,4(2H)-dicarboxylate

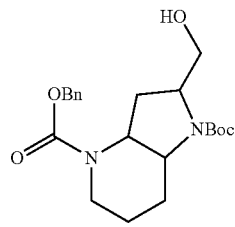 [SMILES: CC(C)(C)OC(=O)N1C(CO)CC2C1CCCN2C(=O)OCc1ccccc1]

Tert-butyl 2-(hydroxymethyl)octahydro-1H-pyrrolo[3,2-b]pyridine-1-carboxylate (2.9 g, 9.17 mmol) was dissolved in THF (40 mL) and 10% aqueous potassium carbonate solution (40 mL) and benzylchloroformate (2.75 mL, 19.35 mmol) was added. The biphasic mixture was stirred for 30 min, diluted with chloroform and the phases separated. The aqueous fraction was extracted twice again with chloroform and the combined organics dried over sodium sulfate. The crude mixture was purified by silica gel chromatography with an ethyl acetate/hexanes mixture (20%-100%). The title compound was obtained as a mixture of diastereomers (3.32 g, 93%) and taken on to the next step as such. LC/MS Method A: Retention time=3.92 min, M+H=391.22.

Step D: (2S*,3aS*,7aS*)-4-benzyl 1-tert-butyl 2-((tosyloxy)methyl)hexahydro-1H-pyrrolo[3,2-b]pyridine-1,4(2H)-dicarboxylate

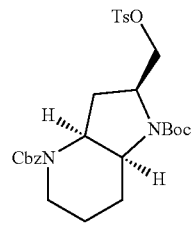

4-benzyl 1-tert-butyl 2-(hydroxymethyl)hexahydro-1H-pyrrolo[3,2-b]pyridine-1,4(2H)-dicarboxylate (3.32 g, 8.50 mmol) was dissolved in pyridine (20 mL) and tosyl chloride (1.95 g, 10.2 mmol) was added. The yellow reaction mixture was stirred overnight. The bulk of the pyridine was evaporated on the rotovap and the mixture was partitioned between 0.1N HCl and Chloroform. The aqueous fraction was extracted 3×, wash with saturated sodium bicarbonate and brine, and dried over sodium sulfate. After filtration and evaporation of the solvent, silica gel chromatography with a gradient of 20-100% EtOAc in hexanes afforded two diastereomers, the first eluting peak (3 g, 64%), which was the major component, was taken on to the next step. HNMR was recorded but was uninformative due to a complex mixture of rotomers from both the Boc and Cbz groups.

Step E: tert-butyl octahydro-2,8-epiminoindolizine-9-carboxylate

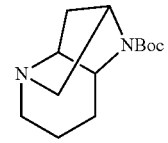

A 500 mL Parr bottle was charged with (2S*,3aS*,7aS*)-4-benzyl 1-tert-butyl 2-((tosyloxy)methyl)hexahydro-1H-pyrrolo[3,2-b]pyridine-1,4(2H)-dicarboxylate (3 g, 5.51 mmol), palladium on carbon (0.586 g, 5.51 mmol) and ethanol (100 mL). The mixture was hydrogenated at 55 psi on Parr shaker for 3 h. LC/MS shows complete cleavage of CBz. The mixture was filtered to remove the catalyst. To the filtrate, sodium carbonate (~1 g). The mixture was refluxed 1 h at which point TLC showed complete conversion to cyclized product. Water was added and most of the ethanol was evaporated. The mixture was extracted with chloroform (3×), dried over sodium sulfate, filtered and evaporated to afford an oil that was purified by silica gel chromatography, eluting with 5-40% (9:1 MeOH:NH₄OH) in chloroform, affording tert-butyl octahydro-2,8-epiminoindolizine-9-carboxylate (0.87 g, 3.65 mmol, 66.3% yield). ¹H NMR (400 MHz, CHLOROFORM-d) δ=4.65-4.21 (m, 1H), 3.65 (br. s., 1H), 3.31 (br. s., 1H), 3.13 (d, J=9.5 Hz, 1H), 3.02-2.67 (m, 3H), 2.59-2.27 (m, 1H), 1.91-1.59 (m, 3H), 1.55-1.39 (m, 10H), 1.32-1.08 (m, 1H).

Step F: Octahydro-2,8-epiminoindolizine, 2TFA

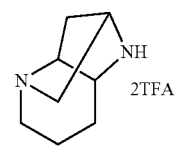

Tert-butyl octahydro-2,8-epiminoindolizine-9-carboxylate (0.29 g, 1.2 mmol) was dissolved in chloroform (3 mL) and TFA (3 mL) was added. The mixture was stirred for 30 min, the volatiles were evaporated and the residue was azeotroped with chloroform to afford Octahydro-2,8-epiminoindolizine, 2TFA. The yield of the reaction was assumed to be quantitative for use in the next step without purification. ¹H NMR (400 MHz, DMSO-d₆) δ=11.22 (br. s., 1H), 9.86 (br. s., 1H), 9.23 (br. s., 1H), 4.46 (s, 1H), 4.31 (s, 2H), 3.96 (br. s., 1H), 3.61 (dd, J=2.0, 13.3 Hz, 1H), 3.50-3.36 (m, 2H), 3.35-3.14 (m, 1H), 2.26-1.71 (m, 5H).

Step G: (1H-indazol-3-yl)(octahydro-2,8-epiminoindolizin-9-yl)methanone

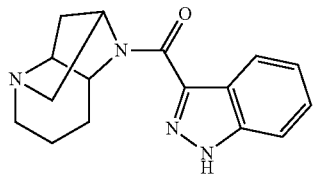 [SMILES: O=C(c1n[nH]c2ccccc12)N1C2CC3C1CCCN3C2]

A scintillation vial was charged with octahydro-2,8-epiminoindolizine, 2 TFA (35 mg, 0.096 mmol), HATU (45 mg, 0.119 mmol), 1H-indazole-3-carboxylic acid (19 mg, 0.115 mmol) DIPEA (0.1 mL, 0.57 mmol) and DMF (1 mL). The mixture was allowed to stir at ambient temperature overnight. The solvent was removed by evaporation under a stream of nitrogen, and the residue was partitioned between chloroform and saturated aqueous sodium bicarbonate. The phases were separated and the aqueous fraction extracted twice more with chloroform. The combined organic phases were dried over sodium sulfate, filtered and the solvent was removed by evaporation on the rotovap. The resultant residue was purified by silica gel chromatography, eluting with a gradient from 5% to 40% (9:1 MeOH/NH4OH) in chloroform, affording the title compound (20 mg, 70%). LC/MS Method A: Retention time=1.99 min, M+H=283.15. $^1$H NMR (400 MHz, CHLOROFORM-d) δ=11.41 (br. s., 1H), 8.41-8.09 (m, 1H), 7.58-7.50 (m, 1H), 7.44 (ddd, J=1.1, 7.0, 8.2 Hz, 1H), 7.34-7.24 (m, 1H), 5.32 (s, 1H), 4.68-4.23 (m, 1H), 3.62-2.76 (m, 6H), 2.09-1.58 (m, 4H), 1.38-1.24 (m, 2H).

Example 51

(7-chlorobenzo[b]thiophen-2-yl)(octahydro-2,8-epiminoindolizin-9-yl)methanone

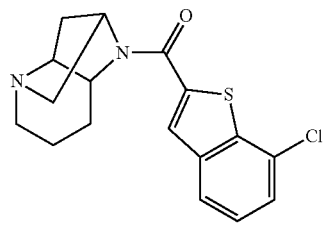 [SMILES: O=C(c1cc2cccc(Cl)c2s1)N1C2CC3C1CCCN3C2]

Subjecting chlorobenzo[b]thiophene-2-carboxylic acid (24 mg, 0.115 mmol) to the reaction conditions for Example 1 Step G afforded (7-chlorobenzo[b]thiophen-2-yl)(octahydro-2,8-epiminoindolizin-9-yl)methanone (28 mg, 84%). LC/MS Method A: Retention time=2.97 min, M+H=333.09. $^1$H NMR (400 MHz, CHLOROFORM-d) δ=7.78 (d, J=8.0 Hz, 1H), 7.70 (s, 1H), 7.50-7.45 (m, 1H), 7.44-7.38 (m, 1H), 4.90-4.79 (m, 1H), 4.39-4.26 (m, 1H), 3.80-3.46 (m, 2H), 3.23-3.00 (m, 3H), 2.23-2.03 (m, 2H), 1.96-1.21 (m, 14H) (Peaks in alkyl region are broadened, presumably due to the presence of rotomers, and more protons than expected were found, likely due to the presence of some water in the sample.)

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

The invention claimed is:

1. A compound of formula I, or a stereoisomer thereof,

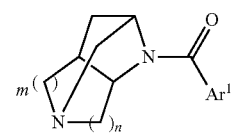

where:
Ar$^1$ is selected from the group consisting of phenyl, pyrrolyl, furanyl, thienyl, pyrazolyl, isoxazolyl, isothiazolyl, imidazolyl, oxazolyl, thiazolyl, triazolyl, oxadiazolyl, thiadiazolyl, pyridinyl, pyridazinyl, pyrimidinyl, pyrazinyl, naphthalenyl, indolyl, indazolyl, benzofuranyl, dihydrobenzofuranyl, benzodioxolanyl, benzothiophenyl, dihydrobenzothiophenyl, benzoisothiazolyl, benzothiazolyl, thienopyrazinyl, pyrrolopyridinyl, pyrrolotriazinyl, benzoisoxazolyl, quinolinyl, isoquinolinyl, quinoxalinyl, and naphthyridinyl, and is substituted with 0-3 substituents selected from the group consisting of cyano, halo, alkyl, haloalkyl, cycloalkyl, alkoxy, haloalkoxy, alkylthio, and Ar$^2$;
Ar$^2$ is phenyl substituted with 0-3 substituents selected from cyano, halo, alkyl, haloalkyl, alkoxy, and haloalkoxy; and
m is 2 and n is 1; or
m is 1 and n is 2; or
m is 0 and n is 3;
or a pharmaceutically acceptable salt thereof.

2. A compound of claim 1 where:
Ar$^1$ is phenyl, pyrazolyl, indolyl, indazolyl, pyrazolopyridinyl, benzofuranyl, thiophenyl, benzoisoxazolyl, benzoisothiazolyl, or isoquinolinyl, and is substituted with 0-3 substituents selected from the group consisting of cyano, halo, alkyl, haloalkyl, cycloalkyl, alkoxy, haloalkoxy, alkylthio, and Ar$^2$; and
Ar$^2$ is phenyl substituted with 0-3 substituents selected from cyano, halo, alkyl, haloalkyl, alkoxy, and haloalkoxy;
or a pharmaceutically acceptable salt thereof.

3. A compound of claim 1 where Ar$^1$ is phenyl, pyrazolyl, indolyl, indazolyl, pyrazolopyridinyl, benzofuranyl, thiophenyl, benzoisoxazolyl, benzoisothiazolyl, or isoquinolinyl, and is substituted with 0-1 substituents selected from halo, alkyl, cycloalkyl, alkoxy, and Ar²; and Ar² is phenyl; or a pharmaceutically acceptable salt thereof.

4. A compound of claim 1 where m is 2 and n is 1.

5. A compound of claim 1 where m is 1 and n is 2.

6. A compound of claim 1 where m is 0 and n is 3.

7. A compound of claim 1 where Ar¹ is indazolyl substituted with 0-3 substituents selected from the group consisting of cyano, halo, alkyl, haloalkyl, cycloalkyl, alkoxy, and haloalkoxy; or a pharmaceutically acceptable salt thereof.

8. A compound of claim 1 selected from the group consisting of

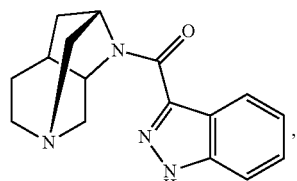,

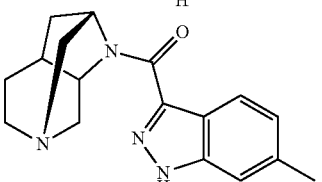,

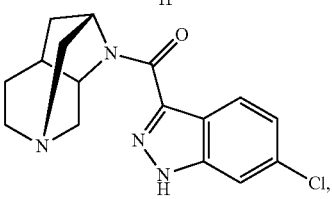,

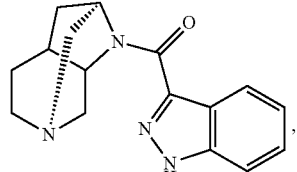,

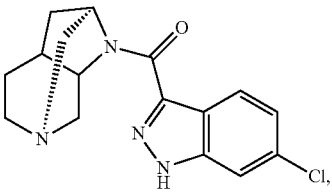,

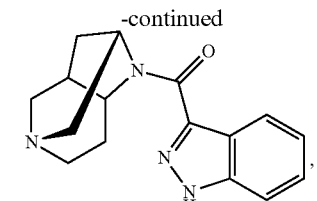,

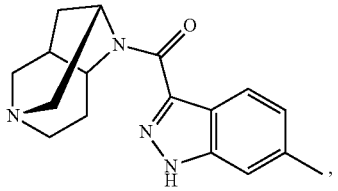,

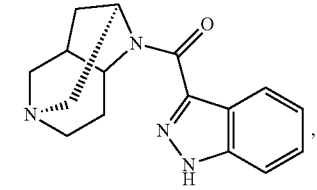,

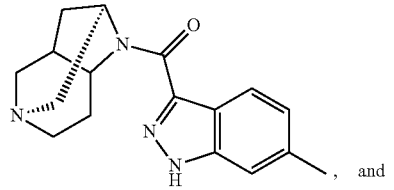, and

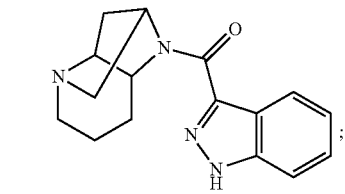 [SMILES: O=C(c1n[nH]c2ccccc12)N1C2CC3C1CCCN3C2];

or a pharmaceutically acceptable salt thereof.

9. A pharmaceutical composition comprising a therapeutically effective amount of a compound of claim 1, or a pharmaceutically acceptable salt thereof, and a pharmaceutically acceptable carrier.

* * * * *